US008524868B2

(12) United States Patent
Xia et al.

(10) Patent No.: US 8,524,868 B2
(45) Date of Patent: Sep. 3, 2013

(54) POLYPEPTIDE FRAGMENTS OF THE HEPATITIS E VIRUS, THE VACCINE COMPOSITION COMPRISING SAID FRAGMENTS AND THE DIAGNOSTIC KITS

(75) Inventors: Ningshao Xia, Hangzhou (CN); Jun Zhang, Hangzhou (CN); Shaowei Li, Hangzhou (CN); Shengxiang Ge, Hangzhou (CN); Ying Gu, Hangzhou (CN); Zhiqiang He, Hangzhou (CN)

(73) Assignees: Beijing Wantai Biological Pharmacy Enterprise Co., Ltd., Beijing (CN); Xiamen University, Xiamen, Fujian Province (CN)

( * ) Notice: Subject to any disclaimer, the term of this patent is extended or adjusted under 35 U.S.C. 154(b) by 187 days.

(21) Appl. No.: 12/614,896

(22) Filed: Nov. 9, 2009

(65) Prior Publication Data

US 2010/0150962 A1 Jun. 17, 2010

Related U.S. Application Data

(60) Continuation of application No. 12/557,741, filed on Sep. 11, 2009, which is a division of application No. 10/381,770, filed as application No. PCT/CN01/01469 on Sep. 30, 2001, now Pat. No. 7,615,228.

(30) Foreign Application Priority Data

Sep. 30, 2000 (CN) .................................. 00 1 30634

(51) Int. Cl.
*C12P 21/08* (2006.01)
*A61K 39/29* (2006.01)

(52) U.S. Cl.
USPC .................. 530/387.1; 530/388.1; 530/388.8; 424/228.1; 424/189.1; 424/184.1; 435/5; 435/69.3

(58) Field of Classification Search
None
See application file for complete search history.

(56) References Cited

U.S. PATENT DOCUMENTS

| 5,885,768 A | 3/1999 | Reyes et al. |
| 6,054,567 A | 4/2000 | Emerson et al. |

FOREIGN PATENT DOCUMENTS

| CA | 1319629 C | 6/1993 |
| JP | 63-196293 A | 8/1988 |
| WO | 95/17501 A1 | 6/1995 |
| WO | 96/10580 A2 | 4/1996 |
| WO | 96/12807 A2 | 5/1996 |
| WO | 97/05164 A1 | 2/1997 |
| WO | 01/22916 A2 | 4/2001 |

OTHER PUBLICATIONS

Aggarwal and Krawczynski. Hepatitis E: an overview and recent advances in clinical and laboratory research. J Gastroenterol Hepatol. Jan. 2000;15(1):9-20. Review. Abstract Only.*

Ji-Zhong Zhang et al; "Conformational Antigenic Determinants Generated by Interactions Between a Bacterially Expressed Recombinant Peptide of the Hepatitis E Virus Structural Protein", Journal of Medical Virology 64: 2001, pp. 125-132.

David A Anderson, et al; "ELISA for IgG-class antibody to hepatitis E virus based on a highly conserved, conformational epitope expressed in *Eschericia coli*" Journal of Virological Methods 81 (1999), pp. 131-142, XP000942370.

Li Xing, et al; "Recombinant Hepatitis E Capsid Protein Self-Assembles into a Dual-Domain T= 1 Particle Presenting Native Virus Epitopes", Virology 265, (1999), pp. 35-45 Article ID viro.1999. 0005, available online at: http://www.idealibrary.com.

Tian-Cheng Li, et al; "Expression and Self-Assembly of Empty Virus-Like Particles of Hepatitis E Virus", Journal of Virology, Oct. 1997, pp. 7207-7213, vol. 71, No. 10, XP-002295364.

Michaela A. Riddell, et al; "Identification of Immunodominant and Conformational Epitopes in the Capsid Protein of Hepatitis E Virus by Using Monoclonal Antibodies", Journal of Virology, Sep. 2000, vol. 74, No. 17, pp. 8011-8017, XP-000942369.

Fan Li, et al; "Recombinant Subunit ORF2.1 Antigen and Induction of Antibody Against Immunodominant Epitopes in the Hepatitis E Virus Capsid Protein", Journal of Medical Virology, 60 (2000), pp. 379-386, XP-000941268.

Thomas Muster, et al; "Cross-Neutralizing Activity against Divergent Human Immunodeficiency Virus Type 1 Isolates Induced by the gp41 Sequence ELDKWAS", Journal of Virology, Jun. 1994, vol. 68, No. 6, pp. 4031-4034.

Shengqiang Li, et al; "Influenza A Virus Transfectants with Chimeric Hemagglutinins Containing Epitopes from Different Subtypes", Journal of Virology, Jan. 1992, vol. 66, No. 1, pp. 399-404.

M.O. Favorov, et al; "IgM and IgG Antibodies to Hepatitis E Virus (HEV) Detected by an Enzyme Immunoassay Based on an HEV-Specific Artificial Recombinant Mosaic Protein", Journal of Medical Virology, 50 (1996), pp. 50-58.

Suzanne U. Emerson, et al; "Recombinant vaccines for hepatitis E", http://tmm.trends.com, Trends in Molecular Medicine, vol. 7, No. 10, Oct. 2001.

USPTO Office Action mailed Aug. 23, 2005 for U.S. Appl. No. 10/381,770.

USPTO Office Action mailed Mar. 15, 2006 for U.S. Appl. No. 10/381,770.

(Continued)

*Primary Examiner* — Michelle S Horning
(74) *Attorney, Agent, or Firm* — Ladas & Parry LLP

(57) ABSTRACT

The present invention relates to polypeptide(s) comprising the amino acid sequence as set forth in SEQ ID No. 1 of hepatitis E virus ORF 2 or its fragment, which is in the form of n-polymeric polypeptide, wherein n is an integer from 1-180; to a chimeric protein consisting of a polypeptide of the present invention and a conserved fragment of hemaglutin antigen from influenza virus; to a polypeptide of the present invention bound to a polypeptide containing epitope from hepatitis E virus ORF3 or an immunogenic fragment thereof; to a recombinant expression vector comprising the DNA molecule encoding the above polypeptides and the host cell transformed with said recombinant expression vector which is able to express polypeptide of the present invention. The present invention further relates to a vaccine composition against hepatitis E virus which comprises the above-mentioned polypeptide, or diagnostic kit for hepatitis E virus infection comprising the above-mentioned polypeptide, which includes IgG, IgM, or total antibody diagnostic kit for hepatitis E virus, and to the use of vaccine composition and diagnostic kit for prophylaxis, diagnosis and/or treatment of hepatitis E virus infection.

26 Claims, 13 Drawing Sheets

(56) References Cited

OTHER PUBLICATIONS

USPTO Office Action mailed Nov. 3, 2006 for U.S. Appl. No. 10/381,770.
USPTO Office Action mailed Jun. 21, 2007 for U.S. Appl. No. 10/381,770.
USPTO Office Adtion mailed Feb. 6, 2008 for U.S. Appl. No. 10/381,770.
USPTO Office Action mailed Sep. 4, 2008 for U.S. Appl. No. 10/381,770.
USPTO Office Action mailed Dec. 23, 2008 for U.S. Appl. No. 10/381,770.
Database UniProt [Online] Nov. 1, 1996 "Structural protein (Fragment).", XP002303171 retrieved from EBI accession No. UNIPROT:Q81861; Database accession No. Q81861 the whole document.
Database Uniprot [Online] Nov. 1, 1996 "Structural protein (Fragment).", XP002303172, retrieved from EBI accession No. UNIPROT: Q81860 Database Accession No. Q81860, the whole document.
Tian-Cheng Li, et al; "Essential Elements of the Capsid Protein for Self-Assembly into Empty Virus-Like Particles of Hepatitis E Virus", Journal of Virology, vol. 79, No. 20, Oct. 2005, pp. 12999-13006, XP007916926, ISSN: 0022-538X the whole document.
European Search Report; dated May 26, 2011; EP10 18 3446.
Yury E. Khudyakov, et al; "Antigenic Domains of the Open Reading Frame 2-Encoded Protein of Hepatitis E Virus", Journal of Clinical Microbiology, Sep. 1999, pp. 2863-2871, vol. 37, No. 9.
Yu E Khudyakov, et al; "Immunodominant Antigenic Regions in a Structural Protein of the Hepatitis E Virus", Virology, 1994, 198, pp. 390-393.
M.S. Balayan, et al.;"Evidence for a virus in non-A, non-B hepatitis transmitted via the fecal-oral route", Intervirology, 1983;20(1): Abstract only provided.
D.C.Wong, et al; Epidemic and endemic hepatitis in India: evidence for a non-A, non-B hepatitis virus aetiology, Lancet Oct. 25, 1980, 2(8200), abstract only.
Hla Myint, et al; "A Clinical and Epidemiological Study of an Epidemic of Non-A Non-B Hepatitis in Rangoon", Am. J. Trop. Med. Hyg., 34(6), Nov. 1985, pp. 1183-1189.
El-Hadj Belabbes, et al; "Epidemic non-A, non-B Viral Hepatitis in Algeria: Strong Evidence for Its Spreading by Water", Journal of Medical Virology 16:257-263, Jul. 1985, Article first published online: Dec. 11, 2005.
Chau Huu Hau, et al; "Prevalence of Enteric Hepatitis A and E Viruses in the Mekong River Delta Region of Vietnam", Am. J. Trop Med. Hyg., 60(2), 1999, (exact date not given or found) pp. 277-280.
E. Tsega, et al; "Acute sporadic viral hepatitis in Ethiopia: causes, risk factors, and effects on pregnancy", Department of Internal Medicine, Faculty of Medicine, Addis Ababa University, Ethiopia; Clin. Infec Dis. (1992) 14(4), abstract only.
J.B. Dilawari, et al; "Hepatitis E Virus: Epidemiological, Clinical and Serological Studies of a North Indian Epidemic", Indian J. Gastroenterol, Apr. 1994; 13 (2), pp. 44-48.
S.H. Hussaini, et al; "Severe hepatitis E infection during pregnancy", Journal of Viral Hepatitis, Jan. 1997, 4, 51-54.
Albert W. Tam, et al; "Hepatitis E Virus (HEV): Molecular Cloning and Sequencing of the Full-Length Viral Genome", Virology 185, 120-131, Nov. 1991.
Thein Thein Aye, et al; "Complete nucleotide sequence of a hepatitis E virus isolated from the Xinjiang epidemic (1986-1988) of China", Nucleic Acids Research, vol. 20, No. 13, p. 3512, Submitted May 29, 1992.
Thein Thein Aye, et al; "Sequence and Gene Structure of the Hepatitis E Virus Isolated from Myanmar", Virus Genes 7:1, 95-110, Feb. 1993.
Chiao-Chain Huang, et al; "Molecular Cloning and Sequencing of the Mexico Isolate of Hepatitis E Virus (HEV)", Virology 191, 550-558, Dec. 1992.
G.R. Reyes, et al; "Molecular organization and replication of hepatitis E virus (HEV)", Arch Virol Suppl. 1993:7: abstract only, no exact date found or given.
Eric E. Mast, et al; "Evaluation of Assays for Antibody to Hepatitis E Virus by a Serum Panel", Hepatology, vol. 27, Issue 3, pp. 857-861, Mar. 1998.
Yamina Kabrane-Lazizi, et al; "Evidence for Widespread Infection of Wild Rats With Hepatitis E Virus in the United States", Am. J. Trop Med. Hyg., 61(2): pp. 331-335, Aug. 1999.
Shahid Jameel, et al; "Expression in Animal Cells and Characterization of the Hepatitis E Virus Structural Proteins", Journal of Virology, Jan. 1996, p. 207-216, vol. 70, No. 1.
Sergei A. Tsarev, et al; "Successful passive and active immunization of cynomolgus monkeys against hepatitis E", Proc. Natl. Acad. Sci. USA, vol. 91, pp. 10198-10202, Oct. 1994.
S.A. Tsarev, et al; "ELISA for antibody to hepatitis E virus (HEV) based on complete open-reading frame-2 protein expressed in insect cells: identification of HEV infection in primates", J. Infect. Dis. Aug. 1993, 168(2) abstract.
Sergei A. Tsarev, et al; "Recombinant vaccine against hepatitis E: dose response and protection against heterologous challenge", Vaccine, vol. 15, No. 17/18, pp. 1834-1838, Dec. 1997.
Yifan Zhang, et al; "Expression, Characterization, and Immunoreactivities of a Soluble Hepatitis E Virus Putative Capsid Protein Species Expressed in Insect Cells", Clinical and Diagnostic Laboratory Immunology, Jul. 1997, p. 423-428, vol. 4, No. 4.
C. Patrick Mcatee, et al; "Purification of a Soluble Hepatitis E Open Reading Fkrame 2-Derived Protein with Unique Antigenic Properties", Protein Expression and Purification 8, 262-270, Sep. 1996.
David A. Anderson, et al; "ELISA for IgG-class antibody to hepatitis E virus based on a highly conserved, conformational epitope expressed in *Eschericia coli*", Journal of Virological Methods 81, 131-142, Aug. 1999.
Fan Li, et al; "Persistent and Transient Antibody Responses to Hepatitis E Virus Detected by Western Immunoblot Using Open Reading Frame 2 and 3 and Gluththione *S*-Transferase Fusion Proteins", Journal of Clinical Microbiology, Sep. 1994, p. 2060-2066, vol. 31, No. 9.
Fan Li, et al; "Amino-Terminal Epitopes are Exposed When Full-Length Open Reading Frame 2 of Hepatitis E Virus is Expressed in *Escherichia coli*, But Carboxy-Terminal Epitopes are Masked", Journal of Medical Virology, Jul. 1997.
Fan Li, et al; "Recombinant Subunit ORF2.1 Antigen and Induction of Antibody Against Immunodominant Epitopes in the Hepatitis E Virus Capsid Protein", Journal of Medical Virology 60:379-386, Apr. 2000.

\* cited by examiner

FIG.9
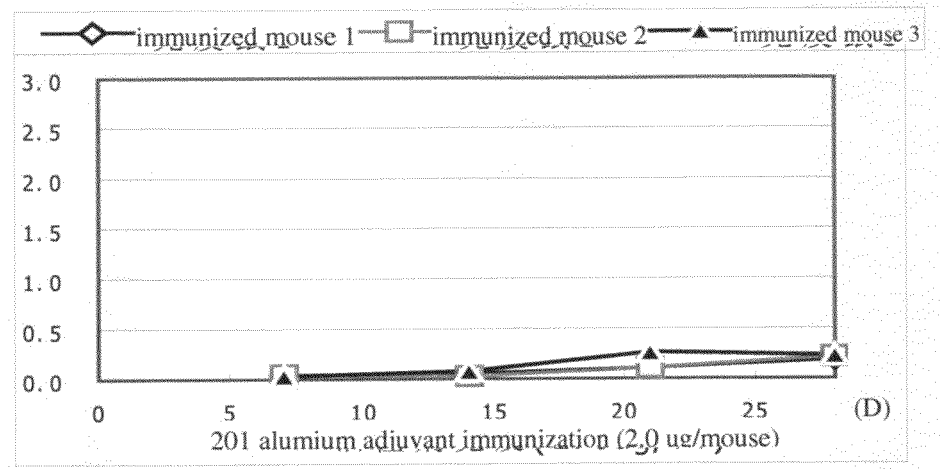
201 alumium adjuvant immunization (2.0 μg/mouse) (D)
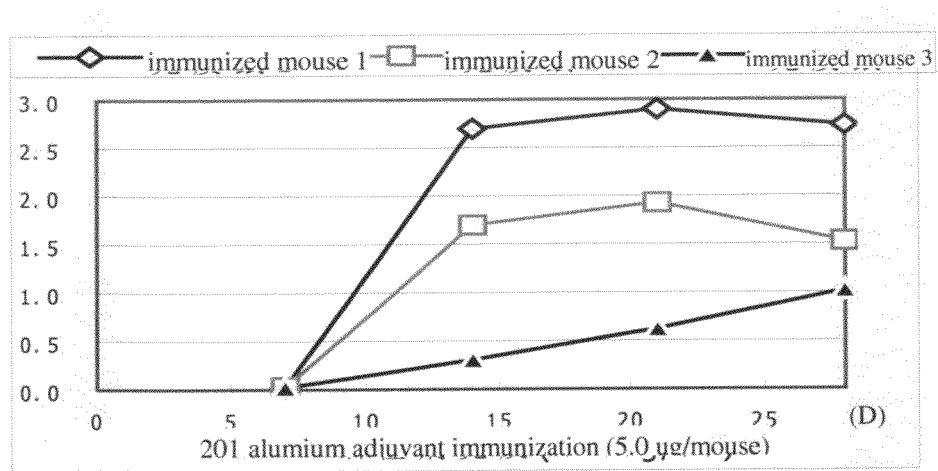
201 alumium adjuvant immunization (5.0 μg/mouse) (D)
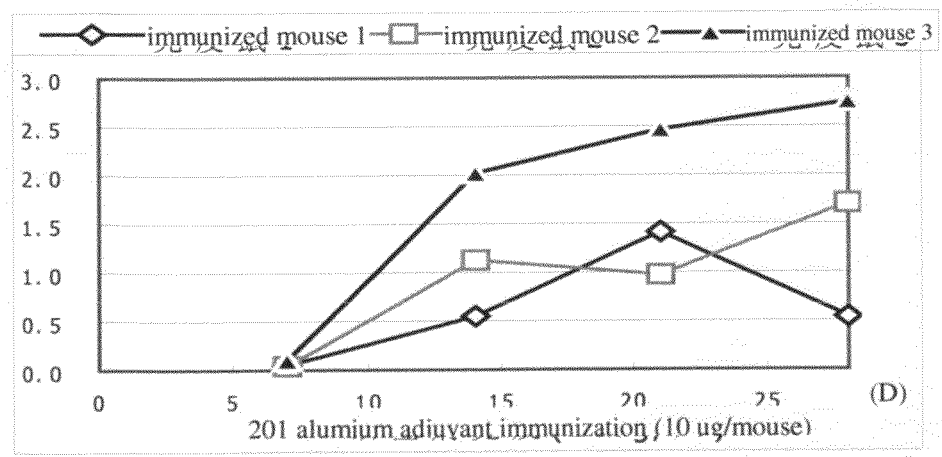
201 alumium adjuvant immunization (10 μg/mouse) (D)

SEQUENCE LISTING

<160> NUMBER OF SEQ ID NOS: 92

<210> SEQ ID NO 1
<211> LENGTH: 660
<212> TYPE: PRT
<213> ORGANISM: Hepatitis E virus

<400> SEQUENCE: 1

```
Met Arg Pro Arg Pro Ile Leu Leu Leu Leu Met Phe Leu Pro Met
1               5                   10                  15

Leu Pro Ala Pro Pro Gly Gln Pro Ser Gly Arg Arg Arg Gly Arg
                20                  25                  30

Arg Ser Gly Gly Ser Gly Gly Gly Phe Trp Gly Asp Arg Val Asp Ser
                35                  40                  45

Gln Pro Phe Ala Ile Pro Tyr Ile His Pro Thr Asn Pro Phe Ala Pro
    50                  55                  60

Asp Val Thr Ala Ala Ala Gly Ala Gly Pro Arg Val Arg Gln Pro Ala
65                  70                  75                  80

Arg Pro Leu Gly Ser Ala Trp Arg Asp Gln Ala Gln Arg Pro Ala Ala
                85                  90                  95

Ala Ser Arg Arg Arg Pro Thr Thr Ala Gly Ala Ala Pro Leu Thr Ala
                100                 105                 110

Val Ala Pro Ala His Asp Thr Pro Pro Val Pro Asp Val Asp Ser Arg
            115                 120                 125

Gly Ala Ile Leu Arg Arg Gln Tyr Asn Leu Ser Thr Ser Pro Leu Thr
        130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175

Thr Glu Ala Ser Asn Tyr Ala Gln Tyr Arg Val Ala Arg Ala Thr Ile
            180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Thr Thr Pro Thr Ser Val Asp Met
    210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Pro Val Asn Ser Tyr
        275                 280                 285
```

Thr Asn Thr Pro Tyr Thr Gly Ala Leu Gly Leu Leu Asp Phe Ala Leu
290                 295                 300

Glu Leu Glu Phe Arg Asn Leu Thr Pro Gly Asn Thr Asn Thr Arg Val
305                 310                 315                 320

Ser Arg Tyr Ser Ser Thr Ala Arg His Arg Leu Arg Arg Gly Ala Asp
                325                 330                 335

Gly Thr Ala Glu Leu Thr Thr Thr Ala Ala Thr Arg Phe Met Lys Asp
                340                 345                 350

Leu Tyr Phe Thr Ser Thr Asn Gly Val Gly Glu Ile Gly Arg Gly Ile
            355                 360                 365

Ala Leu Thr Leu Phe Asn Leu Ala Asp Thr Leu Leu Gly Gly Leu Pro
370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Ala Ile Pro His Asp Ile Asp
                420                 425                 430

Leu Gly Glu Ser Arg Val Val Ile Gln Asp Tyr Asp Asn Gln His Glu
            435                 440                 445

Gln Asp Arg Pro Thr Pro Ser Pro Ala Pro Ser Arg Pro Phe Ser Val
450                 455                 460

Leu Arg Ala Asn Asp Val Leu Trp Leu Ser Leu Thr Ala Ala Glu Tyr
465                 470                 475                 480

Asp Gln Ser Thr Tyr Gly Ser Ser Thr Gly Pro Val Tyr Val Ser Asp
                485                 490                 495

Ser Val Thr Leu Val Asn Val Ala Thr Gly Ala Gln Ala Val Ala Arg
            500                 505                 510

Ser Leu Asp Trp Thr Lys Val Thr Leu Asp Gly Arg Pro Leu Ser Thr
            515                 520                 525

Ile Gln Gln Tyr Ser Lys Thr Phe Phe Val Leu Pro Leu Arg Gly Lys
530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Leu Leu Val Glu Asn Ala Ala Gly
                565                 570                 575

His Arg Val Ala Ile Ser Thr Tyr Thr Thr Ser Leu Gly Ala Gly Pro
                580                 585                 590

Val Ser Ile Ser Ala Val Ala Val Leu Ala Pro His Ser Val Leu Ala
            595                 600                 605

Leu Leu Glu Asp Thr Met Asp Tyr Pro Ala Arg Ala His Thr Phe Asp
            610                 615                 620

Asp Phe Cys Pro Glu Cys Arg Pro Leu Gly Leu Gln Gly Cys Ala Phe
625                 630                 635                 640

Gln Ser Thr Val Ala Glu Leu Gln Arg Leu Lys Met Lys Val Gly Lys
                645                 650                 655

Thr Arg Glu Leu
            660

<210> SEQ ID NO 2
<211> LENGTH: 214
<212> TYPE: PRT
<213> ORGANISM: Hepatitis E virus

<400> SEQUENCE: 2

Met Gln Leu Phe Tyr Ser Arg Pro Val Val Ser Ala Asn Gly Glu Pro
1               5                   10                  15

Thr Val Lys Leu Tyr Thr Ser Val Glu Asn Ala Gln Gln Asp Lys Gly
            20                  25                  30

Ile Ala Ile Pro His Asp Ile Asp Leu Gly Glu Ser Arg Val Val Ile
            35                  40                  45

Gln Asp Tyr Asp Asn Gln His Glu Gln Asp Arg Pro Thr Pro Ser Pro
50                  55                  60

Ala Pro Ser Arg Pro Phe Ser Val Leu Arg Ala Asn Asp Val Leu Trp
65                  70                  75                  80

Leu Ser Leu Thr Ala Ala Glu Tyr Asp Gln Ser Thr Tyr Gly Ser Ser
                85                  90                  95

Thr Gly Pro Val Tyr Val Ser Asp Ser Val Thr Leu Val Asn Val Ala
            100                 105                 110

Thr Gly Ala Gln Ala Val Ala Arg Ser Leu Asp Trp Thr Lys Val Thr
            115                 120                 125

Leu Asp Gly Arg Pro Leu Ser Thr Ile Gln Gln Tyr Ser Lys Thr Phe
130                 135                 140

Phe Val Leu Pro Leu Arg Gly Lys Leu Ser Phe Trp Glu Ala Gly Thr
145                 150                 155                 160

Thr Lys Ala Gly Tyr Pro Tyr Asn Tyr Asn Thr Thr Ala Ser Asp Gln
                165                 170                 175

Leu Leu Val Glu Asn Ala Ala Gly His Arg Val Ala Ile Ser Thr Tyr
            180                 185                 190

Thr Thr Ser Leu Gly Ala Gly Pro Val Ser Ile Ser Ala Val Ala Val
            195                 200                 205

Leu Ala Pro Pro Arg
    210

<210> SEQ ID NO 3
<211> LENGTH: 194
<212> TYPE: PRT
<213> ORGANISM: Hepatitis E virus

<400> SEQUENCE: 3

Met Thr Ser Val Glu Asn Ala Gln Gln Asp Lys Gly Ile Ala Ile Pro
1               5                   10                  15

His Asp Ile Asp Leu Gly Glu Ser Arg Val Val Ile Gln Asp Tyr Asp
            20                  25                  30

Asn Gln His Glu Gln Asp Arg Pro Thr Pro Ser Pro Ala Pro Ser Arg
            35                  40                  45

Pro Phe Ser Val Leu Arg Ala Asn Asp Val Leu Trp Leu Ser Leu Thr
50                  55                  60

Ala Ala Glu Tyr Asp Gln Ser Thr Tyr Gly Ser Ser Thr Gly Pro Val
65                  70                  75                  80

Tyr Val Ser Asp Ser Val Thr Leu Val Asn Val Ala Thr Gly Ala Gln
                85                  90                  95

Ala Val Ala Arg Ser Leu Asp Trp Thr Lys Val Thr Leu Asp Gly Arg
            100                 105                 110

Pro Leu Ser Thr Ile Gln Gln Tyr Ser Lys Thr Phe Phe Val Leu Pro
            115                 120                 125

Leu Arg Gly Lys Leu Ser Phe Trp Glu Ala Gly Thr Thr Lys Ala Gly
130                 135                 140

Tyr Pro Tyr Asn Tyr Asn Thr Thr Ala Ser Asp Gln Leu Leu Val Glu
145                 150                 155                 160

Asn Ala Ala Gly His Arg Val Ala Ile Ser Thr Tyr Thr Thr Ser Leu
                165                 170                 175

Gly Ala Gly Pro Val Ser Ile Ser Ala Val Ala Val Leu Ala Pro Pro
            180                 185                 190

Pro Arg

<210> SEQ ID NO 4
<211> LENGTH: 389
<212> TYPE: PRT
<213> ORGANISM: Hepatitis E virus

<400> SEQUENCE: 4

Met Ala Ser Met Thr Gly Gly Gln Gln Met Gly Arg Gly Ser His Met
1               5                   10                  15

Asn Asn Met Ser Phe Ala Ala Pro Met Gly Ser Gln Pro Cys Ala Leu
                20                  25                  30

Gly Leu Phe Cys Cys Cys Ser Ser Cys Phe Cys Leu Cys Cys Pro Arg
            35                  40                  45

His Arg Pro Val Ser Arg Leu Ala Ala Val Val Gly Gly Ala Ala Ala
        50                  55                  60

Val Pro Ala Val Val Ser Gly Val Thr Gly Leu Ile Pro Ser Pro Ser
65                  70                  75                  80

Gln Ser Pro Ile Phe Ile Gln Pro Thr Pro Ser Pro Pro Met Ser Pro
                85                  90                  95

Leu Arg Pro Gly Leu Asp Leu Val Phe Ala Asn Pro Pro Asp His Ser
            100                 105                 110

Ala Pro Leu Gly Val Thr Arg Pro Ser Ala Pro Pro Leu Pro His Val
        115                 120                 125

Val Asp Leu Pro Gln Leu Gly Pro Arg Arg Gly Ser His Met Thr Ser
130                 135                 140

Val Glu Asn Ala Gln Gln Asp Lys Gly Ile Ala Ile Pro His Asp Ile
145                 150                 155                 160

Asp Leu Gly Glu Ser Arg Val Val Ile Gln Asp Tyr Asp Asn Gln His
                165                 170                 175

Glu Gln Asp Arg Pro Thr Pro Ser Pro Ala Pro Ser Arg Pro Phe Ser
            180                 185                 190

Val Leu Arg Ala Asn Asp Val Leu Trp Leu Ser Leu Thr Ala Ala Glu
        195                 200                 205

Tyr Asp Gln Ser Thr Tyr Gly Ser Ser Thr Gly Pro Val Tyr Val Ser
210                 215                 220

Asp Ser Val Thr Leu Val Asn Val Ala Thr Gly Ala Gln Ala Val Ala
225                 230                 235                 240

Arg Ser Leu Asp Trp Thr Lys Val Thr Leu Asp Gly Arg Pro Leu Ser
                245                 250                 255

Thr Ile Gln Gln Tyr Ser Lys Thr Phe Phe Val Leu Pro Leu Arg Gly
            260                 265                 270

Lys Leu Ser Phe Trp Glu Ala Gly Thr Thr Lys Ala Gly Tyr Pro Tyr
        275                 280                 285

Asn Tyr Asn Thr Thr Ala Ser Asp Gln Leu Leu Val Glu Asn Ala Ala
    290                 295                 300

Gly His Arg Val Ala Ile Ser Thr Tyr Thr Thr Ser Leu Gly Ala Gly
305                 310                 315                 320

Pro Val Ser Ile Ser Ala Val Ala Val Leu Ala Pro His Ser Ala Leu
                325                 330                 335

```
Ala Leu Leu Glu Asp Thr Met Asp Tyr Pro Ala Arg Ala His Thr Phe
            340                 345                 350

Asp Asp Phe Cys Pro Glu Cys Arg Pro Leu Gly Leu Gln Gly Cys Ala
        355                 360                 365

Phe Gln Ser Thr Val Ala Glu Leu Gln Arg Leu Lys Met Lys Val Gly
    370                 375                 380

Lys Thr Arg Glu Leu
385

<210> SEQ ID NO 5
<211> LENGTH: 1990
<212> TYPE: DNA
<213> ORGANISM: Hepatitis E virus

<400> SEQUENCE: 5
atgcgccctc ggcctatttt gctgttgctc ctcatgtttc tgcctatgct gcccgcgcca     60
ccgcccggtc agccgtctgg ccgccgtcgt gggcggcgca gcggcggttc cggcggtggt    120
ttctggggtg accgggttga ttctcagccc ttcgcaatcc cctatattca tccaaccaac    180
cccttcgccc ccgatgtcac cgctgcggcc ggggctggac ctcgtgttcg ccaacccgcc    240
cgaccactcg gctccgcttg gcgtgaccag gcccagcgcc ccgccgttgc ctcacgtcgt    300
agacctacca cagctggggc cgcgccgcta accgcggtcg ctccggccca tgacaccccg    360
ccagtgcctg atgttgactc ccgcggcgcc atcctgcgcc ggcagtataa cctatcaaca    420
tctcccctta cttcttccgt ggccaccggt acaaacttgg ttctatacgc cgctcctctt    480
agcccacttc tacccctcca ggacggcacc aatactcata taatggccac agaagcttct    540
aattatgccc agtaccgggt tgctcgtgcc acaattcgct accgcccgct ggtccccaac    600
gctgttggtg gctacgccat ctccatctcg ttctggccac agaccaccac caccccgacg    660
tccgttgaca tgaattcaat aacctcgacg gatgttcgta ttttagtcca gcccggcata    720
gcctccgagc ttgttatccc aagtgagcgc ctacactacc gtaaccaagg ttggcgctct    780
gttgagacct ccggggtggc ggaggaggag gccacctctg gtcttgttat gctctgcata    840
catggctcac ctgtaaattc ttatactaat acaccttata ccggtgccct cgggctgttg    900
gactttgccc tcgaacttga gttccgcaac ctcacccccg gtaataccaa cacgcgggtc    960
tcccgttact ccagcactgc ccgtcaccgc cttcgtcgcg gtgcagatgg gactgccgag   1020
cttaccacca cggctgctac ccgcttcatg aaggacctct attttactag tactaatggt   1080
gtcggtgaga tcggccgtgg gatagcgctt accctgttta accttgctga caccctgctt   1140
ggcggtctac cgacagaatt gatttcgtcg gctggtggcc agctgttcta ctctcgtccc   1200
gtcgtctcag ccaatggcga gccgactgtt aagctttata catctgtaga gaatgctcag   1260
caggataagg gtattgcaat cccgcatgac atcgacctcg gggagtctcg tgtagttatt   1320
caggattatg acaaccaaca tgagcaggac cgaccgacac cttccccagc cccatcgcgc   1380 ccttttttctg tcctccgagc taatgatgtg ctttggcttt ctctcaccgc tgccgagtat   1440
gaccagtcca cttacggctc ttcgaccggc ccagtctatg tctctgactc tgtgaccttg   1500
gttaatgttg cgaccggcgc gcaggccgtt gcccggtcac tcgactggac caaggtcaca   1560
cttgatggtc gcccccttttc caccatccag cagtattcaa agaccttctt tgtcctgccg   1620
ctccgcggta agctctcctt ttgggaggca ggtactacta aagccgggta cccttataat   1680
tataacacca ctgctagtga ccaactgctc gttgagaatg ccgctgggca tcgggttgct   1740
atttccactt acaccactag cctgggtgct ggtcccgtct ctatttccgc ggttgctgtt   1800
```

| | |
|---|---:|
| ttagcccccc actccgcgct agcattgctt gaggatacca tggactaccc tgcccgcgcc | 1860 |
| catactttcg atgacttctg cccggagtgc cgccccttg gcctccaggg ctgtgctttt | 1920 |
| cagtctactg tcgctgagct tcagcgcctt aagatgaagg tgggtaaaac tcgggagtta | 1980 |
| tagtttattt | 1990 |

<210> SEQ ID NO 6
<211> LENGTH: 1989
<212> TYPE: DNA
<213> ORGANISM: Hepatitis E virus

<400> SEQUENCE: 6

| | |
|---|---:|
| atgcgccctc ggcctatttt gctgttgctc ctcatgtttc tgcctatgct gcccgcgcca | 60 |
| ccgcccggtc agccgtctgg ccgccgtcgt gggcggcgca cggcggttc cggcggtggt | 120 |
| ttctggggtg accgggttga ttctcagccc ttcgcaatcc cctatattca tccaaccaac | 180 |
| cccttcgccc ccgatgtcac cgctgcggcc ggggctggac ctcgtgttcg ccaacccgcc | 240 |
| cgaccactcg gctccgcttg gcgtgaccag gcccagcgcc ccgccgttgc ctcacgtcgt | 300 |
| agacctacca cagctggggc cgcgccgcta accgcggtcg ctccggccca tgacaccccg | 360 |
| ccagtgcctg atgttgactc ccgcggcgcc atcctgcgcc ggcagtataa cctatcaaca | 420 |
| tctccccttta cttcttccgt ggccaccggt acaaacttgg ttctatacgc cgctcctctt | 480 |
| agcccacttc tacccctcca ggacggcacc aatactcata taatggccac agaagcttct | 540 |
| aattatgccc agtaccgggt tgctcgtgcc acaattcgct accgccgct ggtccccaac | 600 |
| gctgttggtg gctacgccat ctccatctcg ttctggccac agaccaccac cacccccgacg | 660 |
| tccgttgaca tgaattcaat aacctcgacg gatgttcgta ttttagtcca gcccggcata | 720 |
| gcctccgagc ttgttatccc aagtgagcgc ctacactacc gtaaccaagg ttggcgctct | 780 |
| gttgagacct ccggggtggc ggaggaggag gccacctctg tcttgttat gctctgcata | 840 |
| catggctcac ctgtaaattc ttatactaat acaccttata ccggtgccct cgggctgttg | 900 |
| gactttgccc tcgaacttga gttccgcaac ctcacccccg gtaataccaa cacgcgggtc | 960 |
| tcccgttact ccagcactgc ccgtcaccgc cttcgtcgcg gtgcagatgg gactgccgag | 1020 |
| cttaccacca cggctgctac ccgcttcatg aaggacctct atttactag tactaatggt | 1080 |
| gtcggtgaga tcggccgtgg gatagcgctt accctgttta accttgctga cccctgctt | 1140 |
| ggcggtctac cgacagaatt gatttcgtcg gctggtggcc agctgttcta ctctcgtccc | 1200 |
| gtcgtctcag ccaatggcga gccgactgtt aagctttata catctgtaga gaatgctcag | 1260 |
| caggataagg gtattgcaat cccgcatgac atcgacctcg gggagtctcg tgtagttatt | 1320 |
| caggattatg acaaccaaca tgagcaggac cgaccgacac cttccccagc ccatcgcgc | 1380 |
| ccttttttctg tcctccgagc taatgatgtg ctttggcttt ctctcaccgc tgccgagtat | 1440 |
| gaccagtcca cttacggctc ttcgaccggc ccagtctatg tctctgactc tgtgaccttg | 1500 |
| gttaatgttg cgaccggcgc gcaggccgtt gcccggtcac tcgactggac caaggtcaca | 1560 |
| cttgatggtc gccccctttc caccatccag cagtattcaa agaccttctt tgtcctgccg | 1620 |
| ctccgcggta agctctcctt tgggaggca ggtactacta agccgggta cccttataat | 1680 |
| tataaccaca ctgctagtga ccaactgctc gttgagaatg ccgctgggca tcgggttgct | 1740 |
| atttccactt acaccactag cctgggtgct ggtcccgtct ctatttccgc ggttgctgtt | 1800 |
| ttagcccccc ctccgcgcta gcattgcttg aggatacat ggactaccct gcccgcgccc | 1860 |
| atactttcga tgacttctgc ccggagtgcc gccccttgg cctccaggc tgtgctttc | 1920 |

```
agtctactgt cgctgagctt cagcgcctta agatgaaggt gggtaaaact cgggagttat    1980
agtttatttt                                                            1989
```

<210> SEQ ID NO 7
<211> LENGTH: 169
<212> TYPE: PRT
<213> ORGANISM: Hepatitis E virus

<400> SEQUENCE: 7

```
Met Val Ile Gln Asp Tyr Asp Asn Gln His Glu Gln Asp Arg Pro Thr
1               5                   10                  15

Pro Ser Pro Ala Pro Ser Arg Pro Phe Ser Val Leu Arg Ala Asn Asp
            20                  25                  30

Val Leu Trp Leu Ser Leu Thr Ala Ala Glu Tyr Asp Gln Ser Thr Tyr
        35                  40                  45

Gly Ser Ser Thr Gly Pro Val Tyr Val Ser Asp Ser Val Thr Leu Val
    50                  55                  60

Asn Val Ala Thr Gly Ala Gln Ala Val Ala Arg Ser Leu Asp Trp Thr
65                  70                  75                  80

Lys Val Thr Leu Asp Gly Arg Pro Leu Ser Thr Ile Gln Gln Tyr Ser
                85                  90                  95

Lys Thr Phe Phe Val Leu Pro Leu Arg Gly Lys Leu Ser Phe Trp Glu
            100                 105                 110

Ala Gly Thr Thr Lys Ala Gly Tyr Pro Tyr Asn Tyr Asn Thr Thr Ala
        115                 120                 125

Ser Asp Gln Leu Leu Val Glu Asn Ala Ala Gly His Arg Val Ala Ile
    130                 135                 140

Ser Thr Tyr Thr Thr Ser Leu Gly Ala Gly Pro Val Ser Ile Ser Ala
145                 150                 155                 160

Val Ala Val Leu Ala Pro Pro Arg
                165
```

<210> SEQ ID NO 8
<211> LENGTH: 159
<212> TYPE: PRT
<213> ORGANISM: Hepatitis E virus

<400> SEQUENCE: 8

```
Met Gln Asp Arg Pro Thr Pro Ser Pro Ala Pro Ser Arg Pro Phe Ser
1               5                   10                  15

Val Leu Arg Ala Asn Asp Val Leu Trp Leu Ser Leu Thr Ala Ala Glu
            20                  25                  30

Tyr Asp Gln Ser Thr Tyr Gly Ser Ser Thr Gly Pro Val Tyr Val Ser
        35                  40                  45

Asp Ser Val Thr Leu Val Asn Val Ala Thr Gly Ala Gln Ala Val Ala
    50                  55                  60

Arg Ser Leu Asp Trp Thr Lys Val Thr Leu Asp Gly Arg Pro Leu Ser
65                  70                  75                  80

Thr Ile Gln Gln Tyr Ser Lys Thr Phe Phe Val Leu Pro Leu Arg Gly
                85                  90                  95

Lys Leu Ser Phe Trp Glu Ala Gly Thr Thr Lys Ala Gly Tyr Pro Tyr
            100                 105                 110

Asn Tyr Asn Thr Thr Ala Ser Asp Gln Leu Leu Val Glu Asn Ala Ala
        115                 120                 125

Gly His Arg Val Ala Ile Ser Thr Tyr Thr Thr Ser Leu Gly Ala Gly
    130                 135                 140
```

Pro Val Ser Ile Ser Ala Val Ala Val Leu Ala Pro Pro Arg
145                 150                 155

<210> SEQ ID NO 9
<211> LENGTH: 149
<212> TYPE: PRT
<213> ORGANISM: Hepatitis E virus

<400> SEQUENCE: 9

Met Ser Arg Pro Phe Ser Val Leu Arg Ala Asn Asp Val Leu Trp Leu
1               5                   10                  15

Ser Leu Thr Ala Ala Glu Tyr Asp Gln Ser Thr Tyr Gly Ser Ser Thr
            20                  25                  30

Gly Pro Val Tyr Val Ser Asp Ser Val Thr Leu Val Asn Val Ala Thr
        35                  40                  45

Gly Ala Gln Ala Val Ala Arg Ser Leu Asp Trp Thr Lys Val Thr Leu
    50                  55                  60

Asp Gly Arg Pro Leu Ser Thr Ile Gln Gln Tyr Ser Lys Thr Phe Phe
65                  70                  75                  80

Val Leu Pro Leu Arg Gly Lys Leu Ser Phe Trp Glu Ala Gly Thr Thr
                85                  90                  95

Lys Ala Gly Tyr Pro Tyr Asn Tyr Asn Thr Thr Ala Ser Asp Gln Leu
            100                 105                 110

Leu Val Glu Asn Ala Ala Gly His Arg Val Ala Ile Ser Thr Tyr Thr
        115                 120                 125

Thr Ser Leu Gly Ala Gly Pro Val Ser Ile Ser Ala Val Ala Val Leu
    130                 135                 140

Ala Pro Pro Arg
145

<210> SEQ ID NO 10
<211> LENGTH: 139
<212> TYPE: PRT
<213> ORGANISM: Hepatitis E virus

<400> SEQUENCE: 10

Met Asp Val Leu Trp Leu Ser Leu Thr Ala Ala Glu Tyr Asp Gln Ser
1               5                   10                  15

Thr Tyr Gly Ser Ser Thr Gly Pro Val Tyr Val Ser Asp Ser Val Thr
            20                  25                  30

Leu Val Asn Val Ala Thr Gly Ala Gln Ala Val Ala Arg Ser Leu Asp
        35                  40                  45

Trp Thr Lys Val Thr Leu Asp Gly Arg Pro Leu Ser Thr Ile Gln Gln
    50                  55                  60

Tyr Ser Lys Thr Phe Phe Val Leu Pro Leu Arg Gly Lys Leu Ser Phe
65                  70                  75                  80

Trp Glu Ala Gly Thr Thr Lys Ala Gly Tyr Pro Tyr Asn Tyr Asn Thr
                85                  90                  95

Thr Ala Ser Asp Gln Leu Leu Val Glu Asn Ala Ala Gly His Arg Val
            100                 105                 110

Ala Ile Ser Thr Tyr Thr Thr Ser Leu Gly Ala Gly Pro Val Ser Ile
        115                 120                 125

Ser Ala Val Ala Val Leu Ala Pro Pro Arg
    130                 135

<210> SEQ ID NO 11
<211> LENGTH: 123
<212> TYPE: PRT

<213> ORGANISM: Hepatitis E virus

<400> SEQUENCE: 11

Met Asn Asn Met Ser Phe Ala Ala Pro Met Gly Ser Arg Pro Cys Ala
1               5                   10                  15

Leu Gly Leu Phe Cys Cys Cys Ser Ser Cys Phe Cys Leu Cys Cys Pro
            20                  25                  30

Arg His Arg Pro Val Ser Arg Leu Ala Ala Val Val Gly Gly Ala Ala
        35                  40                  45

Ala Val Pro Ala Val Val Ser Gly Val Thr Gly Leu Ile Leu Ser Pro
    50                  55                  60

Ser Gln Ser Pro Ile Phe Ile Gln Pro Thr Pro Ser Pro Pro Met Ser
65                  70                  75                  80

Pro Leu Arg Pro Gly Leu Asp Leu Val Phe Ala Asn Pro Pro Asp His
                85                  90                  95

Ser Ala Pro Leu Gly Val Thr Arg Pro Ser Ala Pro Pro Leu Pro His
            100                 105                 110

Val Val Asp Leu Pro Gln Leu Gly Pro Arg Arg
        115                 120

<210> SEQ ID NO 12
<211> LENGTH: 232
<212> TYPE: PRT
<213> ORGANISM: Hepatitis E virus

<400> SEQUENCE: 12

Met Ser Lys Ala Phe Ser Asn Cys Tyr Pro Tyr Asp Val Pro Asp Tyr
1               5                   10                  15

Ala Ser Leu Gly Gly Ser Gln Leu Phe Tyr Ser Arg Pro Val Val Ser
            20                  25                  30

Ala Asn Gly Glu Pro Thr Val Lys Leu Tyr Thr Ser Val Glu Asn Ala
        35                  40                  45

Gln Gln Asp Lys Gly Ile Ala Ile Pro His Asp Ile Asp Leu Gly Glu
    50                  55                  60

Ser Arg Val Val Ile Gln Asp Tyr Asp Asn Gln His Glu Gln Asp Arg
65                  70                  75                  80

Pro Thr Pro Ser Pro Ala Pro Ser Arg Pro Phe Ser Val Leu Arg Ala
                85                  90                  95

Asn Asp Val Leu Trp Leu Ser Leu Thr Ala Ala Glu Tyr Asp Gln Ser
            100                 105                 110

Thr Tyr Gly Ser Ser Thr Gly Pro Val Tyr Val Ser Asp Ser Val Thr
        115                 120                 125

Leu Val Asn Val Ala Thr Gly Ala Gln Ala Val Ala Arg Ser Leu Asp
    130                 135                 140

Trp Thr Lys Val Thr Leu Asp Gly Arg Pro Leu Ser Thr Ile Gln Gln
145                 150                 155                 160

Tyr Ser Lys Thr Phe Phe Val Leu Pro Leu Arg Gly Lys Leu Ser Phe
                165                 170                 175

Trp Glu Ala Gly Thr Thr Lys Ala Gly Tyr Pro Tyr Asn Tyr Asn Thr
            180                 185                 190

Thr Ala Ser Asp Gln Leu Leu Val Glu Asn Ala Ala Gly His Arg Val
        195                 200                 205

Ala Ile Ser Thr Tyr Thr Thr Ser Leu Gly Ala Gly Pro Val Ser Ile
    210                 215                 220

Ser Ala Val Ala Val Leu Ala Pro
225                 230

<210> SEQ ID NO 13
<211> LENGTH: 15
<212> TYPE: DNA
<213> ORGANISM: Artificial
<220> FEATURE:
<223> OTHER INFORMATION: Primer

<400> SEQUENCE: 13
atgcgccctc ggcca                                                         15

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
aaataaacta taactcccga                                                    20

<210> SEQ ID NO 15
<211> LENGTH: 30
<212> TYPE: DNA
<213> ORGANISM: Artificial
<220> FEATURE:
<223> OTHER INFORMATION: Primer

<400> SEQUENCE: 15
ggatcccata tggttattca ggattatgac                                         30

<210> SEQ ID NO 16
<211> LENGTH: 26
<212> TYPE: DNA
<213> ORGANISM: Artificial
<220> FEATURE:
<223> OTHER INFORMATION: Primer

<400> SEQUENCE: 16
ctcgagaaat aaactataac tcccga                                             26

<210> SEQ ID NO 17
<211> LENGTH: 30
<212> TYPE: DNA
<213> ORGANISM: Artificial
<220> FEATURE:
<223> OTHER INFORMATION: Primer

<400> SEQUENCE: 17
ggatccatat gcagctgttc tactctcgtc                                         30

<210> SEQ ID NO 18
<211> LENGTH: 27
<212> TYPE: DNA
<213> ORGANISM: Artificial
<220> FEATURE:
<223> OTHER INFORMATION: Primer

<400> SEQUENCE: 18
ggatcccata tgtcggctgg tggccag                                            27

<210> SEQ ID NO 19
<211> LENGTH: 32
<212> TYPE: DNA
<213> ORGANISM: Artificial
<220> FEATURE:
<223> OTHER INFORMATION: Primer

```
<400> SEQUENCE: 19
ggatcccata tgacatctgt agagaatgct ca                          32

<210> SEQ ID NO 20
<211> LENGTH: 28
<212> TYPE: DNA
<213> ORGANISM: Artificial
<220> FEATURE:
<223> OTHER INFORMATION: Primer

<400> SEQUENCE: 20
ggatcccata tgcatgacat cgacctcg                               28

<210> SEQ ID NO 21
<211> LENGTH: 26
<212> TYPE: DNA
<213> ORGANISM: Artificial
<220> FEATURE:
<223> OTHER INFORMATION: Primer

<400> SEQUENCE: 21
ggatcccata tgcaggaccg accgac                                 26

<210> SEQ ID NO 22
<211> LENGTH: 31
<212> TYPE: DNA
<213> ORGANISM: Artificial
<220> FEATURE:
<223> OTHER INFORMATION: Primer

<400> SEQUENCE: 22
ggatcccata tggacgtgct ttggctttct c                           31

<210> SEQ ID NO 23
<211> LENGTH: 30
<212> TYPE: DNA
<213> ORGANISM: Artificial
<220> FEATURE:
<223> OTHER INFORMATION: Primer

<400> SEQUENCE: 23
ggatccatat gcagctgttc tactctcgtc                             30

<210> SEQ ID NO 24
<211> LENGTH: 24
<212> TYPE: DNA
<213> ORGANISM: Artificial
<220> FEATURE:
<223> OTHER INFORMATION: Primer

<400> SEQUENCE: 24
gaattcttag ggggctaaaa cagc                                   24

<210> SEQ ID NO 25
<211> LENGTH: 27
<212> TYPE: DNA
<213> ORGANISM: Artificial
<220> FEATURE:
<223> OTHER INFORMATION: Primer

<400> SEQUENCE: 25
ggatcccata tgtcggctgg tggccag                                27

<210> SEQ ID NO 26
<211> LENGTH: 24
```

```
<212> TYPE: DNA
<213> ORGANISM: Artificial
<220> FEATURE:
<223> OTHER INFORMATION: Primer

<400> SEQUENCE: 26
gaattcttag ggggctaaaa cagc                                              24

<210> SEQ ID NO 27
<211> LENGTH: 32
<212> TYPE: DNA
<213> ORGANISM: Artificial
<220> FEATURE:
<223> OTHER INFORMATION: Primer

<400> SEQUENCE: 27
ggatcccata tgacatctgt agagaatgct ca                                     32

<210> SEQ ID NO 28
<211> LENGTH: 24
<212> TYPE: DNA
<213> ORGANISM: Artificial
<220> FEATURE:
<223> OTHER INFORMATION: Primer

<400> SEQUENCE: 28
gaattcttag ggggctaaaa cagc                                              24

<210> SEQ ID NO 29
<211> LENGTH: 28
<212> TYPE: DNA
<213> ORGANISM: Artificial
<220> FEATURE:
<223> OTHER INFORMATION: Primer

<400> SEQUENCE: 29
ggatcccata tgcatgacat cgacctcg                                          28

<210> SEQ ID NO 30
<211> LENGTH: 24
<212> TYPE: DNA
<213> ORGANISM: Artificial
<220> FEATURE:
<223> OTHER INFORMATION: Primer

<400> SEQUENCE: 30
gaattcttag ggggctaaaa cagc                                              24

<210> SEQ ID NO 31
<211> LENGTH: 30
<212> TYPE: DNA
<213> ORGANISM: Artificial
<220> FEATURE:
<223> OTHER INFORMATION: Primer

<400> SEQUENCE: 31
ggatccatat gcagctgttc tactctcgtc                                        30

<210> SEQ ID NO 32
<211> LENGTH: 32
<212> TYPE: DNA
<213> ORGANISM: Artificial
<220> FEATURE:
<223> OTHER INFORMATION: Primer

<400> SEQUENCE: 32
gaattcttat gcggaatggg gggctaaaac ag                                     32
```

<210> SEQ ID NO 33
<211> LENGTH: 27
<212> TYPE: DNA
<213> ORGANISM: Artificial
<220> FEATURE:
<223> OTHER INFORMATION: Primer

<400> SEQUENCE: 33
ggatcccata tgtcggctgg tggccag                                    27

<210> SEQ ID NO 34
<211> LENGTH: 32
<212> TYPE: DNA
<213> ORGANISM: Artificial
<220> FEATURE:
<223> OTHER INFORMATION: Primer

<400> SEQUENCE: 34
gaattcttat gcggaatggg gggctaaaac ag                              32

<210> SEQ ID NO 35
<211> LENGTH: 32
<212> TYPE: DNA
<213> ORGANISM: Artificial
<220> FEATURE:
<223> OTHER INFORMATION: Primer

<400> SEQUENCE: 35
ggatcccata tgacatctgt agagaatgct ca                              32

<210> SEQ ID NO 36
<211> LENGTH: 32
<212> TYPE: DNA
<213> ORGANISM: Artificial
<220> FEATURE:
<223> OTHER INFORMATION: Primer

<400> SEQUENCE: 36
gaattcttat gcggaatggg gggctaaaac ag                              32

<210> SEQ ID NO 37
<211> LENGTH: 28
<212> TYPE: DNA
<213> ORGANISM: Artificial
<220> FEATURE:
<223> OTHER INFORMATION: Primer

<400> SEQUENCE: 37
ggatcccata tgcatgacat cgacctcg                                   28

<210> SEQ ID NO 38
<211> LENGTH: 32
<212> TYPE: DNA
<213> ORGANISM: Artificial
<220> FEATURE:
<223> OTHER INFORMATION: Primer

<400> SEQUENCE: 38
gaattcttat gcggaatggg gggctaaaac ag                              32

<210> SEQ ID NO 39
<211> LENGTH: 30
<212> TYPE: DNA
<213> ORGANISM: Artificial
<220> FEATURE:
<223> OTHER INFORMATION: Primer

```
<400> SEQUENCE: 39
ggatccatat gcagctgttc tactctcgtc                                              30

<210> SEQ ID NO 40
<211> LENGTH: 30
<212> TYPE: DNA
<213> ORGANISM: Artificial
<220> FEATURE:
<223> OTHER INFORMATION: Primer

<400> SEQUENCE: 40
ggatccatat gcagctgttc tactctcgtc                                              30

<210> SEQ ID NO 41
<211> LENGTH: 25
<212> TYPE: DNA
<213> ORGANISM: Artificial
<220> FEATURE:
<223> OTHER INFORMATION: Primer

<400> SEQUENCE: 41
gaattcttac gggcagaagt catcg                                                   25

<210> SEQ ID NO 42
<211> LENGTH: 30
<212> TYPE: DNA
<213> ORGANISM: Artificial
<220> FEATURE:
<223> OTHER INFORMATION: Primer

<400> SEQUENCE: 42
ggatccatat gcagctgttc tactctcgtc                                              30

<210> SEQ ID NO 43
<211> LENGTH: 26
<212> TYPE: DNA
<213> ORGANISM: Artificial
<220> FEATURE:
<223> OTHER INFORMATION: Primer

<400> SEQUENCE: 43
gaattcttag gcagggtagt ccatgg                                                  26

<210> SEQ ID NO 44
<211> LENGTH: 30
<212> TYPE: DNA
<213> ORGANISM: Artificial
<220> FEATURE:
<223> OTHER INFORMATION: Primer

<400> SEQUENCE: 44
ggatccatat gcagctgttc tactctcgtc                                              30

<210> SEQ ID NO 45
<211> LENGTH: 25
<212> TYPE: DNA
<213> ORGANISM: Artificial
<220> FEATURE:
<223> OTHER INFORMATION: Primer

<400> SEQUENCE: 45
gaattcttag gctaaaacag caacc                                                   25

<210> SEQ ID NO 46
<211> LENGTH: 30
```

```
<212> TYPE: DNA
<213> ORGANISM: Artificial
<220> FEATURE:
<223> OTHER INFORMATION: Primer

<400> SEQUENCE: 46
ggatccatat gcagctgttc tactctcgtc                                          30

<210> SEQ ID NO 47
<211> LENGTH: 24
<212> TYPE: DNA
<213> ORGANISM: Artificial
<220> FEATURE:
<223> OTHER INFORMATION: Primer

<400> SEQUENCE: 47
gaattcttat aaaacagcaa ccgc                                                24

<210> SEQ ID NO 48
<211> LENGTH: 30
<212> TYPE: DNA
<213> ORGANISM: Artificial
<220> FEATURE:
<223> OTHER INFORMATION: Primer

<400> SEQUENCE: 48
ggatccatat gcagctgttc tactctcgtc                                          30

<210> SEQ ID NO 49
<211> LENGTH: 30
<212> TYPE: DNA
<213> ORGANISM: Artificial
<220> FEATURE:
<223> OTHER INFORMATION: Primer

<400> SEQUENCE: 49
ggatccatat gcagctgttc tactctcgtc                                          30

<210> SEQ ID NO 50
<211> LENGTH: 26
<212> TYPE: DNA
<213> ORGANISM: Artificial
<220> FEATURE:
<223> OTHER INFORMATION: Primer

<400> SEQUENCE: 50
gaattcttag gaaatagaga cgggac                                              26

<210> SEQ ID NO 51
<211> LENGTH: 30
<212> TYPE: DNA
<213> ORGANISM: Artificial
<220> FEATURE:
<223> OTHER INFORMATION: Primer

<400> SEQUENCE: 51
ggatccatat gcagctgttc tactctcgtc                                          30

<210> SEQ ID NO 52
<211> LENGTH: 29
<212> TYPE: DNA
<213> ORGANISM: Artificial
<220> FEATURE:
<223> OTHER INFORMATION: Primer

<400> SEQUENCE: 52
ctcgagttaa gtggtgtaag tggaaatag                                           29
```

<210> SEQ ID NO 53
<211> LENGTH: 30
<212> TYPE: DNA
<213> ORGANISM: Artificial
<220> FEATURE:
<223> OTHER INFORMATION: Primer

<400> SEQUENCE: 53
ggatccatat gcagctgttc tactctcgtc        30

<210> SEQ ID NO 54
<211> LENGTH: 27
<212> TYPE: DNA
<213> ORGANISM: Artificial
<220> FEATURE:
<223> OTHER INFORMATION: Primer

<400> SEQUENCE: 54
ctcgagttac agttggtcac tagcagt            27

<210> SEQ ID NO 55
<211> LENGTH: 28
<212> TYPE: DNA
<213> ORGANISM: Artificial
<220> FEATURE:
<223> OTHER INFORMATION: Primer

<400> SEQUENCE: 55
ggatcccata tgctaggcgg tctaccca           28

<210> SEQ ID NO 56
<211> LENGTH: 27
<212> TYPE: DNA
<213> ORGANISM: Artificial
<220> FEATURE:
<223> OTHER INFORMATION: Primer

<400> SEQUENCE: 56
ggatcccata tgtcggctgg tggccag            27

<210> SEQ ID NO 57
<211> LENGTH: 26
<212> TYPE: DNA
<213> ORGANISM: Artificial
<220> FEATURE:
<223> OTHER INFORMATION: Primer

<400> SEQUENCE: 57
ggatcccata tgcccgtcgt ctcagc             26

<210> SEQ ID NO 58
<211> LENGTH: 32
<212> TYPE: DNA
<213> ORGANISM: Artificial
<220> FEATURE:
<223> OTHER INFORMATION: Primer

<400> SEQUENCE: 58
ggatcccata tgacatctgt agagaatgct ca      32

<210> SEQ ID NO 59
<211> LENGTH: 28
<212> TYPE: DNA
<213> ORGANISM: Artificial
<220> FEATURE:
<223> OTHER INFORMATION: Primer

```
<400> SEQUENCE: 59
ggatcccata tgcatgacat cgacctcg                                          28

<210> SEQ ID NO 60
<211> LENGTH: 32
<212> TYPE: DNA
<213> ORGANISM: Artificial
<220> FEATURE:
<223> OTHER INFORMATION: Primer

<400> SEQUENCE: 60
ggatcccata tgacatctgt agagaatgct ca                                     32

<210> SEQ ID NO 61
<211> LENGTH: 26
<212> TYPE: DNA
<213> ORGANISM: Artificial
<220> FEATURE:
<223> OTHER INFORMATION: Primer

<400> SEQUENCE: 61
gaattcttag gcagggtagt ccatgg                                            26

<210> SEQ ID NO 62
<211> LENGTH: 31
<212> TYPE: DNA
<213> ORGANISM: Artificial
<220> FEATURE:
<223> OTHER INFORMATION: Primer

<400> SEQUENCE: 62
ggatcccata tggacgtgct ttggctttct c                                      31

<210> SEQ ID NO 63
<211> LENGTH: 32
<212> TYPE: DNA
<213> ORGANISM: Artificial
<220> FEATURE:
<223> OTHER INFORMATION: Primer

<400> SEQUENCE: 63
ggatcccata tgacatctgt agagaatgct ca                                     32

<210> SEQ ID NO 64
<211> LENGTH: 25
<212> TYPE: DNA
<213> ORGANISM: Artificial
<220> FEATURE:
<223> OTHER INFORMATION: Primer

<400> SEQUENCE: 64
gaattcttag gctaaaacag caacc                                             25

<210> SEQ ID NO 65
<211> LENGTH: 32
<212> TYPE: DNA
<213> ORGANISM: Artificial
<220> FEATURE:
<223> OTHER INFORMATION: Primer

<400> SEQUENCE: 65
ggatcccata tgacatctgt agagaatgct ca                                     32

<210> SEQ ID NO 66
<211> LENGTH: 24
```

-continued

```
<212> TYPE: DNA
<213> ORGANISM: Artificial
<220> FEATURE:
<223> OTHER INFORMATION: Primer

<400> SEQUENCE: 66
gaattcttat aaaacagcaa ccgc                                           24

<210> SEQ ID NO 67
<211> LENGTH: 32
<212> TYPE: DNA
<213> ORGANISM: Artificial
<220> FEATURE:
<223> OTHER INFORMATION: Primer

<400> SEQUENCE: 67
ggatcccata tgacatctgt agagaatgct ca                                  32

<210> SEQ ID NO 68
<211> LENGTH: 26
<212> TYPE: DNA
<213> ORGANISM: Artificial
<220> FEATURE:
<223> OTHER INFORMATION: Primer

<400> SEQUENCE: 68
gaattcttag gaaatagaga cgggac                                         26

<210> SEQ ID NO 69
<211> LENGTH: 32
<212> TYPE: DNA
<213> ORGANISM: Artificial
<220> FEATURE:
<223> OTHER INFORMATION: Primer

<400> SEQUENCE: 69
ggatcccata tgacatctgt agagaatgct ca                                  32

<210> SEQ ID NO 70
<211> LENGTH: 29
<212> TYPE: DNA
<213> ORGANISM: Artificial
<220> FEATURE:
<223> OTHER INFORMATION: Primer

<400> SEQUENCE: 70
ctcgagttaa gtggtgtaag tggaaatag                                      29

<210> SEQ ID NO 71
<211> LENGTH: 25
<212> TYPE: DNA
<213> ORGANISM: Artificial
<220> FEATURE:
<223> OTHER INFORMATION: Primer

<400> SEQUENCE: 71
gaattcttac gggcagaagt catcg                                          25

<210> SEQ ID NO 72
<211> LENGTH: 31
<212> TYPE: DNA
<213> ORGANISM: Artificial
<220> FEATURE:
<223> OTHER INFORMATION: Primer

<400> SEQUENCE: 72
ggatcccata tggacgtgct ttggctttct c                                   31
```

<210> SEQ ID NO 73
<211> LENGTH: 25
<212> TYPE: DNA
<213> ORGANISM: Artificial
<220> FEATURE:
<223> OTHER INFORMATION: Primer

<400> SEQUENCE: 73
gaattcttac gggcagaagt catcg                                          25

<210> SEQ ID NO 74
<211> LENGTH: 26
<212> TYPE: DNA
<213> ORGANISM: Artificial
<220> FEATURE:
<223> OTHER INFORMATION: Primer

<400> SEQUENCE: 74
gaattcttag gcagggtagt ccatgg                                         26

<210> SEQ ID NO 75
<211> LENGTH: 31
<212> TYPE: DNA
<213> ORGANISM: Artificial
<220> FEATURE:
<223> OTHER INFORMATION: Primer

<400> SEQUENCE: 75
ggatcccata tggacgtgct ttggctttct c                                   31

<210> SEQ ID NO 76
<211> LENGTH: 26
<212> TYPE: DNA
<213> ORGANISM: Artificial
<220> FEATURE:
<223> OTHER INFORMATION: Primer

<400> SEQUENCE: 76
gaattcttag gcagggtagt ccatgg                                         26

<210> SEQ ID NO 77
<211> LENGTH: 25
<212> TYPE: DNA
<213> ORGANISM: Artificial
<220> FEATURE:
<223> OTHER INFORMATION: Primer

<400> SEQUENCE: 77
gaattcttag gctaaaacag caacc                                          25

<210> SEQ ID NO 78
<211> LENGTH: 31
<212> TYPE: DNA
<213> ORGANISM: Artificial
<220> FEATURE:
<223> OTHER INFORMATION: Primer

<400> SEQUENCE: 78
ggatcccata tggacgtgct ttggctttct c                                   31

<210> SEQ ID NO 79
<211> LENGTH: 25
<212> TYPE: DNA
<213> ORGANISM: Artificial
<220> FEATURE:
<223> OTHER INFORMATION: Primer

```
<400> SEQUENCE: 79
gaattcttag gctaaaacag caacc                                            25

<210> SEQ ID NO 80
<211> LENGTH: 21
<212> TYPE: DNA
<213> ORGANISM: Artificial
<220> FEATURE:
<223> OTHER INFORMATION: Primer

<400> SEQUENCE: 80
ggctcaccgg agtgtttctt c                                                21

<210> SEQ ID NO 81
<211> LENGTH: 22
<212> TYPE: DNA
<213> ORGANISM: Artificial
<220> FEATURE:
<223> OTHER INFORMATION: Primer

<400> SEQUENCE: 81
ctttgatgac accgtcttct cg                                               22

<210> SEQ ID NO 82
<211> LENGTH: 21
<212> TYPE: DNA
<213> ORGANISM: Artificial
<220> FEATURE:
<223> OTHER INFORMATION: Primer

<400> SEQUENCE: 82
gccgcagcaa aggcatccat g                                                21

<210> SEQ ID NO 83
<211> LENGTH: 22
<212> TYPE: DNA
<213> ORGANISM: Artificial
<220> FEATURE:
<223> OTHER INFORMATION: Primer

<400> SEQUENCE: 83
gtgtttcttc caaaccctc gc                                                22

<210> SEQ ID NO 84
<211> LENGTH: 30
<212> TYPE: DNA
<213> ORGANISM: Artificial
<220> FEATURE:
<223> OTHER INFORMATION: Primer

<400> SEQUENCE: 84
ggatcccata tgaataacat gtcttttgct                                       30

<210> SEQ ID NO 85
<211> LENGTH: 17
<212> TYPE: DNA
<213> ORGANISM: Artificial
<220> FEATURE:
<223> OTHER INFORMATION: Primer

<400> SEQUENCE: 85
ggatcctcgg cgcggcc                                                     17

<210> SEQ ID NO 86
<211> LENGTH: 3
```

```
<212> TYPE: PRT
<213> ORGANISM: Artificial
<220> FEATURE:
<223> OTHER INFORMATION: Primer

<400> SEQUENCE: 86

Gly Gly Ser
1

<210> SEQ ID NO 87
<211> LENGTH: 9
<212> TYPE: DNA
<213> ORGANISM: Artificial
<220> FEATURE:
<223> OTHER INFORMATION: Primer

<400> SEQUENCE: 87 cagctgttc                                                                  9

<210> SEQ ID NO 88
<211> LENGTH: 21
<212> TYPE: PRT
<213> ORGANISM: Artificial
<220> FEATURE:
<223> OTHER INFORMATION: Primer

<400> SEQUENCE: 88

Ser Lys Ala Phe Ser Asn Cys Tyr Pro Tyr Asp Val Pro Asp Tyr Ala
1               5                   10                  15

Ser Leu Gly Gly Ser
            20

<210> SEQ ID NO 89
<211> LENGTH: 95
<212> TYPE: DNA
<213> ORGANISM: Artificial
<220> FEATURE:
<223> OTHER INFORMATION: Primer

<400> SEQUENCE: 89
agatctcata tgtctaaagc tttctctaac tgctacccett acgacgttcc ggactacgct         60
tctttaggtg gatcccagct gttctactct cgtcc                                    95

<210> SEQ ID NO 90
<211> LENGTH: 24
<212> TYPE: DNA
<213> ORGANISM: Artificial
<220> FEATURE:
<223> OTHER INFORMATION: Primer

<400> SEQUENCE: 90
gaattcttag ggggctaaaa cagc                                                24

<210> SEQ ID NO 91
<211> LENGTH: 25
<212> TYPE: DNA
<213> ORGANISM: Artificial
<220> FEATURE:
<223> OTHER INFORMATION: Primer

<400> SEQUENCE: 91
ggatcccata tgtcgcgccc ttttt                                               25

<210> SEQ ID NO 92
<211> LENGTH: 22
<212> TYPE: DNA
```

```
<213> ORGANISM: Artificial
<220> FEATURE:
<223> OTHER INFORMATION: Primer

<400> SEQUENCE: 92
gaattcttaa acagcaaccg cg                                          22
```

POLYPEPTIDE FRAGMENTS OF THE HEPATITIS E VIRUS, THE VACCINE COMPOSITION COMPRISING SAID FRAGMENTS AND THE DIAGNOSTIC KITS

FIELD OF THE INVENTION

The present invention relates to a polypeptide comprising the amino acid sequence as set forth in SEQ ID No. 1 of hepatitis E virus ORF 2 or its fragment, which is in the form of N-polymeric polypeptide, wherein N is an integer from 1-180; to a chimeric protein consisting of a polypeptide of the present invention and a conserved fragment of hemagglutin antigen from influenza virus; to a polypeptide of the present invention bound to a polypeptide containing epitope from hepatitis E virus ORF3 or an immunogenic fragment thereof; to a recombinant expression vector comprising the DNA molecule encoding the above polypeptides and the host cell transformed with said recombinant expression vector which is able to express polypeptide of the present invention.

The present invention further relates to a vaccine composition against hepatitis E virus which comprises the above-mentioned polypeptide, or diagnostic kit for hepatitis E virus infection comprising the above-mentioned polypeptide, which includes IgG, IgM, or total antibody diagnostic kit for hepatitis E virus, and to the use of vaccine composition and diagnostic kit for prophylaxis, diagnosis and/or treatment of hepatitis E virus infection.

BACKGROUND OF THE INVENTION

Hepatitis E Virus (HEY) was firstly recognized as a pathogen to enterically transmitted non-A, non-B hepatitis in 1983 (Balayan et al., 1983. Intervirology 20:23). Hepatitis E is mainly endemic in developing countries in Asia, Africa and Middle America. In developed countries, hepatitis E cases were mostly found in immigrants or traveler from abroad. Both sporadic cases and large epidemic have been documented. During the period from 1950s to 1990s, several hepatitis E outbreaks happened sequentially due to polluted drinking water (Visvanathan, 1957, Indian J. Med. Res. (Suppl.). 45:1-30; Wong et al., 1980 Lancet., 2:882-885; Myint et al., 1985, Am J Trop Med. Hyg., 34:1183-1189; Belabbes et al., 1985 J Med. Virol., 16:257-263; Hau et al., 1999, Am J Trop Med. Hyg., 60:277-280). Most hepatitis E infection was self-limited and scarcely developed into chronic; but for the pregnant, the sequel was severe with a mortality rate above 17% (Tsega et al., 1992, Clin. Infec Dis., 14:961-965; Dilawari et al., 1994, Indian J. Gastroenterol., 13:44-48; Hussaini et al., 1997, J Viral Hepat., 4:51-54).

In 1991, researchers got the first complete genome sequence of HEV, a single-strand non-enveloped positive RNA virus (Tam et al., 1991, Virology 185:120-131). Sequence analysis showed the genome was 7.2 kb with three open reading frames. ORF1 which locates at 5' end encodes non-structural protein of the virus, ORF2 which locates at 3' end encodes major structural protein of the virus. At ORF3 5' end, there is one by overlapped with ORF1 3' end. At ORF3 3' end, there are 339 by overlapped with ORF2 end. It's acknowledged that ORF3 encodes another structure protein with unknown function (Tam et al., 1991, Virology, 185:120-131; Aye et al., 1992, Nucleic Acids Res., 20:3512; Aye et al., 1993, Virus Genes., 7:95-109; Huang et al., 1992, Virology, 191:550-558; Reyes et al., 1993, Arch Virol Suppl., 7:15-25).

The detection of HIV infection mainly depended on Immunological Electron Microscope (IEM) or Immunological Fluorescence Technique for a long time, but those techniques are very complicated, expensive and hard to be fulfilled in many laboratories. After the clone and sequencing of HEV genome, more sensitive techniques like ELISA, Western Blot, PCR, etc. were developed to be used in the detection of HIV infection.

It is well recognized that the development of serum HEV antibody kits is absolutely necessary, but due to very low-concentration HEV virus secreted by the infected human or animals, thus it is impossible to use sera as the source of antigen. Till now, the efficiency of HEV cell culture is still very low, which limited the availability of enough antigens for HEV detection. Thus, the detection of HEV antibody is still depending on synthesized polypeptides or recombinant antigens. Unfortunately, many serological studies showed greatly varied consistence based on synthesized polypeptides or recombinant antigens from different HEV genome regions. For example, Goldsmith et al., (1992, Lancet, 399:328-331) used ORF2 3-2(M) antigen (a.a. 613-660, Mexico strain) to detect in-hospital hepatitis E virus infection cases. The detecting rate of IgG was 91%, and fell to 27~50% after 6-12 month. When he used 3-2(B) (The same ORF2 fragments from Burma strain) in detection, the rate was just 64% and no positive result was found after 6-12 months. On the contrary, 3-2(M) could not react with the convalescent serum in a Parkistan subject, but 3-2(B) could react with the serum of the same case 4.5 years later. For those proteins, when the antibody in some cases turned negative, in others it still remained in high titer. The results were similar when the mosaic protein with several linear epitopes expressed in E. Coli was used. Lack of good HEV antibody kits limited deep research on the dynamic of antibody during HIV infection. In general, during HIV infection, specific IgG antibody is detectable in early stage, peaks after 2~4 weeks and declines quickly. Most turned to negative after 9 months, but some patients kept positive many years later. Recently, several recombinant antigens have been expressed in both baculovirus and E. coli, which reacts strongly with sera from both acute and convalescence phase. In principle, these antigens are more suitable for sero-epidemiological survey: the titer of serum HEV IgG fell rapidly after acute stage, but it still retained at a detectable level. It's worthy of notification that the antibody is related to the protection from infection during the disease epidemic.

In the other way, due to the fact that only indirect methods of detecting methods are available up to date, no established HEV IgM kit is ever developed around world. With respect to the indirect methods, on the one hand, the detect result is affected by various factors and reproduction is poor; on the other, the reliability of the result is poor for high possibility of false positive, higher negative value, or lower sensitivity. According to recent reports, during the detection of clinical samples, when the result for IgM is positive, IgG is generally positive too, thus its value on early diagnosis is limited but may be helpful in elevation of the specificity of diagnosis of acute infection.

It's reported that the antibody to several synthesized peptide and some recombinant antigens will disappear quickly in many infected subjects, so clinical diagnosis on acute hepatitis E virus infection is generally based on IgG antibody with a higher clinical concordance, but the most important defect of this method is that it can not distinguish past infection from recent infection, which will lead to both false diagnosis in high hepatitis E virus endemic area and under evaluation of the prevalence of hepatitis E virus infection during epidemiological studies. Therefore, there is urge demand to develop a reliable and sensitive anti-µ chain IgM diagnostic kit and IgG diagnostic kit which is characterized by high sensitivity toward convalescence sera.

In recent years, there was some progress in developing a highly sensitive IgG diagnostic kit. Mast et al. (1998, Hepatology, 27: 857-861) provided a comprehensive evaluation of 10 major IgG antibody EIAs around world. The concordance of many kits was fairly good in detecting known positive sera, but great difference existed among different kits in detecting American blood donors. It implied that the reliability of the results is worse in HEV prevalence studies in non-endemic areas. Among those kits, most antigens are based on linear epitopes of HEV, but two kits used conformational epitopes as antigens. First is ORF2.1 aa394~660), the other is baculovirus expressed VLP (aa112~607). Both antigens can detect convalescence antibody, but direct data on the comparison of the concordance between those two antigens is not available till now. It's possible that those two antigens identified different antibodies. In addition, nearly 20% prevalence was reported in non-endemic America using VLP kit, which aroused the suspicion of its specificity. But with the reported positive HIV infection in swine, goats, cows, chickens, rats, wild monkeys and enclosed monkeys, together with separately 77% and 44% antibody prevalence among wild rats in Maryland and Louisanna, it's possible that the antibody prevalence is underestimated in American population, though animal HEV can not cause clinical disease due to its virulence. (Kabrane-Lazizi et al., 1999 μm Tropic Medicine, 61:331-335). And ORF2.1 kit can detect higher positive rate among CMV infection and autoimmunological diseases. In addition, the reported ORF2.1 polypeptide, which is a GST-conchimeric protein or polyarginine conchimeric protein, intends to obtain false positive results in practice.

Both cell and tissue culture for HEV have ever been successful, and practical methods to get a large amount of virus is not yet available, so it's the only research way to switch from tradition killed or attenuated vaccine to subunit or DNA vaccine through genetic engineering.

HEV ORF2, beginning at the base positioned at 5147, has 1980 nucleotides, which encodes a polypeptide with 660 amino acids presumed to be major structural protein and constitutes the capsid of virus. At N terminal of ORF2 protein, there is a classical signal sequence followed by a region rich in arginine, which is highly positive charged region and believed to involve in genomic RNA encapsidation during virus assembly. During translation process, ORF2 entered endoplasmic reticulum (ER) by a mechanism of signal peptide recognized protein (SRP), and is further glycosylated and accumulated in ER, then probably formed the capsomer of capsid in suit. Three N-glycosylated sites, Asn-137, Asn-310 and Asn-562, are located at ORF2. They are highly conservative among different virus strains, and Asn-310 is the major glycosylated site. ORF2-transfected mammalian cell COS, human hepatocellular carcinoma Huh-7, HepG2 can thereby express a 88 kD glycoprotein which can be found in both cytoplasma and membrane. The mutation in those glycosylated sites did not affect the location of PORF2 onto cell membrane. However after the signal peptide sequence was removed therefrom, PORF2 can only be found in cytoplasma. This implied that the shift of PORF2 instead of glocosylation is necessary to protein location onto cell membrane. Like MS protein in HBV, PORF2 is possibly secreted to cell membrane directly through ER instead of Golgi body. On the surface of transfected cell, gpORF2 is not randomly distributed, but concentrated in some zone, which implied an active combination process of a protein subunit and maybe aggregate into some more ordered advance forms. The final assembly/maturation of the virus need the encapisidation of genomic RNA, thus it must be occurred in cytoplasma outside of ER or endo-wall of cell membrane. The accumulation of gpORF2 in membrane may imply the assembly of virus. At the same time, the location of capsid protein on membrane also implied the possibility of secretion of matured virus out of the cell through budding. One more attention should be drawn that, the in vitro transcript and translation of PORF2 using in-vitro translation system with translating and modifying function can produce 88 kD of gpORF2 in forms of both monomers and dimers. It illustrated that gpORF2 was prone to form homologous dimer, and capsomer of capsid may be constituted by said homologuos dimer of gp ORF2 (Jameel et al., 1996. J. Virol., 70:207-216.). Through Frost Etching election microscope, Li et al. found that recombinant HEV VLPs which is expressed by baculovirus had an icosahedral symmetry virons (T=1), which was made up of sixty p50 subunits with 22-23 nm in diameter. Since the inner space of this size particle can contain about 1 kb RNA, and HEV genome is 7.5 kb in length, it is speculated natural HEV should be a crystal lattice structure with T.gtoreq.3, but the topological structure of capsomer is similar. The total number of T=3 subunit is 90 capsomers (Li et al., 1999. virology, 265:35-45.).

According to the above, HEV is a non-enveloped virus. Virus capsid is made up of ORF2-encoded protein. The protein embodies major immunological epitopes and some neutralizing epitopes, thus it became the most favorable fragment during subunit vaccine research.

In U.S. Pat. No. 5,885,768, Reyes et al. firstly reported that 4 cynomolgus monkeys were injected i.m. with recombinant protein tipE-C2 expressed in *E. Coli* comprising HEV Burma strain ORF2 C terminal 2/3 (aa225~660), wherein said protein is formulated with an alum adjuvant, by administering at 0, 30 day for 50 μg/dose. Another 2 monkeys were used as controls with adjuvant only. Four weeks later, no positive result regarding raised antibody from collected bloods is found by Western Blotting. A third-time immunization on two monkeys among them by administering 80 μg unsolvable recombinant protein without adjuvant. Four weeks later, both monkeys were positive (WB). Then the six monkeys were grouped into first and second group, each included three monkeys, two of them is immunized with either three-times or two-times inoculation, and one is control. The first group was attacked with Burma HEV, and the second group Mexico HEY. The results were, (1) ALT kept normal all the time in the immunized group, but it increased 6~10 times higher than before immunization in control; (2) Liver biopsy sample was detected by Immunological Fluorescence method. The antigen can be found in all other monkeys except those immunized with three doses and attacked by Burma strain. (3) Virus excretion in feces can be found sequentially in all other monkeys except those immunized with three doses and attacked by Burma strain. This research sample is small, but it implied that recombinant protein from ORF2 can block the occurrence of biochemical indexes of virus hepatitis and protected completely from infection when the monkeys were attacked by wild HEV.

Tsarev et al. (1994, Proc. Nat. Acad. Sci. USA., 91:10198-10202; Tsarev et al., 1993, J. Infect. Dis., 168:369-378; Tsarev et al., 1997, Vaccine 15:1834-1838) used baculovirus in insect (SF cell) to express HEV ORF2 and got protein particles with various size from 20 nm~30 nm in cell solution. The percentage of smaller particles is substantively increased during anaphase of infected cells. WB method was used to detect baculovirus expressed ORF2 with many specific different-size bands at 25 kD, 29 kD, 35 kD, 40-45 kD, 55~70 kD, 72 kD. Ion exchange and molecular screening method were used to purify HEV specific protein. One day after recombinant virus infected the cells, the whole ORF2 peptide of 72 kD firstly appeared and then disappeared gradually. On the second day, the peptides of 63 kD and 55 kD appeared. On the first day, 53 kD peptide appeared in cell solution with large amount and peaked on the third day. This implied the primary 72 kD protein was randomly cut into HEV protein with 55 kD (in cell lysis solution) and/or 53 kD (cell solution). The sequencing to those two proteins showed 55 kD located at ORF2 aa112~607, but 53 kD located at aa112~578 and 63 kD at aa112~660. The results of ELISA showed the activity of 55 kD was apparently stronger than 53 kD. If aa112~660 fragment was expressed in baculovirus in insect, 63 kD and 55 kD recombinant HEV protein can also be found.

SF9 cells were collected at day 7 from the cells had been infected. The protein was primarily purified and absorbed with alum adjuvant. Then cynomolgous monkeys were immunized i.m. with 50 µg protein per dose. Four received 1 dose, the other four two doses (0 d, 28d) After the final dose, all monkeys were attacked with dose 1000~10000CID50 i.v. of the same HEV strain (SAR-55, from a Parkistan patient). Within 15 weeks, liver biopsy, sera and feces were collected every week. Before virus attack, antibody titers in one-dose monkeys were 1:100~1:10000, but in two-dose group they were all 1:10000 (coated with purified 55 kD). In one-dose group, one monkey was dead due to anesthesia accident 9 weeks after virus attack (still calculated in the results). In two-dose group, two monkeys died soon after the virus attack (no calculated in the results) due to unknown reason. Six monkeys after immunization were found no ALT elevation or liver biopsy pathological change, and no viremia. Among four monkeys in one-dose group, three has virus excretion, but two monkeys in two-dose group no virus excretion was found.

Further purification was done in 55 kD protein expressed in baculovirus system through ion exchange and molecular sifting methods to make its purification reachable above 99%. After absorbed with alum adjuvant, the protein with dose 50 µg, 10 µg, 2 µg, 0.4 µg, 0 µg (control) was each injected into 4 rhesus monkeys administered 0 and 28 day. Four weeks after the last dose, the monkeys were attacked with the same virus (SAR-55). Sixteen monkeys in the immunized group were all normal, and just one monkey with 2 µg dose and the other with 0.4 µg dose appeared very light pathological change. Though the immunized can prevent from hepatitis but not infection. All sixteen monkeys immunized appeared virus excretion, also viremia except one monkey with 50 µg dose and the other with 10 µg dose. And the amount of virus was limited in most monkeys, but the duration has not been shortened. Another four monkeys were immunized with 2×50 µg, and attacked with 100,000 MID50 other HEV 4 weeks after the final dose. The results were similar. All four monkeys did not show ALT elevation and pathological change, but only one monkey did not show virus excretion and viremia. The amount of virus decreased apparently, but the duration has not been shortened. According to the author's opinion, the effect of complete protection on those monkeys was worse that previous time. It's possibly attributable to the amount of virus used in attack. The amount of virus in this experiment reached 300,000, but was 1000~10000MID50 last time. One more, the titer of antibody among groups from 0.4 µg to 50 µg has showed no difference before attack.

The staffs in Genelabs company expressed ORF2 aa112~660 using the same baculovirus in insect and got a large amount solvable recombinant 62 kD protein. After purification, the cynomolgous monkeys were immunized and protected from the attack of virus (Mexico strain) with dose 1000CID50 (3 monkeys immunized with 20 µg did not get disease. Virus excretion was not found in two monkeys, and the amount of virus excretion decreased in one monkey). (Zhang et al., 1997, Clin Diagn Lab Immunol.; 4:423-8.)

McAtee et al., (1996, Protein Expr. Purif., 8:262-270) prepared Burma ORF2 62 kD dimer expressed in recombinant baculovirus. The dimer was dissociated into two peptides separately with 56.5 kD and 58.1 kD through HPLC-MS. Peptide mass fingerprint analysis showed the N terminal of those two peptides was the same aa112, and the C terminal is separately aa637 and aa652. And 56.5 kD protein was a very good immunogen.

Anderson group in Australia (Anderson et al., 1999.1. Virol. Methods., 81:131-142; Li et al., 1994, J Clin Microbio.) 32:2060-2066; Li et al., 1997 J. Med. Virol., 52:289-300; Li et al., 2000, J. Med. Virol., 60:379-386) used ORF2 aa394~660 (ORF2.1) expressed in E. Coli. The product is a GST-conchimeric or poly arginine protein which can form a highly conformational convalescence epitope. This epitope can detect a very high-rate convalescence sera, but it will disappear when the fragment was extended or truncated towards N terminal. The serum at 30 weeks after rats were immunized with recombinant ORF2.1 protein was used to block the serum from convalescence patients with VLP expressed in baculovirus as the coated antigen. The blocking rate will reach 81%~86%. Monoclonal antibody was prepared with ORF2.1 protein and two monoclonal antibody 2E2 and 4B2 which can identify ORF2.1 conformational epitopes, and five possible identifiable monoclonal antibodies were obtained. The blocking rate can reach 60% whether 2E2 or 4B2 was used to block convalescence sera with VLPs as antigen. This implied that those two monoclonal antibodies can identify the epitopes which was major components of antibody identified epitopes in convalescence sera. Different data showed that ORF2.1 had major epitope structure rather similar to VLP. The antibody to the epitopes can exist for a long time in HIV infected serum. It's probably an important protective epitope, but animal protection experiment about ORF2.1 has not been reported till now.

SUMMARY OF THE INVENTION

In one aspect of the present invention, it provides a polypeptide comprising the amino acid sequence of hepatitis E virus open reading frame (ORF) 2 (as set forth in SEQ ID No. 1) or its fragment, which is in the form of n-polymeric polypeptide, wherein n is an integer from 1-180, said polypeptide comprising the amino acid as set forth in SEQ ID No. 1 of hepatitis E virus ORF 2 or its fragment is selected from the group consisting of:

1) A polypeptide having the amino terminus starts from between amino acid residues 113 and 469, and the carboxyl terminus ends from between amino acid residues 596 and 660;

2) A polypeptide having the amino terminus starts from between amino acid residues 370 and 469, and the carboxyl terminus ends from between amino acid residues 601 and 628;

3) A polypeptide having the amino terminus starts from between amino acid residues 390 and 459, and the carboxyl terminus ends from between amino acid residues 601 and 610;

4) A polypeptide having the amino acid sequence of amino acid residues 414 to 660 from SEQ ID NO:1, i.e., polypeptide 247;

5) A polypeptide having the amino acid sequence of amino acid residues 429 to 660 from SEQ ID NO:1, i.e., polypeptide 232;

6) A polypeptide having the amino acid sequence of amino acid residues 439 to 660 from SEQ ID NO:1, i.e., polypeptide 222;

7) A polypeptide having the amino acid sequence of amino acid residues 459 to 660 from SEQ ID NO:1, i.e., polypeptide 201;

8) A polypeptide having the amino acid sequence of amino acid residues 394 to 628 from SEQ ID NO:1, i.e., polypeptide 235N;

9) A polypeptide having the amino acid sequence of amino acid residues 394 to 618 from SEQ ID NO:1, i.e., polypeptide 225N;

10) A polypeptide having the amino acid sequence of amino acid residues 394 to 602 from SEQ ID NO:1, i.e., polypeptide 209N;

11) A polypeptide having the amino acid sequence of amino acid residues 394 to 601 from SEQ ID NO:1, i.e., polypeptide 208N;

12) A polypeptide having the amino acid sequence of amino acid residues 394 to 606 from SEQ ID NO:1, i.e., polypeptide NE2I;

13) A polypeptide having the amino acid sequence of amino acid residues 390 to 603 from SEQ ID NO:1, i.e., polypeptide 217D;

14) A polypeptide having the amino acid sequence of amino acid residues 374 to 618 from SEQ ID NO:1, i.e., polypeptide 205;

15) A polypeptide having the amino acid sequence of amino acid residues 414 to 602 from SEQ ID NO:1, i.e., polypeptide 189;

16) A polypeptide having the amino acid sequence of amino acid residues 414 to 601 from SEQ ID NO:1, i.e., polypeptide 188;

17) A polypeptide having the amino acid sequence of amino acid residues 459 to 628 from SEQ ID NO:1; and 18) A polypeptide having the amino acid sequence of amino acid residues X to 603 from SEQ ID NO:1 with Met added at N-terminus and a modified C-terminus, wherein said modified C-terminus refers to add, in the direction from 5'-3', amino acid sequence -Pro-Pro-Arg at amino acid residue 603, Pro, on its 3' end; including:
  a) when X is amino acid residue 394, said polypeptide is as set forth in SEQ ID NO:2, i.e., NE2;
  b) when X is amino acid residue 414, said polypeptide is as set forth in SEQ ID NO:3, i.e., 193C;
  c) when X is amino acid residue 429, said polypeptide is as set forth in SEQ ID NO:4, i.e., 178C;
  d) when X is amino acid residue 439, said polypeptide is as set forth in SEQ ID NO:7, i.e., 168C;
  e) when X is amino acid residue 449, said polypeptide is as set forth in SEQ ID NO:8, i.e., 158C;
  f) when X is amino acid residue 459, said polypeptide is as set forth in SEQ ID NO:9, i.e., 148C;
  g) when X is amino acid residue 469, said polypeptide is as set forth in SEQ ID NO:10, i.e., 138C;

In another aspect of the present invention, it further provides a polypeptide having at least 80% homology to any one of the preceding polypeptides as presented in the above 1)-18) and having substantially identical biological property, such as antigenicity or immunogenicity, etc.

In another aspect of the present invention, it further provides a recombinant expression vector comprising the nucleotide sequence encoding the above-mentioned polypeptides of the present invention. In another aspect of the present invention, it further provides a host cell transformed with any one of the above recombinant expression vectors, which is able to express the polypeptide(s) of the present invention.

In another aspect of the present invention, it further provides a vaccine composition for prophylaxis and/or treatment of hepatitis E virus infection in mammals, which comprises at least one of the polypeptides of the present invention or any combination thereof, and optionally, pharmaceutically acceptable vehicles and/or adjuvant.

In another aspect of the present invention, it further provides a chimeric protein comprising a polypeptide of the present invention and a conserved fragment of hemagglutin antigen from influenza virus.

In another aspect of the present invention, it further provides a vaccine composition for prophylaxis and/or treatment of hepatitis E virus infection in mammals, which comprises chimeric protein consisting of one of polypeptides of the present invention and a conserved fragment of hemagglutin antigen from influenza virus, and optionally, pharmaceutically acceptable vehicles and/or adjuvant.

In another aspect of the present invention, it further provides use of the above-mentioned vaccine compositions for vaccinating mammals to prevent from hepatitis E virus infection.

In another aspect of the present invention, it further provides a method for prophylaxis and/or treatment of hepatitis E virus infection in mammals, which comprises administrating to the subject with a prophylaxis and/or treatment effective amount of at least one of the above-mentioned polypeptide (s) or chimeric protein (s) consisting of at least one of the above-mentioned polypeptide and a conserved fragment of hemagglutin antigen from influenza virus.

In another aspect of the present invention, it further provides a diagnostic kit for the diagnosis of hepatitis E virus infection in biological sample, which comprises a diagnosis effective amount of at least one of the polypeptides of the present invention or any combination thereof.

In another aspect of the present invention, it further provides a diagnostic kit for the diagnosis of hepatitis E virus infection in biological sample, which comprises a diagnosis effective amount of at least one of the polypeptides of the present invention or any combination thereof, and further comprises the polypeptide containing immunogenic epitope from hepatitis E virus ORF3 or an immunogenic fragment thereof, wherein said polypeptide containing immunogenic epitope from hepatitis E virus ORF3 or an immunogenic fragment thereof is, optionally, covalently bound to said polypeptide.

In another aspect of the present invention, it further provides a method for diagnosis hepatitis E virus infection in biological samples, comprising contacting the above-mentioned diagnostic kit with sample to be detected under the conditions suitable for the interaction of antigen and antibody.

In another aspect of the present invention, it further provides a method for detecting total antibodies against hepatitis E virus, a method for detecting antibody IgG against hepatitis E virus, and a method for detecting antibody IgM against hepatitis E virus in biological samples.

BRIEF DESCRIPTION OF THE DRAWINGS

FIG. 4 shows the results of Western blotting analysis of polypeptide 201 with serum from HEY-infected patient. Lanes 1-3 is SDS PAGE control, wherein lane 1, protein molecular weight marker; lane 2, renatured sample of polypeptide 201 in 1×PBS; Lane 3, renatured polypeptide 201 treated in boiling water bath for 10 min; Lane 4 and 5,the respective Western blot results corresponding to the sample of Lanes 2 and 3.

FIG. 9 illustrates the profile of HEV antibodies raised in sera from mice following immunization with vaccine of polypeptide 201 (containing aluminum hydroxide as adjuvant) in various dosages. The horizontal coordinate is defined as the days after the first immunization. The vertical coordinate is defined as the $OD_{450\ nm/620\ nm}$ of ELISA.

DETAILED DESCRIPTION OF THE PREFERRED EMBODIMENT

Figure 1:
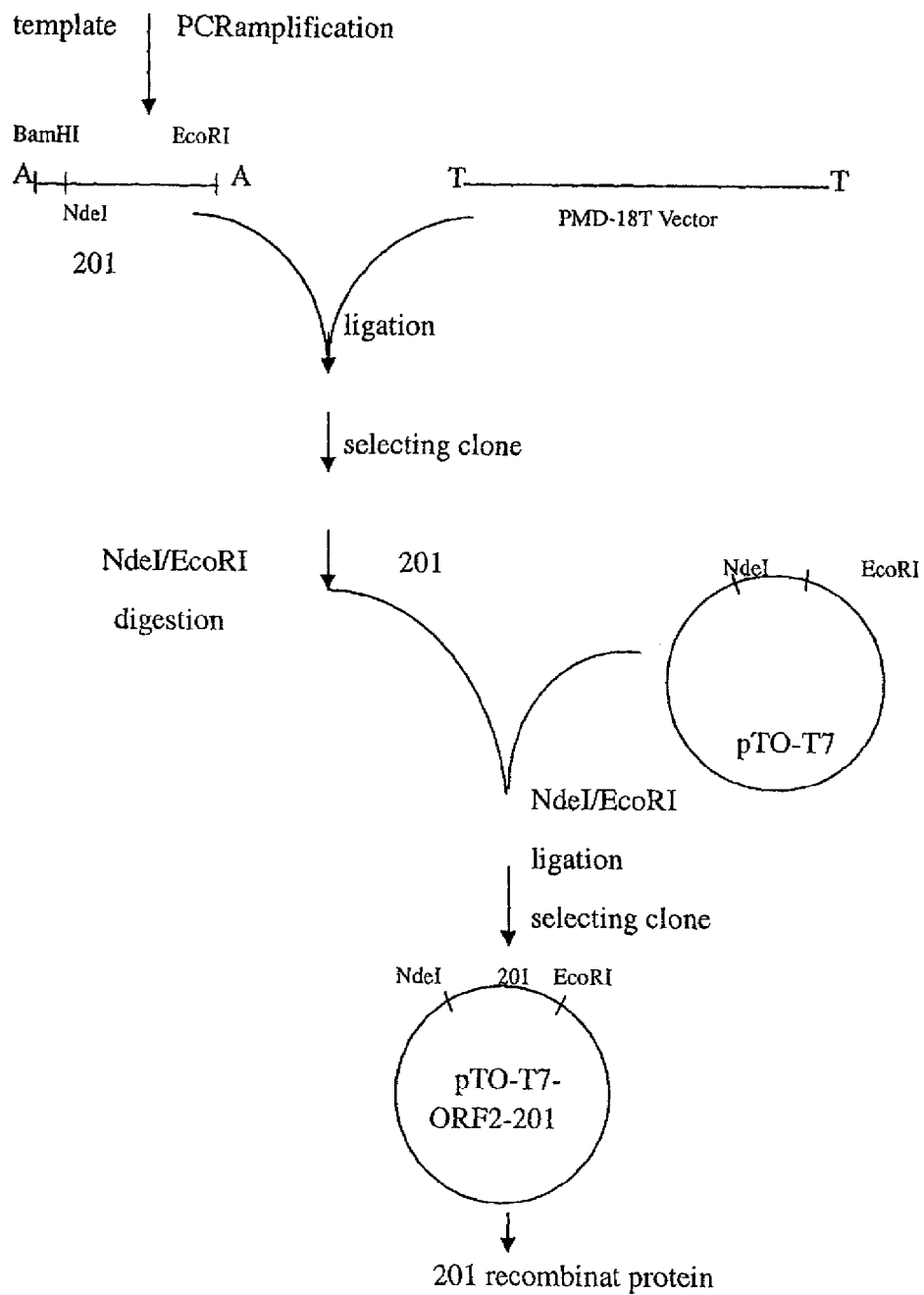
FIG. 1 presents a schematic diagram of the construction of plasmid pTO-T7-ORF2-201 for expression of the polypeptide 201.
Figure 2:
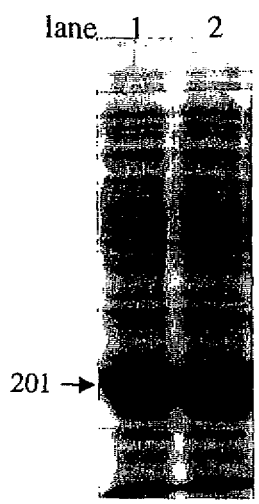
FIG. 2 shows the results of analysis by 12% sodium dodecyl sulfate polyacrylamide gel (SDS-PAGE) (Coomassie brilliant blue 8250 staine) regarding culture lysates of the induced E. coli transformed with expression vector pTO-T7-ORF2-201 (with steps of: centrifuging culture medium, collecting precipitated cell, then resuspending pellet with loading buffer including 0.1% SDS, further treating it in boiling water 10 min, then centrifuging under 12,000 rpm for 10 min, taking supernatant for determination). Lanes 1 and 2 respectively contain two different bacteria culture lysates. Expressed products take up around 35% of total protein as analyzed by Uvi gel imaging system (UVItec, ltd., model DBT-08).

Unless otherwise indicated, all the terms or nomenclatures used herewith are the same as those conventionally used in the art. The conventional manufactures in cell culturing, molecular genetics, nucleic acid chemistry, and immunological precedure are carried out as routine technique in the art. In the present invention, unless otherwise indicated, these terms used herewith have the meanings as follows:

"hepatitis E virus" or "HEV" refers to a virus, virus type or virus class, which i) causes water-borne, infectious hepatitis; ii) it distinguishes from hepatitis A virus (HAV), hepatitis B virus (HBV), hepatitis C virus (HCV), or hepatitis D virus (HDV) in terms of serological characteristics; iii) contains a genomic region that is homologous to a 1.33 kb cDNA inserted in pTZKF1(ET1.1), said plasmid is embodied in a E. coli strain deposited in American Type Culture Collection (ATCC) with accession number 67717.

The Polypeptide of the Present Invention

In one aspect, the present invention surprisingly provides a series of polypeptide fragment of HEV with satisfied antibody reactivity and/or immunogenicity, wherein said fragment is included in the amino acid sequence of HEV ORF2, as set forth in SEQ ID NO:1. The name of individual fragment could be found in table 1 of example 6.

In the present invention, the numbering of the amino acid residue by position in the amino acid sequence is in accordance with the numbering manner of International Union of Pure and Applied chemistry and International Union of Biochemistry, Joint commission on biochemical Nomenclature, "Nomenclature and symbolism for Amino Acids and Peptides", Pure Appl. Chem., 56, 595-624 (1984). Specifically, the coding start site Met in Seq Id No: 1 is designed as position 1, increased in the direction from 5' to 3'.

In one aspect of the present invention, a polypeptide is provided, which comprises the amino acid sequence as set forth in SEQ ID No. 1 of hepatitis E virus ORF 2 or its fragment in the form of n-polymeric polypeptide, wherein n is an integer from 1-180. When n is 2, said polypeptide is a dimer polypeptide; when n is 3, said polypeptide is a trimer polypeptide; when n is 4, said polypeptide is a tetrammer polypeptide, and so on.

In the present invention, the amino terminus (5' end) of said polypeptide fragment comprising amino acid sequence as set forth in SEQ ID NO: 1 starts from between amino acid residue 113 and 469, preferably, from between amino acid residue 370 and 469, more preferably, from between amino acid residue 390 and 459; and the carboxyl terminus (3' end) of said poly peptide ends from between amino acid residues 596 and 660, preferably, from between amino acid residue 601 and 628, more preferably, from between amino acid residue 601 and 610. Specifically, the preferable polypeptides of the present invention are polypeptide 247, polypeptide 232, polypeptide 222, polypeptide 201, polypeptide 235N, polypeptide 225N, polypeptide 209N, polypeptide 208N, polypeptide NE2I, polypeptide 217D, polypeptide 205, polypeptide 189, polypeptide 188, and the polypeptide having amino acid sequence from amino acid residue 459 to 628 of SEQ ID NO; 1.

In the present invention, it further relates to the polypeptide having the amino acid sequence of amino acid residues X to 603 from SEQ ID NO:1 with Met added at N-terminus and a modified C-terminus, wherein said modified C-terminus refers to add, in the direction from 5'-3', amino acid sequence -Pro-Pro-Arg at amino acid residue 603, Pro, on its 3' end; including: a) NE2; b) 193C; c) 178C; d) 168C; e) 158C; f) 148C; g) 138C.

In another aspect of the present invention, it further relates to a polypeptide having at least 80% homology to any one of the preceding polypeptides and having substantially identical biological property, such as antigenicity or immunogenicity, i.e., the derivates of the polypeptide of the present invention. Specifically, the polypeptide is considered as derivates of polypeptide of present invention under the condition that the amino acid of said polypeptide comprises the amino acid sequence of aforementioned polypeptide with other amino acid than a natural sequence neighboring to the present polypeptide at N-terminus and/or C-terminus thereof, but it still substantively remain the similar biological property, such as, antigenicity and or immunogenicity etc. to the present polypeptide. Consequently, DNA fragment corresponding to the same is called derivate DNA of present invention. For example, for the purpose of expression and/or purification, it would be facilitate to purification by adding start amino acid (Methionine) or other leading peptide and/or signal peptide at N-terminus thereof, or by adding several Histidines at C-terminus thereof.

The present invention further contemplates the polypeptide having identical biological property, such as antigenicity and/or immunogenicity, etc. to any one of aforementioned polypeptides; or polypeptide having at least 80% sequence identity to any one of aforementioned polypeptides. The term "percentage identity" is intended to denote a percentage of nucleotides or of amino acid residues which are identical between the two sequences to be compared, obtained after the best alignment, this percentage being purely statistical and the differences between the two sequences being distributed randomly and over their entire length. Sequence comparisons between two nucleotide or amino acid sequences are conventionally carried out by comparing these sequences after having aligned them optimally, sadi comparison being carried out be segment or by "window of comparison" in order to identify and compare local regions of sequence similarity. The optimal alignment of the sequences for comparison may be produced, besides manually, by means of the local homology algorithm of Smith and Waterman (1981) Ad. App. Math., 2:482, by means of the local homology algorithm of Neddleman and Wunsch (1970) J. Mol. Biol., 48:443, by means of the similarity search method of Pearson and Lipman (1988), Proc. Natl. Acad. Sci., USA, 85: 2444, by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identify between two nucleic acid or amino acid sequences is determined by comparing these two sequences aligned in an optimal manner in which the nucleic acid or amino acid sequence to be compared may comprise additions or deletions compared to the reference sequence for optimal alignment between these two sequences. The percentage identity is calculated by determining the number of identical positions for which the nucleotide or the amino acid residue is identical between the two sequences, dividing this number of positions compared and multiplying the result obtained by 100 so as to obtain the percentage identity between these two sequences.

For example, program BLAST "BLAST 2 sequences" can be used, wherein parameter is default (particularly, open gap penalty is 5, extension gap penalty is 2; matrix is provided by such as program "blosum 62"), the percentage of identity between two sequences to be aligned is directly calculated by the program.

The Preparation of Polypeptide of the Present Invention

The polypeptide of the present invention can be prepared by methods known in the art, such as, chemical synthetic methods and recombinant DNA technology. Preferably, the preparation method for the polypeptide of the present invention can be through recombinant DNA expression. The methods for preparing recombinant protein are well-known in the art, which is not necessary described in detail herewith; in addition, reference could be made to the methods in examples. As to the cell useful for producing the recombinant protein, mention should be made to bacterial cell (P. O. Olins and S. C. Lee, 1993, Curr. Opi. Biotechnology, 4:520-525), yeast cell (R. G. buckholz, 1993, Curr. Opi. Biotechnology, 4:538-542), animal cell, especially mammals cell culture (C. P. Edwards and A. Aruffo, 1993, Curr. Opi. Biotechnology, 4:558-563), and insect cell. With respect to the method for insect cell, reference should be made to, e.g., baculovirus (V. A. Luckow, 1993, Curr. Opi. Biotechnology, 4:564-572). In this regard, the present invention further provides a recombinant expression vector, which comprising the nucleotide sequence encoding the above-mentioned polypeptide. The present invention still further provides a host cell transformed with the above recombinant expression vector, which is able to expression said polypeptides encoded by the nucleotide sequence contained therein.

In one embodiment of the present invention, E. coli is used to individually express the polypeptide of the present invention as follows: polypeptide 247, polypeptide 232, polypeptide 222, polypeptide 201, polypeptide 235N, polypeptide 225N, polypeptide 209N, polypeptide 208N, polypeptide NE2I, polypeptide 217D, polypeptide 205, polypeptide 189, polypeptide 188, and polypeptide a) NE2; b) 193C.

The ratio between monomer and dimer of said polypeptide, the formation of polymeric polypeptide and individual radium thereof are determined (see, Example 6 for detail). As the result shows that the expressed product is prone to refold. The capability for self-forming stable polymers in solution after refolding makes the polypeptide of the present invention particularly suitable to be used as vaccine, for the prophylaxis and/or treatment of HEV. In one of the embodiment in the present invention, the polymer including dimer, trimer, and tetramer has been detected in one test. Limited by the methodology up to date, there is possibility that the deduced trimer is in fact composed of the mixture of dimer and tetramer in a suitable ratio. It is also contemplated that the polypeptide of the present invention is able to form even larger polypeptide due to the improvement on methodology. Deducing from published reference (Jameel, et al., 1996, J. Virology, 70:207-216; Li, et al., 1999, Virology, 265:35-45), there is high possibility that natural HEV is composed of 90 sub-particles, wherein each sub-particles is dimer of ORF2 polypeptide. Therefore, it is reasonably contemplated that the polypeptide of the present invention is able to form a polymer of up to 180-merit polypeptide, or even larger polymers, with the development on the understanding of virus structure.

In another preferred embodiment in the present invention, although polypeptide 201 is expressed by *E. coli* in form of inclusion body with high yield, the present inventor surprisingly finds that said inclusion body is able to spontaneously self-renatured in the PBS buffer of pH7.45, which avoids the time-costing and tedious conventional denature/renature process that substantively reduce recovering rate, including the steps of adding guanidine hydrochloride and then undergoing multi-steps of dialysis. In addition, since other non-desired protein inclusion body simultaneously expressed by *E. coli* is unable to spontaneously self-renature, the protein of interest in the present invention can be substantively purified simply by centrifugation and recovering supernatant.

The chimeric protein consisting of polypeptide of the present invention and conserved fragment of hemagglutintin antigen from influenza virus In another aspect of the present invention, chimeric protein consisting of any one of the above-mentioned polypeptides and conserved fragment of hemagglutintin antigen from influenza virus is also provided. Hemagglutintin antigen (hereinafter designed as HA) is one the two surface antigens of influenza virus, and is the most imported antigen used in specific detection for antibody against influenza virus in the serum of subject. It is known that antibody raised by vaccinating animal with HA can effectively prevent the receipt from re-infection of influenza virus. Therefore, it is reasonable to believe that antibody against HA is presented in most of population. According to previous report (McEwen J. et al., Vaccine, 1992; 10 (6): 405-11), epitope 91-108 aa is the conserved amino sequence in HA gene among all the H3 strains of influenza virus type A. In one preferred embodiment of the present invention, firstly, chimeric expression in prokaryotic expression system, especially in *E. coli* is established by flexibly linking HA gene (91-108aa) to the polypeptide fragment of HEV ORF2 gene of the present invention that is highly immunogenic, such as Gly-Gly-Ser by genetic engineering. Then boost with HA antibody raised by previously infection of influenza virus, so as to generate high-titer protective anti-HEV antibody. In this way, a HEV vaccine is obtained that is super to the vaccine containing ORF2 fragment of polypeptide of the present invention alone.

In light of the teachings in the present invention, epitopes useful to the vaccine composition of the present invention can be selected from other conserved fragment in HA gene by skilled person in the art. As to the specific flexible linker linking specific epitope of HA and polypeptide of the present invention, it can be consisted of suitable peptide fragment or analog thereof, provided that it facilitate linkage between polypeptide of the present invention and selected fragment of HA and that does not substantively affect the use of polypeptide of the present invention for prophylaxis/treatment HIV infection in mammals. It should be understand, selection of linker for linking polypeptide of the present invention and HA mainly depends on the specific property of the selected polypeptide of the present invention. For example, different linkers might be selected according to selected polypeptide of the present invention to be linked with HA. Preferably, the conserved fragment of HA used in the present invention is a fragment from amino acid residue 91-108.

Linker for the linkage of polypeptide of the present invention as immunogen and selected fragment of HA can be synthesized preferably by conventional synthesis technique, such as chemical synthesis technique. In addition, any peptide can be synthesized by skilled person in the art in accordance with standard chemical method, such as t-BOC method by automatic peptide synthesisor (see, e.g., L. A. Carpino, J. Am. Chem. Soc., 79:4427, 1957). However, peptide can also be produced by chemically hydrolysis of protein or other known methods.

Alternatively, the chimeric protein of polypeptide of the present invention with HA can be produced by host cell transformed with nucleic acid sequence of a DNA molecule, wherein said DNA molecule comprise a sequence encoding fragment of HA and polypeptide of the present invention which is obtained by cloning in host microorganism or cell through conventional genetic engineering method, such as recombinant DNA technique. When it is generated by recombinant technique in the transformed cell, the resulted chimeric protein can be purified and recovered by routine method from culture medium, host cell or from the both. Said chimeric protein produced by recombination method is isolated so that the resulted peptide can be substantively separated from cell substance or culture medium during the recombinant production by recombinant DNA techniques. In addition, coding sequence for the resulted peptide could also be prepared by synthesis, or by using virus RNA in accordance known method or the available plasmid containing cDNA thereof.

For use in the present method, the above-mentioned chimeric protein can be designed to generally known construct or other construct in order to increase the production thereof or facilitate purification of the same. The suitable system and vectors is known and public available, or commercial available for cloning and expression chimeric peptide in various microorganisms and cells, including such as *E. coli, Bacillus, Streptomyces, Saccharomyces*, mammals, yeast, insect cell and plant cell.

The chimeric protein produced by either recombination or synthesis can be purified by routine purification method. The skilled person in the art can easily determine a desired purity for the polypeptide according to the use of interest.

Vaccine Composition

In another aspect of the present invention, it further provides a vaccine composition for prophylaxis and/or treatment of hepatitis E virus infection in mammals, which comprises at least one of polypeptides of the present invention or any combination thereof, and optionally, pharmaceutically acceptable vehicles and/or adjuvant.

In still another aspect of the present invention, it further provides a vaccine composition for prophylaxis and/or treatment of hepatitis E virus infection in mammals, which comprises chimeric protein containing a polypeptide of the present invention and a conserved fragment from hemagglutin antigen of influenza virus, and optionally, pharmaceutically acceptable vehicles and/or adjuvant.

In still another aspect of the present invention, use of above vaccine compositions for vaccinating mammals to prevent from hepatitis E virus infection is provided.

In present invention, mammals to be inoculated or treated includes but not limits to human being and other primates, such as baboon, ape, monkey, etc.; economic animals, such as, bovine, caprine, swine, rabbit, murine, as well as pets, such as feline, canine, etc. Said vaccine composition contains treatment and/or prophylaxis effective amount of at least one of polypeptide of the present invention, wherein said effective amount is the amount that sufficient for effectively treat subject infected by HEV or prevent subject from HIV infection after administrating for a certain time.

The vaccine composition of present invention could be used either alone or as part of the formulation for medicament or prophylaxis, which optionally contains pharmaceutically acceptable vehicles, including release-controlling agent. Said vehicles might further include pharmaceutically acceptable vectors or diluents suitable for the administration for treatment and/or prophylaxis of HIV infection. Suitable pharmaceutically acceptable vectors refer to those biologically inert and/or non-toxic. Various vectors known in the art can be selected according to desired use. Typically, said vector can be selected from but not limit to the group consisting of: sterile saline, lactose, sucrose, calcium orthophosphate, gelatin, dextrin, agar, alum, aluminum oxide, aluminum hydroxide, peanut oil, olive oil, sesame oil, and water. Additionally, vector or diluents can further include controlled released substance, such as glyceryl monostearate/glyceryl distearate, either alone or in combination with paraffin. In addition, conventional controlled release polymer formulation, including soluble glass can also be used.

Still further, when desired, the vaccine composition of the present invention comprising at least one polypeptide of present invention or any combination thereof can further comprise other treatment/prophylaxis agent. For example, said composition could comprise a "cocktail mixture" of various agent that is useful in the treatment or prophylaxis for HIV infection. Such cocktail mixture could further include other agents, such as interferon, nucleotide analogs and/or N-acetyl-cysteine.

Optionally, the vaccine composition of the present invention comprising at least one polypeptide of present invention might further comprise immune system modifiers, such as, adjuvants or cytokines useful for further induction of antibody and T cell response in subject. Said modifier includes conventionally alum-based adjuvants, muramyl dipeptides, preservatives, chemical stabilizers or other antigenic protein. Generally, stabilizers, adjuvants or preservatives and the like are optimized of dertmin the best formulation for efficacy in the desired application. Suitable preservatives may include chlorylbutynol, potassium sorbate, sorbaic acid, sulphur dioxide, propyl galade, parabens, glycerine, and phenol.

Method for prophylaxis and/or treatment of HIV infection in mammals using vaccine composition of the present invention In another aspect, the present invention provides a method for prophylaxis and/or treatment of hepatitis E virus infection in mammals, which comprises administrating to the subject with a prophylaxis and/or treatment effective amount of polypeptide (s) of the present invention or chimeric protein (s) consisting of at least one of polypeptides of present invention and conserved fragment of hemagglutin of influenza virus. In particularly, said method comprises the step of administrating to subject with the vaccine composition of the present invention. Preferably, the conserved fragment selected by the present invention is amino acid fragment from 91-108 amino acid residues.

Suitable amounts of these compositions may be determined based on the level of response desired. In general, compositions comprising the polypeptide of present invention may contain between about 5 ug and about 200 ug of the particles. Such compositions may be administered as one or a series of inoculations, for example, three inoculations at intervals of two to six months. Suitable dosage may also be determined by judgment of the treating physician, taking into account factors such as the patient's health status, weight or age, as well as the conventional dosage of a component immunogen, when administered as a monotherapy. Upon improvement of a patient's condition or likelihood of increase exposure to a given pathogen, a maintenance dose of a composition comprising polypeptide of present invention may be administered, if necessary. Subsequently, the dosage or frequency of administration, or both, may be reduced to a level at which the desired effect is retained. At that point, treatment should cease. Individuals may, however, require intermittent treatment on a long-term basis upon recurrence of a given unwanted condition.

Compositions comprising polypeptide of present invention may be administered by any suitable route, such as, for example, parenteral administration, particularly intramuscular or subcutaneous, as well as oral administration. Other routes, may also be used, such as pulmonary, nasal, aural, anal, dermal, ocular, intravenous, intraarterial, intraperitoneal, mucosal, sublingual, subcutaneous and intracranial.

Preparation of vaccine composition of present invention may be carried out to formulate injectable compositions or vaccine, either as liquid solutions or suspensions. Solid forms suitable for solution or suspension in liquid prior to injection may also be prepared. Preparations also may, in certain embodiments, be emulsified or encapsulated in liposomes, or in soluble glasses, for controlled released and for prolonged delivery. Alternatively, preparations may be in aerosol or spray form. They may also be included in trans-dermal patches. The active ingredient may be mixed with any number of excipients which are pharmaceutically acceptable and compatible with the active ingredient or ingredients. The excipients include, for example, Freund's incomplete adjuvant, bacterial lipopolysaccharides, ion exchanger, alumina, aluminum stearate, muramyl dipeptide, lecithin, buffer substance, cellulose-base substances and polyethylene glycol.

Diagnostic Kit and Method for Detecting Antibody IgG, IgM or Total Antibody against HEV in Biological Sample The polypeptide of the present invention can be used for detection of presence of antibody IgG, IgM or total antibody against HEV in biological sample, which is characterized in high sensitivity and high specificity, compared to exited detection kit or detection method. Therefore, the present invention provides a method for determine the presence of HIV infection in a biological sample, which comprises the step of contacting sample to be detected with detection effective amount of polypeptide of the present invention under a condition that suitable for antibody/antigen interaction.

The biological sample to be detected in the present invention derived from, includes but not limits to, human being and other primates, such as baboon, ape, monkey, etc.; economic animals, such as, bovine, caprine, swine, rabbit, murine, as well as pets, such as feline, canine, etc.

In another aspect of the present invention, the diagnostic kit for determination of antibody IgG against hepatitis E virus in the biological sample is provided, which comprises at least one of the polypeptides of the present invention, if desired, said polypeptide is pre-coated on the surface of a suitable support; and further comprises commercial available or routinely generated, detectable labeled antibody anti-IgG that is directed against IgG from biological sample to be detected, and detection agent corresponding to said detectable label; and if desired, further comprises a suitable buffer system.

In one embodiment of present invention, said biological sample to be detected is derived from human being, wherein antibody is anti-human IgG antibody. More specifically, the diagnostic kit for IgG antibody of the present invention further includes a polypeptide having immunogenic epitope in HEV ORF3 or an immunogenic fragment thereof, wherein said immunogenic epitope in HEV ORF3 or an immunogenic fragment thereof is optionally covalently bound to the polypeptide of present invention.

For the situation that said immogenic epitope in HEV ORF3 or an immunogenic fragment thereof is optionally covalently bound to the polypeptide of present invention, the chimeric polypeptide is preferably produced by genetic recombination method. Chemical method can also by used to covalently bind said immunogenic epitope in HEV ORF3 or an immunogenic fragment thereof to the aforementioned polypeptide.

In another aspect of the present invention, a diagnostic kit for determination of antibody IgM against hepatitis E virus in the biological sample is provided, which comprises commercially available or routinely generated, detectable labeled antibody anti-IgM as capture antibody that is directed against IgM from biological sample to be detected, if desired, said capture antibody is pre-coated on the surface of a suitable support; and further comprises detectable labeled at least one of the polypeptides of the present invention, and detection agent corresponding to said detectable label; if desired, further comprises a suitable buffer system.

In one embodiment of present invention, said biological sample to be detected is derived from human being, wherein antibody is anti-human IgM antibody. More specifically, the diagnostic kit for IgM antibody of the present invention further includes a polypeptide having immunogenic epitope in HEV ORF3 or an immunogenic fragment thereof, wherein said immunogenic epitope in HEV ORF3 or an immunogenic fragment thereof is optionally covalently bound to the polypeptide of present invention.

For the situation that said immunogenic epitope in HEV ORF3 or an immunogenic fragment thereof is optionally covalently bound to the polypeptide of present invention, the chimeric polypeptide is preferably produced by genetic recombination method. Chemical method can also by used to covalently bind said immunogenic epitope in HEV ORF3 or an immunogenic fragment thereof to the aforementioned polypeptide.

In another aspect of the present invention, a diagnostic kit for determination of antibody IgM against hepatitis E virus in the biological sample is provided, which comprises commercially available or routinely generated, detectable labeled antibody anti-IgM as capture antibody that is directed against IgM from biological sample to be detected, if desired, said capture antibody is pre-coated on the surface of a suitable support; and further comprises detectable labeled at least one of the polypeptides of the present invention, and detection agent corresponding to said detectable label; if desired, further comprises a suitable buffer system.

In one embodiment of present invention, said biological sample to be detected is derived from human being, wherein antibody is anti-human IgM antibody. More specifically, the diagnostic kit for IgM antibody of the present invention further includes a polypeptide having immunogenic epitope in HEV ORF3 or an immunogenic fragment thereof, wherein said immunogenic epitope in HEV ORF3 or an immunogenic fragment thereof is optionally covalently bound to the polypeptide of present invention.

For the situation that said immunogenic epitope in HEV ORF3 or an immunogenic fragment thereof is optionally covalently bound to the polypeptide of present invention, the chimeric polypeptide is preferably produced by genetic recombination method. Chemical method can also by used to covalently bind said immunogenic epitope in HEV ORF3 or an immunogenic fragment thereof to the aforementioned polypeptide.

In still another aspect of present invention, a diagnostic kit for determination of total antibodies against hepatitis E virus in the biological sample is also provided, which comprises at least one of the polypeptides of present invention, if desired, said polypeptide is pre-coated on the surface of a suitable support; and further comprises detectable labeled at least one of polypeptides according to claim 1, and detection agent corresponding to said detectable label; wherein said polypeptide selected from polypeptides according to claim 1 for pre-coating the surface of a support and the detectable labeled polypeptide selected from polypeptides according to claim 1 could be the same polypeptide, or different one.

More specifically, the diagnostic kit for total antibodies of the present invention further includes a polypeptide having immunogenic epitope in HEV ORF3 or an immunogenic fragment thereof, wherein said immunogenic epitope in HEV ORF3 or an immunogenic fragment thereof is optionally covalently bound to the polypeptide of present invention.

For the situation that said immunogenic epitope in HEV ORF3 or an immunogenic fragment thereof is optionally covalently bound to the polypeptide of present invention, the chimeric polypeptide is preferably produced by genetic recombination method. Chemical method can also by used to covalently bind said immunogenic epitope in HEV ORF3 or an immunogenic fragment thereof to the aforementioned polypeptide.

It is well known in the art that in the aforementioned diagnostic kit, anti-human IgG or anti-human-IgM which can be generated by various commercial available or routinely generated method taking advantage of various animals are used. Alternatively, anti-IgG or anti-IgM against the specific animals from which biological sample to be detected derived are used which can be generated by taking advantage of relating animals. For the purpose of preparing antibody, selected animal includes but not limit to goat, sheep, rat, mouse, rabbit, guinea pig, swine, etc. Said detectable label for labeling can be used alone or in combination with other composition or compound for providing detectable signal to visualize the presence of substance of interest in sample. Said detectable label can be those known and easily available materials in the art of detection field, including but not limited to enzyme marker, fluorescent marker, radioactive marker, etc. Thus, the present invention is not limited to specific selection of detection label, and contemplates that it includes all those detection method known in the art. For the purpose of convenience, said detection agent can be provided in the faun of kit.

Optionally, said kit further includes micro-titer plate pre-coated with polypeptide of present invention, various suitably formulated diluent and/or buffer, labeled substance or other signal-generating agent for detection of specifically bound antigen/antibody complex, such as, enzymetic substrate, co-factor and chromophore. Other components therein could be easily selected by skilled person in the art.

Additionally, a method for detecting antibody IgG against hepatitis E virus in biological samples is provided, which comprises the step of: immobilizing at least one of the polypeptides of present invention on the surface of a support; then washing with a suitable buffer; contacting it with sample to be detected under the conditions suitable for the interaction of antigen and antibody; washing again with a suitable buffer; and then incubating with commercial available or routinely generated, detectable labeled anti-IgG antibody a certain time sufficient for antigen/antibody interaction, wherein said anti-IgG is against the animal from which the biological sample to be detected derived; after that, detecting the antigen/antibody complex on the surface of a support by using detect agent corresponding to said detectable label, calculating the amount of antibody IgG in the sample In one embodiment of present invention, said biological sample to be detected is derived from human being, said antibody as used is anti-human IgG.

In another embodiment of present invention, polypeptide NE2I as antigen is pre-coated to the surface of a predetermined support. In another embodiment of present invention, polypeptide 247 coupled with epitope in HEV ORF3 is used as antigen to be pre-coated with specific surface of support.

In another aspect of present invention, a method for detecting antibody IgM against hepatitis E virus in biological samples is provided, which comprises the step of: immobilizing commercial available or routinely generated antibody anti-IgM on the surface of a support, wherein said anti-IgM is against the animal from which biological sample to be detected derived; washing suitably; contacting it with sample to be detected, preferably serum, under the conditions suitable for the interaction of antigen and antibody; washing again with a suitable buffer; and then incubating with detectable labeled at least one of polypeptide of present invention for a time sufficient for the interaction between antigen and antibody, after that, detecting the antigen/antibody complex on the surface of a support by using detect agent corresponding to said detectable label, calculating the amount of antibody IgM in the sample.

In one embodiment of present invention, said biological sample to be detected is derived from human being, said antibody as used is anti-human IgM.

In another embodiment of present invention, said IgM antibody in sample is detected by polypeptide 225N coupled with horseradish peroxidase. In still another embodiment of present invention, polypeptide 247 coupled with epitope of HEV IRF3 is further coupled with horseradish peroxidase to detect IgM contained in sample.

Additionally, a method for detecting total antibodies against hepatitis E virus in biological samples is also provided, which comprises the step of: immobilizing at least one of the polypeptides of present invention on the surface of a support; washing with a suitable buffer; contacting it with biological sample to be detected under the conditions suitable for the interaction of antigen and antibody; optionally, washing again with a suitable buffer; incubating with detectable labeled one of present polypeptide for a time sufficient for the interaction between antigen and antibody; and detecting antigen/antibody complex on the surface of a support by using antigen of hepatitis E virus with a detectable label and corresponding detect agent, calculating the amount of total antibodies in the sample.

In one embodiment of present invention, NE2I is pre-coated on the surface of support, and total antibodies in the sample is detected by polypeptide 225 previously coupled with horseradish peroxidase. In another embodiment of present invention, NE2I coupled with epitope from HEV ORF3 is pre-coated on the surface of support, and total antibodies in the sample is detected by horseradish peroxidase-bound polypeptide 225 which is previously coupled with epitope from HEV ORF3.

The present invention is further illustrated in details with reference to the following description of drawings and examples, which should not in any way be interpreted as the limitation to the protection scope of the present invention.

EXAMPLES

Unless specifically indicated, experiment methods of molecular biology and immunoassays of the present invention are all following those basically described in Molecular Cloning: a Laboratory Manual, 2nd Edition, Joseph Sambrook, David W. Russell, by Cold Spring Harbor Laboratory Press and Short Protocols in Molecular Biology, 3rd Edition, John Wiley & Sons, Inc., 1995. The use of restriction endonucleases follows the protocols provided by the producer.

Example 1

Preparation of the Genes Encoding the Polypeptides of the Present Invention and Construction of Expression Vector Containing the Same Preparation of the Fraction of HEV ORF2 as Template To prepare gene of interest, polymerase chain reaction (PCR) is used with a full-length HEV gene cloned from HEV-infected patient in Xin Jiang provine, China as template (Aye, T. T., Uchida etc., Nucleic Acids Research, 20(13), 3512 (1992); GeneBank accession number D11092), together with two primers, ORF2 FP:5'-atgcgccctcggcca-3' as (SEQ ID NO:13) as upper primer and ORF2 RP: 5'-aaataaac-tataactcccga-3' (SEQ ID NO:14) as lower primer. PCR reaction is carried out in PCR thermal cycler (BIOMETRA t3) under following condition: 94° C. 5 min; then 25 circles of: 94° C. 50 sec, 57° C. 50 sec and 72° C.2.5 min; ended by 72° C. 10 min. A DNA fragment about 2 kb is obtained, which is from HEV ORF 2 as the template for preparation of polypeptide of the present invention. The above-mentioned PCR product is further linked into commercial available vector pMD18-T (TAKARA CO.) and then digested with BamH I/Hind III, so as to identify the positive clone inserted with ORF2 gene. Using M13 (+)/(−) as primer, the resultant is sequenced and thereby identify the two DNA fragment of HEV ORF 2 which is used as the template for preparing polypeptide of present invention, one of them is a conservative sequence (Template 1, SEQ ID NO:5), the other is a mutant sequence (Template 2, SEQ ID NO: 6).

By sequence alignment and analysis of ORF, it is found that the mutant sequence of HEV ORF2 (SEQ ID NO:6) as template for preparing the polypeptide of present invention has a base A deleted, compared to conservative sequence (SEQ ID NO:5), which resulted in shift mutation that amino acid residues 604-605 in ORF2 are mutated from His-Ser-Val to Pro-Pro-Arg, and the translation for said polypeptide is thereby stopped by stop code tag formed by such mutation.

By way of example, the polypeptide 201 of present invention is used hereafter to illustrate the preparation of nucleotide encoding polypeptide 201 and the expression vector comprising the same.

The Preparation of Polynucleotide Encoding Polypeptide 201 of Present Invention and the Expression Vector Containing the Same.

The gene is synthesized using polymerase chain reaction (PCR), wherein the above-obtained sequence SEQ ID NO:5 is used as template, together with forward primers, 201FP:5'-ggatcccatatggttattcaggattatgac-3' (SEQ ID NO:15) (see, table 1), in which BamHI sites, NdeI sites (CAT ATG), and ATG as translation start codon in *E. coli* system are introduced; and 201RP: 5'-ctcgagaaataaactataactcccga-3' (SEQ ID NO:16) (see, Table 1) as reversed primer, in which stop codon and EcoR I site are introduced. The PCR is carried out in thereto cycler as follows: heat-denatured for 5 min at 94° C., then amplified for 30 circles: 50 sec at 94° C., 40 sec at 57° C. and 40 sec at 72° C., finally 10 min at 72° C. The resulted .about.600 by PCR product is identified as the nucleotide sequence encoding polypeptide 201 of present invention.

The construction of expression vector pTO-T7 for expressing the polypeptide of present invention is following the method in reference document of LUO Wen-Xin, et al., Chinese Journal of Biotechnology, 2000, 16:53-57. Said method includes steps of: cloning aforementioned PCR product into commercial available pMD18-T vector (TAKARA company), and digesting with BamHI/HindIII to identify and obtained the positive subclone inserted with nucleotide encoded polypeptide 201; further digesting said positive subclone with NdeI and EcoRI to obtain nucleotide sequence comprising gene of polypeptide 201, and then cloning into NdeI/EcoRI-digested pTO-T7. The positive clone pTO-T7-ORF2-201 that embodying encoding sequence of the polypeptide 201 is identified by digestion with NdeI/EcoRI. The strategy for constructing the expression vector for polypeptide of ORF 201 is illustrated in FIG. 1.

Similarly, other polypeptides of present invention whose carboxyl teiminus is other than Pro-Pro-Arg can be acquired according to the above method by using sequence of SEQ ID NO:6 as template, and using primers listed in Table that is specifically designed against individual polypeptide of interest.

The nucleotide encoding polypeptides of present invention whose carboxyl terminus is Pro-Pro-Arg and expression vectors containing the same.

The polypeptides of present invention whose carboxyl terminus is Pro-Pro-Arg is expressed by transforming E. coli ERR 2566 with expression vector obtained according to the above-mentioned method for expression vectoer of ORF2-201. Specifically, taken above-mentioned HEV ORF2 mutant sequence SEQ ID NO:6 as template, using individual forward/reverse primer specifically designed against individual polypeptide of present invention (see, Table 1), corresponding expression vector is obtained by PCR under similar the condition for generating expression vector of polypeptide 201. In this way, a series of polypeptide of present invention with good immunogenicity and immunoreactivity is obtained, wherein the resulted polypeptide has Met added at its N-terminus, and has amino acid sequence-Pro-Pro-Arg added in direction from 5'-3' at 3' end of amino acid 603, Pro, at its carboxyl terminus.

TABLE 1

PCR amplification template for the preparation of nucleotide encoding polypeptide of present invention and corresponding forward/reversed primers

| polypeptide | HEV ORF2 | position in template No. | forward primer (FP) and reversed primer (RP) | |
|---|---|---|---|---|
| NE2 | 394-603ppr* | 2 | HEFP: 5'-ggatcccatatgcagctgttctactctcgtc-3' | (SEQ ID NO: 17) |
| | | | HERP: 5'-ctcgagaaataaactataactcccga-3' | (SEQ ID NO: 16) |
| 217C | 390-603ppr | 2 | 217FP: 5'-ggatcccatatgtcggctggtggccag-3' | (SEQ ID NO: 18) |
| | | | HERP: 5'-ctcgagaaataaactataactcccga-3' | (SEQ ID NO: 16) |
| 193C | 414-603ppr | 2 | E220F: 5'-ggatcccatatgacatctgtagagaatgctca-3' | (SEQ ID NO: 19) |
| | | | HERP: 5'-ctcgagaaataaactataactcccga-3' | (SEQ ID NO: 16) |
| 178C | 429-603ppr | 2 | E235F: 5'-ggatcccatatgcatgacatcgacctcg-3' | (SEQ ID NO: 20) |
| | | | HERP: 5'-ctcgagaaataaactataactcccga-3' | (SEQ ID NO: 16) |
| 168C | 439-603ppr | 2 | E46F: 5'-ggatcccatatggttattcaggattatgac-3' | (SEQ ID NO: 15) |
| | | | HERP: 5'-ctcgagaaataaactataactcccga-3' | (SEQ ID NO: 16) |
| 158C | 449-603ppr | 2 | E56F: 5'-ggatcccatatgcaggaccgaccgac-3' | (SEQ ID NO: 21) |
| | | | HERP: 5'-ctcgagaaataaactataactcccga-3' | (SEQ ID NO: 16) |
| 148C | 459-603ppr | 2 | E66F: 5'-ggatcccatatgtcgcgccctttt-3' | (SEQ ID NO: 91) |
| | | | HERP: 5'-ctcgagaaataaactataactcccga-3' | (SEQ ID NO: 16) |
| 138C | 469-603ppr | 2 | 138CF: 5'-ggatcccatatggacgtgctttggctttctc-3' | (SEQ ID NO: 22) |
| | | | HERP: 5'-ctcgagaaataaactataactcccga-3' | (SEQ ID NO: 16) |
| NE2D | 394-603 | 2 | HEFP: 5'-ggatcccatatgcagctgttctactctcgtc-3' | (SEQ ID NO: 23) |
| | | | E2RD: 5'-gaattcttagggggctaaaacagc-3' | (SEQ ID NO: 24) |
| 217D | 390-603 | 2 | 217FP: 5'-ggatcccatatgtcggctggtggccag-3' | (SEQ ID NO: 25) |
| | | | E2RD: 5'-gaattcttagggggctaaaacagc-3' | (SEQ ID NO: 26) |
| 193D | 414-603 | 2 | E220F: 5'-ggatcccatatgacatctgtagagaatgctca-3' | (SEQ ID NO: 27) |
| | | | E2RD: 5'-gaattcttagggggctaaaacagc-3' | (SEQ ID NO: 28) |
| 178D | 429-603 | 2 | E235F: 5'-ggatcccatatgcatgacatcgacctcg-3' | (SEQ ID NO: 29) |
| | | | E2RD: 5'-gaattcttagggggctaaaacagc-3' | (SEQ ID NO: 30) |
| NE2I | 394-606 | 2 | HEFP: 5'-ggatcccatatgcagctgttctactctcgtc-3' | (SEQ ID NO: 31) |
| | | | E2RI: 5'-gaattcttatgcggaatgggggctaaaacag-3' | (SEQ ID NO: 32) |
| 217I | 390-606 | 2 | 217FP: 5'-ggatcccatatgtcggctggtggccag-3' | (SEQ ID NO: 33) |
| | | | E2RI: 5'-gaattcttatgcggaatgggggctaaaacag-3' | (SEQ ID NO: 34) |
| 193I | 414-606 | 2 | E220F: 5'-ggatcccatatgacatctgtagagaatgctca-3' | (SEQ ID NO: 35) |
| | | | E2RI: 5'-gaattcttatgcggaatgggggctaaaacag-3' | (SEQ ID NO: 36) |
| 178I | 429-606 | 2 | E235F: 5'-ggatcccatatgcatgacatcgacctcg-3' | (SEQ ID NO: 37) |
| | | | E2RI: 5'-gaattcttatgcggaatgggggctaaaacag-3' | (SEQ ID NO: 38) |
| 266N | 394-660 | 1 | HEFP: 5'-ggatcccatatgcagctgttctactctcgtc-3' | (SEQ ID NO: 39) |
| | | | HERP: 5'-ctcgagaaataaactataactcccga-3' | (SEQ ID NO: 16) |

TABLE 1-continued

PCR amplification template for the preparation of nucleotide encoding polypeptide of present invention and corresponding forward/reversed primers

| polypeptide | HEV ORF2 | position in template No. | forward primer (FP) and reversed primer (RP) | |
|---|---|---|---|---|
| 235N | 394-628 | 2 | HEFP: 5'-ggatccatatgcagctgttctactctcgtc-3'<br>235NR: 5'-gaattcttacgggcagaagtcatcg-3' | (SEQ ID NO: 40)<br>(SEQ ID NO: 41) |
| 225N | 394-618 | 2 | HEFP: 5'-ggatccatatgcagctgttctactctcgtc-3'<br>225RP: 5'-gaattcttaggcagggtagtccatgg-3' | (SEQ ID NO: 42)<br>(SEQ ID NO: 43) |
| 209N | 394-602 | 2 | HEFP: 5'-ggatccatatgcagctgttctactctcgtc-3'<br>209RP: 5'-gaattcttaggctaaaacagcaacc-3' | (SEQ ID NO: 44)<br>(SEQ ID NO: 45) |
| 208N | 394-601 | 2 | HEFP: 5'-ggatccatatgcagctgttctactctcgtc-3'<br>208RP: 5'-gaattcttataaaacagcaaccgc-3' | (SEQ ID NO: 46)<br>(SEQ ID NO: 47) |
| 207N | 394-600 | 2 | HEFP: 5'-ggatccatatgcagctgttctactctcgtc-3'<br>207RP: 5'-gaattcttaaacagcaaccgcg-3' | (SEQ ID NO: 48)<br>(SEQ ID NO: 90) |
| 203N | 394-596 | 2 | HEFP: 5'-ggatccatatgcagctgttctactctcgtc-3'<br>E203R: 5'-gaattcttaggaaatagagacgggac-3' | (SEQ ID NO: 49)<br>(SEQ ID NO: 50) |
| 193N | 394-586 | 2 | HEFP: 5'-ggatccatatgcagctgttctactctcgtc-3'<br>E220R: 5'-ctcgagttaagtggtgtaagtggaaatag-3' | (SEQ ID NO: 51)<br>(SEQ ID NO: 52) |
| 176N | 394-569 | 2 | HEFP: 5'-ggatccatatgcagctgttctactctcgtc-3'<br>E237R: 5'-ctcgagttacagttggtcactagcagt-3' | (SEQ ID NO: 53)<br>(SEQ ID NO: 54) |
| 280 | 380-660 | 1 | 227FP: 5'-ggatcccatatgctaggcggtctaccca-3'<br>HERP: 5'-ctcgagaaataaactataactcccga-3' | (SEQ ID NO: 55)<br>(SEQ ID NO: 16) |
| 270 | 390-660 | 1 | 217FP: 5'-ggatcccatatgtcggctggtggccag-3'<br>HERP: 5'-ctcgagaaataaactataactcccga-3' | (SEQ ID NO: 56)<br>(SEQ ID NO: 16) |
| 260 | 400-660 | 1 | 207FP: 5'-ggatcccatatgcccgtcgtctcagc-3'<br>HERP: 5'-ctcgagaaataaactataactcccga-3' | (SEQ ID NO: 57)<br>(SEQ ID NO: 16) |
| 247 | 414-660 | 1 | E220F: 5'-ggatcccatatgacatctgtagagaatgctca-3'<br>HERP: 5'-ctcgagaaataaactataactcccga-3' | (SEQ ID NO: 58)<br>(SEQ ID NO: 16) |
| 232 | 429-660 | 1 | E235F: 5'-ggatcccatatgcatgacatcgacctcg-3'<br>HERP: 5'-ctcgagaaataaactataactcccga-3' | (SEQ ID NO: 59)<br>(SEQ ID NO: 16) |
| 222 | 439-660 | 1 | E46F: 5'-ggatcccatatggttattcaggattatgac-3'<br>HERP: 5'-ctcgagaaataaactataactcccga-3' | (SEQ ID NO: 15)<br>(SEQ ID NO: 16) |
| 205 | 414-618 | 2 | E220F: 5'-ggatcccatatgacatctgtagagaatgctca-3'<br>225RP: 5'-gaattcttaggcagggtagtccatgg-3' | (SEQ ID NO: 60)<br>(SEQ ID NO: 61) |
| 201 | 459-660 | 1 | E46F: 5'-ggatcccatatggttattcaggattatgac-3'<br>HERP: 5'-ctcgagaaataaactataactcccga-3' | (SEQ ID NO: 15)<br>(SEQ ID NO: 16) |
| 191 | 469-660 | 1 | 138CF: 5'-ggatcccatatggacgtgctttggctttctc-3'<br>HERP: 5'-ctcgagaaataaactataactcccga-3' | (SEQ ID NO: 62)<br>(SEQ ID NO: 16) |
| 189 | 414-602 | 2 | E220F: 5'-ggatcccatatgacatctgtagagaatgctca-3'<br>209RP: 5'-gaattcttaggctaaaacagcaacc-3' | (SEQ ID NO: 63)<br>(SEQ ID NO: 64) |
| 188 | 414-601 | 2 | E220F: 5'-ggatcccatatgacatctgtagagaatgctca-3'<br>208RP: 5'-gaattcttataaaacagcaaccgc-3' | (SEQ ID NO: 65)<br>(SEQ ID NO: 66) |
| 183 | 414-596 | 2 | E220F: 5'-ggatcccatatgacatctgtagagaatgctca-3'<br>E203R: 5'-gaattcttaggaaatagagacgggac-3' | (SEQ ID NO: 67)<br>(SEQ ID NO: 68) |
| 173 | 414-586 | 2 | E220F: 5'-ggatcccatatgacatctgtagagaatgctca-3'<br>E220R: 5'-ctcgagttaagtggtgtaagtggaaatag-3' | (SEQ ID NO: 69)<br>(SEQ ID NO: 70) |
| 170 | 459-628 | 2 | E46F: 5'-ggatcccatatggttattcaggattatgac-3'<br>235NR: 5'-gaattcttacgggcagaagtcatcg-3' | (SEQ ID NO: 15)<br>(SEQ ID NO: 71) |
| C160 | 469-628 | 2 | 138CF: 5'-ggatcccatatggacgtgctttggctttctc-3'<br>235NR: 5'-gaattcttacgggcagaagtcatcg-3' | (SEQ ID NO: 72)<br>(SEQ ID NO: 73) |
| N160 | 459-618 | 2 | E46F: 5'-ggatcccatatggttattcaggattatgac-3'<br>225RP: 5'-gaattcttaggcagggtagtccatgg-3' | (SEQ ID NO: 15)<br>(SEQ ID NO: 74) |

TABLE 1-continued

PCR amplification template for the preparation of nucleotide encoding polypeptide of present invention and corresponding forward/reversed primers

| polypeptide | HEV ORF2 | position in template No. | forward primer (FP) and reversed primer (RP) | |
|---|---|---|---|---|
| 150 | 469-618 | 2 | 138CF: 5'-ggatcccatatggacgtgctttggctttctc-3' | (SEQ ID NO: 75) |
|  |  |  | 225RP: 5'-gaattcttaggcagggtagtccatgg-3' | (SEQ ID NO: 76) |
| 144 | 459-602 | 2 | E46F: 5'-ggatcccatatggttattcaggattatgac-3' | (SEQ ID NO: 15) |
|  |  |  | 209RP: 5'-gaattcttaggctaaaacagcaacc-3' | (SEQ ID NO: 77) |
| 142 | 459-600 | 2 | E46F: 5'-ggatcccatatggttattcaggattatgac-3' | (SEQ ID NO: 15) |
|  |  |  | 207RP: 5'-gaattcttaaacagcaaccgcg-3' | (SEQ ID NO: 92) |
| 134 | 469-602 | 2 | 138CF: 5'-ggatcccatatggacgtgctttggctttctc-3' | (SEQ ID NO: 78) |
|  |  |  | 209RP: 5'-gaattcttaggctaaaacagcaacc-3' | (SEQ ID NO: 79) |

\*: ppr represents a polypeptide has amino acid sequence -Pro-Pro-Arg added in direction of 5'-3' at the 3' terminus of position 603 amino acid, Pro, on C-terminus.

Example 2

Expression of Polypeptide 201

1 uL plasmid pTO-T7-ORF2-201 (0.15 mg/mL) was added into 40 uL competent cells of E. coli ERR2566 (generated under calcium chloride method) for transformation. Then the mixture was scrawled onto a kanamycin-LB plate, and the plate was incubated at 37° C. for 10-12 hours till the present of individual clones. The individual clones were picked and further inoculated in 4 mL LB culture medium in tubes, 220 rpm shaking at 37° C. for 10 hours, until the $OD_{550\ nm}$ value of the culture is about 1.5. Then 1 mL culture medium was stored at 4° C. for later use, and 2 uL 0.5 M IPTG was added into the rest 3 ml of culture medium (final content is 0.3 mM). The culture medium contain IPTG was keep on incubating at 37° C. for 4 hours with 220 rpm shaking for inducing the expression of polypeptide of interest. 1.5 mL induced culture medium was centrifuged at 12000 g for 30 seconds. The precipitated cells were re-suspended in 100 uL protein loading buffer (50 mM Tris Cl pH6.8, 100 mM DTT, 2% SDS, 0.1% Bromophenol Blue, 10% Glycerol), and further boiled for 10 minutes, then centrifuged at 12000 g for 10 minutes. 10 μl supernatant was load onto 12% SDS-PAGE for analysis of the expression of polypeptide 201. The clone which express in highest yield was used for future fermentation.

200 uL seek culture medium was added into 500 mL LB culture medium containing in 1 L Erlenmeyer flask. After incubating at 37° C. with 190 rpm shaking for about 11 hours till the $OD_{550\ nm}$ value of the culture reached 2.0, 300 uL 0.5 M IPTG was added to the final content is 0.3 mM. And the mixture was further incubated for 4 hours under aforementioned condition. 1.5 mL induced culture was centrifuged at 12000 g for 30 seconds. The cells were resuspended in 100 uL protein loading buffer, and boiled for 10 minutes, then centrifuged at 12000 g for 10 minutes. 10 ul supernatant was load onto 12% SDS-PAGE for analysis of expression of polypeptide 201. The result of the analysis of the SDS-PAGE (staining with Coomassie Brilliant blue R250) showed the expression of polypeptide 201 is about 35% of total expressed cell proteins as UVI gel imaging instrument shown (UVItech, model DBT-08).

Example 3

Purification of Polypeptide 201 Inclusion Body Expressed in E. coli

Figure 3:
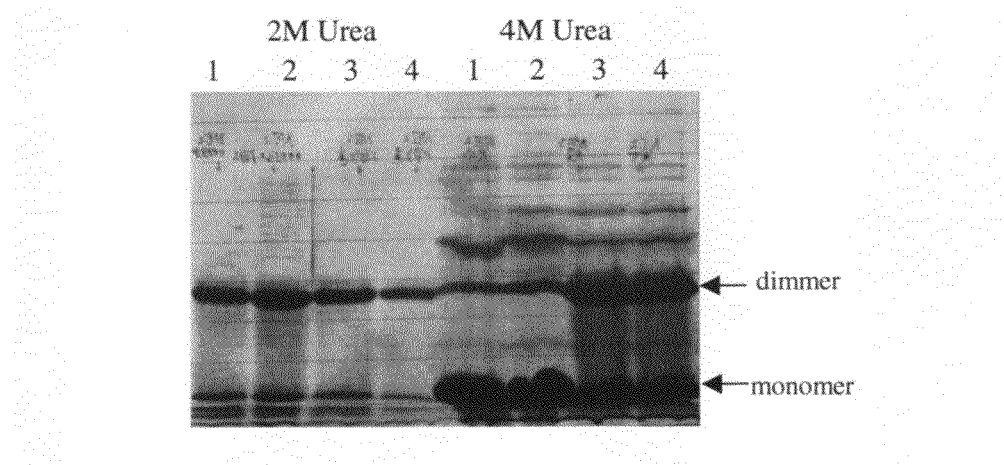
FIG. 3 shows the analysis results of Coomassie blue R250-stained 12% sodium dodecyl sulfate-polyacrylamide gel (SDS-PAGE) regarding 2 M and 4 M Urea solution of purified polypeptide 201 inclusion body from four batches of polypeptide 201, wherein said samples are obtained from recombinant E. coli embodying expression vector pTO-T7-ORF2-201. The results show that some of the polypeptide 201 had undergone renaturation to form dimer polypeptide with a proportion for the dimer polypeptide varied from 10% to 60%. The proportion for renatruation is lower than that of sample renatured in 1.times.PBS (20.times.PBS (1 L):$Na_2HPO_4$-12$H_2O$, 73.344 g; $KH_2PO_4$, 4 g; NaCl, 163.632 g; KCl, 4.024 g, pH7.45).

The culture medium of E. coli containing recombinant polypeptide 201 obtained in example 2 was centrifuged at 4000 rpm for 15 minutes, and each 500 mL culture's precipitate was re-suspended in 15 mL lysis buffer (50 mM Tris Cl, 10 mM EDTA and 300 mM NaCl in $dH_2O$, pH7.2). The cells were sonicated in ultrasonic instrument (Uilbra-Cell VCX500, SONICS&MATERIALS company, power 70%; 40 seconds on; 60 seconds off; sonicated for 20 minutes totally.). The sonicated mixture was centrifuged 12000 rpm for 10 minutes at 4° C., and the pellet was resuspended in buffer I solution (200 mM Tris Cl, pH8.5; 5 mM EDTA; 100 mM NaCl) containing 2% Triton-X100, and the final volume is the same as the original lysis. The mixture was shaking at 200 rpm for 30 minutes at 37° C., then centrifuged at 10000 rpm for 10 minutes at 4° C. The pellet was resuspended in equal volume of buffer I, and the mixture was sonicated (40 seconds on; 60 seconds off; power 70%; sonicated for 3 minutes totally). After that the mixture was centrifuged (10000 rpm) for 10 minutes at 4° C. The pellet was resuspended in buffer I containing 2% Triton-X100 to the final volume is the same as before. After the mixture was shake (200 rpm) for 30 minutes at 37° C., it was centrifuged (10000 rpm) for 10 minutes at 4° C. The pellet was resuspended in equal volume of buffer I, shaking (200 rpm) for 30 minutes at 37° C. Then the mixture was centrifuged 10000 rpm for 10 minutes at 4° C. The pellet was resuspended in buffer I which containing 2 M Urea to the final volume is the same as original mixture. After shaking 200 rpm for 30 minutes at 37° C., the mixture was centrifuged 10000 rpm for 10 minutes at 4° C. This supernatant is marked with 201-2M. The pellet was resuspended in buffer I containing 4M Urea to the final volume is the same as before. After shaking (200 rpm) for 1 hour at 37° C., the mixture was stored at 4° C. overnight, and then it was centrifuged 12000 rpm for 10 minutes at 4° C. This supernatant is marked with 201-4M. The purity of all the above samples is analyzed by 12% SDS-PAGE. The results are shown in FIG. 3.

Example 4

Renaturation of Recombinant Polypeptide 201

100 ml of sample 201-4 M prepared according to Example 3 was loaded into 2 dialysis bags (36 DM, retentate MW: 8000-10000, United Carbon Compound, U.S.A.) and dialyzed under stirring in a 1 L beaker, with 900 ml of 1×PBS (20×PBS (1 L) containing 73.344 g of Na2HPO4.12H2O, 4 g of KH2PO4, 163,632 g of NaCl, 4.024 g of KCl and pH 7.45) at 25° C. over night (10 hours), and then white precipitates were observed in the dialysis bags. Refreshing the dialysate and going on the dialysis, and then the dialysate was refreshed every 3 hours for 4 times. In principle, the content of urea in the sample would be $4 \times 10^{-6}$ M when the dialysis is over. The dialyzed sample was centrifuged at 25° C., 12000 rpm for 10 minutes; the supernatant was filtrated with 0.22 μm filter membrane for further purification; the pellet resuspended in 4 M urea/buffer I can be used in a new dialysis during which precipitates would also appear, but the concentration of the obtained protein sample would be lower than that of the first obtained sample.

Example 5

Purification of Recombinant Polypeptide 201 with Gel Filtration HPLC

The renatured 201 sample prepared according to the methods of Example 4 was further purified by HPLC as below:
Instrument: Beckman System Gold Nouveau 125NMP/166NMP HPLC,
Column: TSK GEL SW3000 21.5 mm×60 cm,
Elution: 1×PBS pH 7.45,
Flow Rate: 4 ml/min,
Detection: UV at 280 nm,
Sample: 2 ml of 4 M NE2 (8 mg/ml),
Collection: automatic apex collection of window mode,
Collection time: 1 tube/20 seconds,
Collection delay: 6 seconds.

The result shows that the molecule filtering is very effective in the chromatogram but that the apex component contains monomers and dimersas well as proteins distributed equably between them. After treated in boiling water for 10 minutes, the sample protein was analyzed by SDS-PAGE with 12% acrylamide for the monomer purity of the object protein peak, which is up to more than 95%. This demonstrates that in addition to self-aggregated, ORF2-201 monomer also aggregates with other small proteins and interactions occur also among the multimers which were eluted together during chromatogram.

Example 6

Characterization of the Recombinant Polypeptide Products of the Invention

The recombinant polypeptide of the invention was constructed and expressed according to the methods of Examples 1-5. Furthermore, each recombinant peptide was washed and dialyzed according to the methods of Examples 3-4. In table 2 the corresponding amino acid position of each recombinant peptide in hepatitis E virus, the renaturation property of the expressed recombinant products and the proportions of the monomers and dimers in their SDS-PAGE as well as the formation of the multimers are provided.

TABLE 2

Corresponding amino acids position of each recombinant peptide in hepatitis E virus, the renaturation property of the expressed recombinant products and the proportions of the monomers and dimers in their SDS-PAGE as well as the formation of the multimers.

| name of polypeptide | sequence no. | percent of monomer | percent of dimer | Multimerization | renaturable by dialysis |
|---|---|---|---|---|---|
| NE2 | SEQ ID NO: 2 | 10% | 90% | Yes | Yes |
| 193C | SEQ ID NO: 3 | 5% | 95% | Yes | Yes |
| 178C | SEQ ID NO: 4 | 100% | 0% | No | Yes |
| 168C | SEQ ID NO: 7 | 100% | 0% | No | Yes |
| 158C | SEQ ID NO: 8 | 60% | 40% | No | Yes |
| 148C | SEQ ID NO: 9 | 100% | 0% | No | Yes |
| 138C | SEQ ID NO: 10 | 100% | 0% | No | Yes |
| NE2I | SEQ ID NO: 1 aa394~aa606 | 5% | 95% | No | Yes |
| 217I | SEQ ID NO: 1 aa390~aa606 | 85% | 15% | No | Yes |
| 193I | SEQ ID NO: 1 aa414~aa606 | 100% | 0% | No | Yes |
| 178I | SEQ ID NO: 1 aa429~aa606 | 60% | 40% | No | Yes |
| NE2D | SEQ ID NO: 1 aa394~aa603 | 80% | 20% | No | Yes |
| 217D | SEQ ID NO: 1 aa390~aa603 | 20% | 80% | No | Yes |
| 193D | SEQ ID NO: 1 aa414~aa603 | 100% | 0% | No | Yes |
| 178D | SEQ ID NO: 1 aa429~aa603 | 100% | 0% | No | Yes |
| 235N | SEQ ID NO: 1 aa394~aa628 | 10% | 90% | No | Yes |
| 225N | SEQ ID NO: 1 aa394~aa618 | 4% | 96% | No | Yes |
| 209N | SEQ ID NO: 1 aa394~aa602 | 25% | 75% | No | Yes |

TABLE 2-continued

Corresponding amino acids position of each recombinant peptide in hepatitis E virus, the renaturation property of the expressed recombinant products and the proportions of the monomers and dimers in their SDS-PAGE as well as the formation of the multimers.

| name of polypeptide | sequence no. | percent of monomer | percent of dimer | Multimerization | renaturable by dialysis |
|---|---|---|---|---|---|
| 208N | aa394~aa601 SEQ ID NO: 1 | 100% | 0% | No | Yes |
| 207N | aa394~aa600 SEQ ID NO: 1 | 100% | 0% | No | No |
| 203N | aa394~aa596 SEQ ID NO: 1 | 100% | 0% | No | No |
| 193N | aa394~aa586 SEQ ID NO: 1 | 100% | 0% | No | No |
| 176N | aa394~aa569 SEQ ID NO: 1 | 100% | 0% | No | No |
| 247 | aa414~aa660 SEQ ID NO: 1 | 10% | 90% | No | Yes |
| 232 | aa429~aa660 SEQ ID NO: 1 | 10% | 90% | No | Yes |
| 222 | aa439~aa660 SEQ ID NO: 1 | 10% | 90% | No | Yes |
| 205 | aa374~aa618 SEQ ID NO: 1 | 10% | 90% | No | Yes |
| 201 | aa459~aa660 SEQ ID NO: 1 | 1% | 99% | No | Yes |
| 189 | aa414~aa602 SEQ ID NO: 1 | 2% | 98% | No | Yes |
| 188 | aa414~aa601 SEQ ID NO: 1 | 4% | 94% | No | Yes |
| 183 | aa414~aa596 SEQ ID NO: 1 | 100% | 0% | No | No |
| 173 | aa414~aa586 SEQ ID NO: 1 | 100% | 0% | No | No |

As shown in Table 2, the polypeptides of the invention which is included in the amino acid sequence of SEQ ID NO: 1 of HEV ORF2 has the ability to be well-renatured, which is intend to exhibits a dimensional structures close to natural HEV protein, when their carboxyl terminals locate between aa 601 (Leu) and aa 660 of SEQ ID NO: 1. Specifically, the peptides 247, 232, 222, 201, 235N, 225N, 209N, NE2I, 217D, 205, 189, 188, NE2 (SEQ ID NO:2) and 193C (SEQ ID NO: 3) was found to have expression bonds in the position corresponding to monomer molecule weight and 2 folds of monomer molecule weight while the amounts of dimers are apparently over those of monomers. NE2 and 193C was found to have obvious bonds in positions of bigger molecule weights, which suggests that said peptides tend to multimerize spontaneously.

After renaturable recombinant peptides in Table 2, 193C, 201, 208N, 209N, NE2, 222, 225N, 232 and 247, were further purified by Gel filtration HPLC and centrifuged each for 10 min at 20000 g and filtered with 0.1 μm $Al_2O_3$ filter membrane, the dynamic radiuses of these peptides was measured by dynamic light scattering instrument (DYNAPRO99-D-50 dynamic light scattering instrument, produced by PROTEIN SOLUTIONS) and their assemble status were speculated in Table 3. The obtained molecule radius of each recombinant peptide is apparently bigger than the predicted radius of the monomer. According to the putative molecule weights, it can be concluded that those peptides form at least dimers in the solution, and most of them form higher order multimers, which are in conformity with their behavior in SDS-PAGE. In fact, the polypeptides of the invention prepared with the above methods can form multimers of up to 180 or more monomers. It was further demonstrated that the polypeptides of the invention have unexpected property, i.e. above said recombinant peptides expressed by E. coli system tends multimerize spontaneously in PBS solution free of denaturing reagents and this is advantageous for increasing its immunogenicity as vaccine.

TABLE 3

Detection of the aggregate status of renaturable recombinant peptides of the invention by dynamic light scattering instrument.

| polypeptide | theoretical molecule weight of monomer (KD) | measured radius (nm) | putative molecule weight (KD) | Putative aggregate states |
|---|---|---|---|---|
| 193C | 21.2 | 3.44 | 47 | dimer (21.2 × 2 = 42.4) |
| 201 | 22.1 | 3.08 | 62.7 | trimer (22.1 × 3 = 66.3) |
| 208N | 22.9 | 3.57 | 66.1 | trimer (22.9 × 3 = 68.7) |
| 209N | 23 | 4.10 | 91. | tetramer (23 × 4 = 92) |
| NE2 | 24.4 | 4.04 | 90 | tetramer (24.4 × 4 = 97.6) |
| 222 | 24.4 | 3.72 | 73 | trimer (24.4 × 3 = 73.2) |
| 225N | 24.8 | 3.91 | 82 | trimer(74.4)tetramer(99.2) co-exsiting |
| 232 | 25.5 | 3.97 | 85 | trimer(25.5 × 3 = 76.5) |

TABLE 3-continued

Detection of the aggregate status of renaturable recombinant peptides of the invention by dynamic light scattering instrument.

| polypeptide | theoretical molecule weight of monomer (KD) | measured radius (nm) | putative molecule weight (KD) | Putative aggregate states |
|---|---|---|---|---|
| 247 | 27.2 | 4.28 | 101 | dimer(27.2 × 4 = 108.8) |
| 266N | 29.3 | 4.41 | 108 | tetramer(29.3 × 4 = 117.2) |

Example 7

The Physicochemical Properties of Polypeptide

Renaturation from the Inclusion Body

The inclusion body of the recombinant polypeptide prepared as described in examples 1-3 was denaturalized by 4 M urea, then dialyzed with over 100 volumes of PBS, as described in example 4. The dialysate was centrifuged at 12,000 rpm for 10 min. The supernatant contains some or all of the recombinant polypeptides, thereby demonstrating that said recombinant polypeptides are capable of renaturation.

The Polymerization of the Recombinant Peptides

Figure 4:
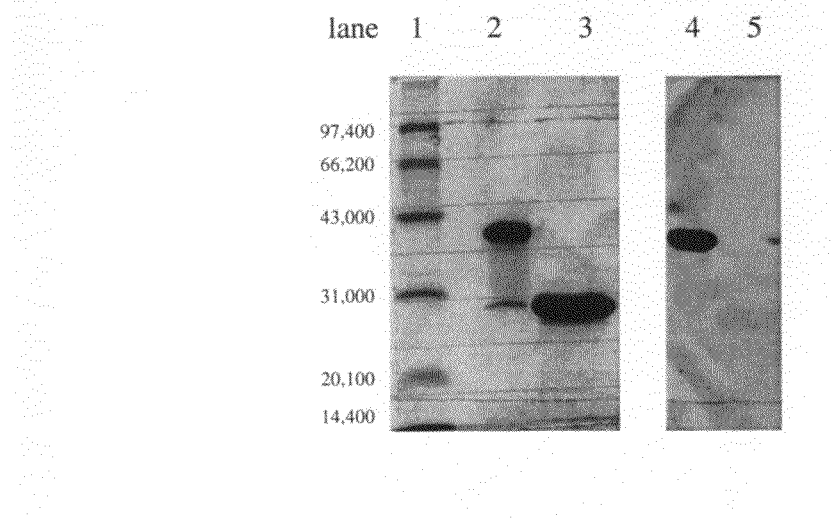
As shown in FIG. 4, percent of dimer is 99%.

In the analysis of the supernatant using conventional SDS-PAGE, the bands corresponding respectively to the monomer, dimer and polymer were identified. The specificity of said bands were further confirmed by conventional Western blotting, thereby demonstrating that recombinant polypeptide 201 forms a polymer after renaturation (see FIG. 4).

Figure 5:
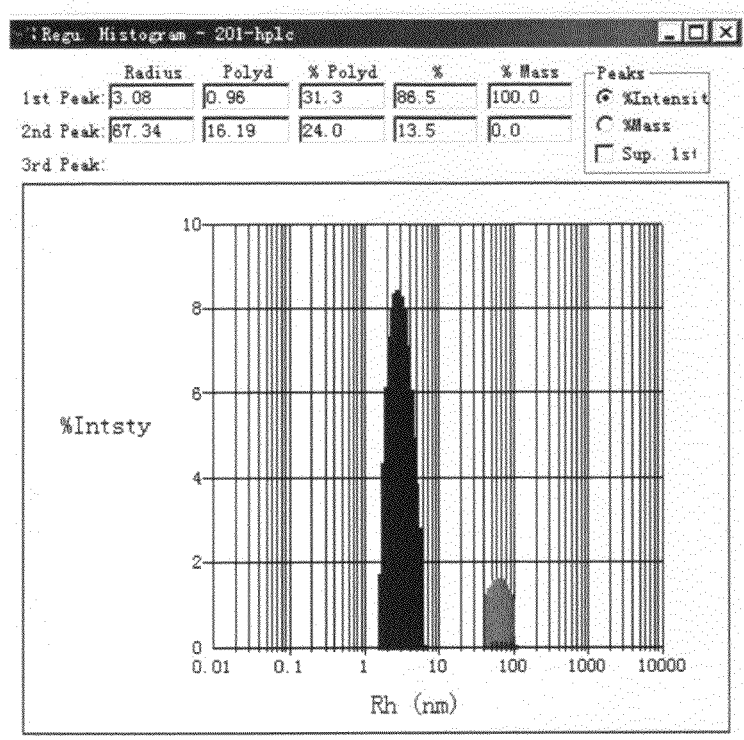
FIG. 5 shows the results from hydrated dynamic semi-diameter by dynamic light scattering instrument of aforementioned polypeptide 201, wherein polypeptide 201 is in advance purified by gel filtration HPLC, and centrifuged for 10 min under 20000 g, filtrated with 0.1 um filter membrane.

The Determination of the Molecular Size of Polypeptide 201 by Light-Scanning Technique According to Example 6, polypeptide 201 was centrifuged at 20,000 rpm for 10 min after purification with HPLC, then filtered with 0.1 um Millipore membrane of aluminia. The filtrate was measured by dynamic light-scanning instrument (DYNAPOR99-D-50, PROTEIN SOLUTION Corn. Ltd. U.S.A) at 824.0 nm. The Regulation algorithm was used for calculation, and its applicability was confirmed by many standard samples. The radius of the molecule is calculated from the dynamic radius corresponding to the % Intensity peak. The solvent was set as sample buffer PBS. The measured results shown in FIG. 5 indicated that the mean radius of polypeptide 201 in denaturant-free solution was 3.08 nm, with the calculated MW 62.7 KD (corresponding to the trimer). It is known to those skilled in the art that said polypeptide of the invention could actually form polymers of 180 monomers or more.

Example 8

Preparation of Mouse Anti-NE2 Monoclonal Antibodies

Establishment of the Hybridoma Cell Line

For the primary immunization, each Balb/C female mouse (6-8 weeks old) was inoculated with 5 ug recombinant antigen NE2 emulsified Freund's incomplete adjuvant (the total volume is 50 uL). Fifteen days later, the mouse was intramuscularly immunized for the second time with the same mount of NE2 emulsified in incomplete Freud's adjuvant. 30 days later, the mouse was then boosted intravenously (via the tail vein) with 5 ug antigens without the adjuvant. The mice were sacrificed 72-96 hours after booster immunization. The blood was then collected and the spleen was resected to prepare the suspension of the splenocyte (suspending in RPMI 1640 medium). The splenocytes were counted with a cell counter. Then the splenocytes were mixed in a 6:1 ratio with the SP2/0 mouse myeloma cells and centrifuged. The cells were fused with PEG(PEG 1500), then mixed with the equal volume of feeder cells, and transferred to 96-well plate (200 uL/well). At the atmosphere of 5% $CO_2$, the 96-well plate was incubated in a incubator (ESPEC BNA-31) at 37° C. 3 days later, half of the culture medium was replaced by flesh HT medium (1.361 mg hypoxanthn and 0.388 mg thymidine, with the addition of RPMI 1640 medium (GIBCO Int.) to 100 mL, dissolved at about 45-50° C. and filtrated for sterilization.). 7 days later, the 96-well plate was coated with NE2, and ELISA assay was performed on the hybridoma cell culture as described below. The cells positive to ELISA assay were cloned by limiting dilution means.

ELISA Assay 100 uL NE2 were purified by HPLC described in Example 5 at 37° C., and then dissolved in 0.05 mol/L CB(20.02 g $Na_2CO_3$ and 2.52 g $NaHCO_3$, with the addition of ddH.sub.2O to 1 L, pH9.5) to a final concentration of 0.3 ug/mL. The 96-well polyvinyl microtiter plate was treated with the resulting solution for 2 hours at 37° C. and then overnight at 4.degree. C. The microtiter plate was washed with PBST(8.0 g NaCl, 0.2 g $KH_2PO_4$, 2.9 g $Na_2HPO_4$ $12H_2O$, 0.2 g KCl and 0.5 mL Tween-20, (Poletheylene glycol sorbitan monolaurate, Polyoxyethylenesorbitan monolaurate), with the addition of $ddH_2O$ to 1 L, pH7.4) to remove the unabsorbed antigens. Then 200 uL blocking solution (2% glutin, 0.2% casein and 2% sucrose in 1×PBS) were added per well and incubated for 2 hours. Then pour off the solution, dry the well and store in vacuum at 4° C.

To assay, 100 uL cell culture were added to each well, and set one positive control (add 100 uL 1:100 diluted polyclonal anti-NE2 serum) and one negative control (add 100 uL HT medium) for each plate. After incubating at 37.degree ° for 30 min, the plate was washed with PBST (phosphate buffered saline TWEEN-20 (Polyethylene glycol sorbitan monolaurate, Polyoxyethylenesorbitan monolaurate))for 5 times and then dried. HRP-GAM (horsersdish peroxidase-goat anti mouse) Ig (DAKO company) was added and incubated for another 30 min at 37.degree. C. The plate was washed with PBS (phosphate buffered saline)—Tween-20 (Poltethylene glycol sorbitan monolaurate, Polyoxyethylenesorbitan monolaurate) again for 5 times and dried. 50 uL substrate solution A (13.42 g $Na_2HPO_4$ $12H_2O$, 4.2 g citric acid $H_2O$ and 0.3 g $H_2O_2$, with the addition of $ddH_2O$ to 700 mL) and 50 uL substrate solution B(0.2 g TMD and 20 mL dimethylformamide, with the addition of $ddH_2O$ to 700 mL) were added to the plate and incubated for 10 min at 37° C. 50 uL stop solution was used to terminate the reaction. The OD450 value of each well was read by an ELISA reader. In general, the OD450 value at least twice higher than that of the negative control can be considered as positive.

The Preparation of the Ascites and the Purification of the Monoclonal Antibodies Each 10-week-old Balb/C mouse was inoculated intraperitoneally with 0.5 mL incomplete Freud's adjuvant. 2-7 days later, the hybridoma cells were collected and centrifuged. Then discard the supernatant and add serum-free medium to the cells to a final concentration of $2\times10^5$-$2\times10^6$ cells/mL. 0.5 mL resulting suspension of the cells was used to inoculate each mouse. The ascites were harvested 7-10 days later when the abdomen of the mouse swelled, and then centrifuged for 15 min at 3,000 rpm. The clear liquid in the middle part of the tube was pipetted out and filtered with 0.45 um Millipore membrane for sterilization. The filtrate was stored at −20° C.

Dilute the treated ascites with the equal volume of PBS (81 mL 0.2 mol/L $Na_2HPO_4$ and 19 mL 0.2 mol/L $NaH_2PO_4$, with the addition of normal saline to 100 mL). $(NH_4)_2SO_4$ was then added dropwise with gently stirring until 50% saturation, and kept at 4° C. overnight. The solution was centrifuged(12,000 rpm) at 4° C. for 15 min, and the supernatant was discarded. The pellet was dissolved in PBS (2 volumes of the ascites used). $(NH_4)_2SO_4$ was added dropwise again to the resulting solution with stirring until 33% saturation, and kept overnight at 4° C. The solution was centrifuged (12,000 rpm) at 4° C. for 15 min, and the supernatant was discarded. The pellet was dissolved in PBS (2 volumes of the ascites used). $(NH_4)_2SO_4$ was added dropwise with gently stirring until 50% saturation, and kept at 4° C. overnight. The solution was centrifuged (12,000 rpm) at 4° C. for 15 min, and the supernatant was discarded. The pellet was then dissolved in proper amounts of PBS in a dialysis bag and dialyzed in 50-100 volumes of 120 mmol/L Tris-HCl buffer (containing 20 mmol/L NaCl, pH7.8) for about 12 hours at 4° C. with stirring. Replace the buffer for more than three times. The dialysate was stored at −20° C.

According to the method described above, monoclonal antibodies were prepared by immunizing Balb/C mice with polypeptide NE2 of the invention, and 8 anti-NE2 monoclonal antibodies were identified (1F6, 2C9, 3F5, 8C11, 8H3, 13D8, 15B2 and 16D7). Coat the eppendorf tubes with said 8 antibodies respectively, and test the capability of said antibodies binding native HEV by capture RT-PCR (see Example 9). As a result, 8C11, 8H3 and 13D8 shown significant activity of binding HEV, which indicated that their recognition sites were the native epitopes on the surface of the viral coating. Said three antibodies were used in Example 10.

Example 9

Testing the Capability of mAb Binding HEV by Antibody-Capturing RT-PCR

The 1.5 mL eppendorfs were irradiated by ultraviolet for 30 min, and then added 500 uL mAb 1:1000 diluted in CB (20.02 g $Na_2CO_3$ and 2.52 g $NaHCO_3$, with the addition of dd$H_2O$ to 1 L, pH9.5). After incubating overnight at 37° C., pour off the buffer, and add 1.5 mL blocking buffer (1×PBS with 2% albumin, pH7.4) to block 2 hours at 37° C. Then pour off the blocking buffer and add 500 uL 10% dejecta in sterilized normal saline which is positive for HEV. After reaction at 37° C. for 2 hours, wash the eppendorf with PBST for 6 times and then add 250 uL dd$H_2O$ to each eppendorf. The RT-PCR assay was then performed according to Example 14. As a result, the monoclonal antibodies of 8C11, 8H3 and 13D8 were capable of binding HEV, while 1F6, 2C9, 3F5, 15B2 and 16D7 were not capable of binding HEY.

Example 10

ELISA of the Polypeptides of the Present Invention with the Serum from Positive Rhesus Monkey, Serum from Human and Murine Derived Monoclonal Antibodies and the Dot Blotting of the Polypeptides of the Present Invention with Murine Derived Monoclonal Antibodies ELISA of the Recombinant Polypeptide with Serum from Positive Rheseus Monkey, Serum from Human and Murine Derived Monoclonal Antibodies The polypeptides of the present invention shown in Table 2 are produced and purified according to the methods mentioned in examples 1-6. The resulted purified recombinant protein samples with concentration of 1 mg/ml are diluted 1:500 with PBS buffer (20Mm, pH7.4), and coated 100 μl/well on the 96-well microtitre plate under the following condition: incubation at 37° C. for 2 hours and then incubation overnight for about 12 hours at 4° C. After washing once with PBS-Tween20 washing solution (8.0 g NaCl, 0.2 g $KH_2PO_4$, 2.9 g $Na_2HPO_4.12H_2O$, 0.2gKCl and 0.5 ml Tween20 (Polyethylene glycol sorbitan monolaurate, Polyoxyethylenesorbitan monolaurate), adding non-ionic $H_2O$ to final volume 1 L, pH7.4) on the automatic washer (TECAN, M12/4R Columbus plus), and drying, blocking solution (2% glutin, 0.2% casein and 2% sucrose in PBS) was added, 200 μl/well, incubation at 37° C. for 30 mins. Then the properly diluted anti-serum or monoclonal antibody was added, at 37° C. for 30 mins. After washing 5 times with PBS-Tween20 (Polyethylene glycol sorbitan monolaurate, Polyoxyethylenesorbitan monolaurate)washing solution on the automatic washer at 20 seconds interval and drying, the properly diluted HRP-labelled second antibody (goat anti-human, mouse IgG antibody) was added, at 37° C. for 30 mins. After washing 5 times with PBS-Tween20 (Polyethylene glycol sorbitan monolaurate, Polyoxyethylenesorbitan monolaurate)washing solution on the automatic washer at 20 seconds interval and drying, a drop of each of the chromogenic agent A and B (A: 13.42 g $Na_2HPO_4.12H_2O$, 4.2 g citric acid. $H_2O$ and 0.3 g $H_2O_2$, adjusting the volume to 700 ml with non-ionic water; B: 0.2 g TMB, 20 ml dimethylfoiniamide, adjusting the volume to 700 ml with non-ionic water) was added to develop color at 37° C. for 10 mins. A drop of the stop solution (2M $H_2SO_4$) was added. The $OD_450$ nm was measured on a microplate reader (TECAN, Sunrise Remote/Touch Screen) (with reference wavelength of 620 nm). 3 times of the mean value of the negative control was set as the positive threshold value, and the result is positive when the OD value thereof is higher than the threshold value.

Dot Blotting of the Polypeptides of the Present Invention with Various Murine Derived Monoclonal Antibodies 10 .mu.l (1 mg/ml) of each of the polypeptides listed in Table 2 which were produced according to the methods of examples 1-5 and purified by HPLC gel filtration was dotted respectively and slowly on the nitrocellulose membrane and air-dried. After blocking with 5% skim milk for 1.5 hours at room temperature, various murine derived monoclonal antibodies produced as mentioned in example 8 (the cell supernatant secreted by monoclonal B lymphocytes at 1:100 dilution with 5% skim milk) were added, reacting at room temperature for 1 hour. Then the membrane was washed 3 times using TNT (10 mM Tris.Cl, pH8.0, 150Mm NaCl, 0.05% Tween20 (Polyethylene glycol sorbitan monolaurate, Polyoxyethylenesorbitan monolaurate)) at 5 mins interval. The HRP-labelled Goat anti-mouse IgG (produced by JING-MEI Biological Company, diluted in 1:1000 with 5% skim milk) was added, and reacted at room temperature for 1 hour. After washing 3 times with TNT at 5 mins interval, NBT/BLIP($C_4OH_3ON_{10}O_6Cl_2/C_8H_6BrClNO_{.4}P.C_7H_9N$) was added to develop color. The dots were scanned with gel imagining system and diverted into the values of grey degree and divided into five positive grades as ++++, +++, ++, +, +− and negative grade as −. Compared with classic Western blotting, this method can reflect more really the immunoreactivity in the absence of denaturing agent due to not subject to be denatured with SDS (sodium dodecyl sulfate).

TABLE 4

The reactivity of polypeptide of present invention against murine derived monoclonal antibody, serum from HEV patient in recovery phase, and serum from HEV-infected rhesus monkey in acute phase

| poly-peptide | ELISA | | dot blotting | | | | | |
|---|---|---|---|---|---|---|---|---|
| | monkey serum | human serum | 8C11 | 8H3 | 13D8 | 8C11 | 8H3 | 13D8 |
| NE2 | ++ | ++ | +++ | ++ | +++ | ++++ | ++ | +++ |
| 193C | ++ | ++ | +++ | + | ++ | ++ | ++ | ++ |
| 178C | + | ++ | +++ | +− | +++ | ++ | ++ | ++ |
| 168C | − | +− | ++ | − | +++ | +/− | +/− | +/− |
| 158C | +− | + | + | − | +++ | + | +/− | +/− |
| 148C | + | ++ | − | − | − | +/− | +/− | +/− |
| 138C | − | − | − | − | − | +/− | +/− | +/− |
| NE2I | +++ | ++ | + | +++ | +++ | +++ | ++ | +++ |
| 217I | + | + | ++ | − | ++ | + | + | + |
| 193I | ++ | ++ | ++ | − | ++ | +++ | ++ | +++ |
| 178I | +++ | ++ | ++ | − | ++ | ++ | ++ | ++ |
| NE2D | ++ | ++ | ++ | − | ++ | + | + | + |
| 217D | ++ | ++ | ++ | − | ++ | + | + | + |
| 193D | ++ | ++ | ++ | − | ++ | + | + | + |
| 178D | ++ | ++ | +++ | − | +++ | + | + | + |
| 235N | ++ | +− | +++ | +− | +++ | +++ | + | +++ |
| 225N | +++ | +++ | +++ | +− | +++ | ++++ | + | +++ |
| 209N | ++ | ++ | +++ | + | +++ | ++++ | + | +++ |
| 208N | + | +++ | +++ | − | +++ | ++ | + | ++ |
| 207N | − | − | − | − | − | ++ | + | + |
| 203N | − | − | − | − | − | ++ | + | + |
| 193N | − | − | − | − | − | ++ | + | + |
| 176N | − | + | − | − | − | + | +/− | + |
| 247 | | +++ | + | +++ | ++++ | +++ | ++++ |
| 232 | | +++ | + | +++ | ++++ | ++++ | ++++ |
| 222 | | +++ | +− | +++ | ++++ | ++ | ++++ |
| 205 | ++ | + | +++ | − | +++ | +++ | ++ | ++ |
| 201 | | +++ | + | ++ | ++++ | ++ | ++++ |
| 189 | − | +− | +++ | − | +++ | ++ | ++ | ++ |
| 188 | − | +− | ++ | − | +++ | ++ | ++ | ++ |
| 183 | − | + | +− | − | +− | ++ | ++ | ++ |
| 173 | − | − | − | − | − | ++ | + | ++ |
| 170 | | +++ | − | +++ | ++++ | +++ | ++++ |
| C160 | | − | − | − | − | − | − |
| N160 | | ++ | − | ++ | ++ | − | ++ |
| 150 | | − | − | − | − | − | − |
| 144 | | ++ | − | ++ | ++ | − | ++ |
| 142 | | − | − | − | − | − | − |
| 134 | | − | − | − | − | − | − |

Result

Respectively, the purified recombinant polypeptides listed in Table 4 were coated on microtitre plate, and the reactivities thereof to three murine derived monoclonal antibodies 8C11, 8H3 and 13D8 mentioned in example 8, serum of HEV patient in recovery phase and serum from HEV-infected rhesus monkey in acute phase were examined by ELISA, and the reactivities thereof to the used three monoclonal antibodies were examined by Dot blotting assay. The results showed that the polypeptides NE2, 193C, 178C, NE2I,235N, 225N, 209N, 247, 232, 222 and 201 had better reactivities to each of the serum/monoclonal antibody. This suggested that the polypeptides had better native HEV epitope and can be used to diagnostic kit and/or vaccine for HEV.

The polypeptides 138C, C160, 150, 142 and 134 had poor reactivities to various antibodies. It showed that the formation of the major native epitope ORF2 involved at least the fragment of aa469 to aa600.

The sequences of the polypeptides 170, C160, N160, 150, 144, 142 and 134 were those that aa459-aa628, aa469-aa628, aa459-aa618, aa469-aa618, aa459-aa602, aa459-aa600 of the ORF2 were linked respectively to the initial amino acid (Met).

Example 11

Figure 6:
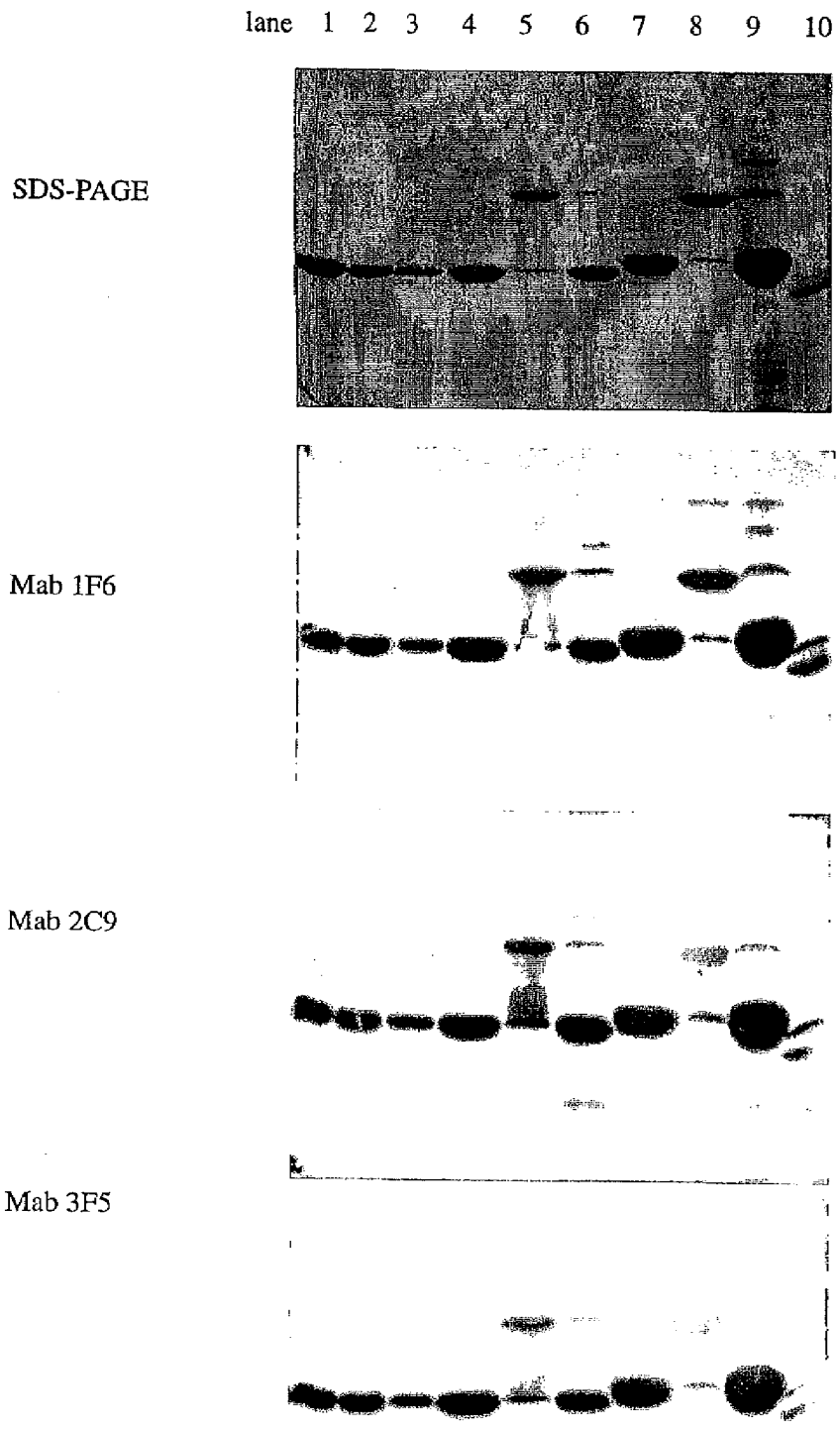
FIG. 6 shows Western blot results of the reaction of polypeptide 208N, 209N and 225N with mouse Mab 1F6, 2C9 and 3F5. Lanes 1, 2, 3, respectively, corresponds to the renatured sample being treated in boiling water bath for 10 min, renatured sample and the precipitated renatured samples of polypeptide 208N; Lanes 4, 5, 6, respectively, corresponds to the renatured sample being treated in boiling water bath for 10 min, renatured sample and the precipitated renatured samples of polypeptide 209N; Lanes 7, 8, 9, respectively, corresponds to the renatured sample being treated in boiling water bath for 10 min, renatured sample and the precipitated renatured samples-of polypeptide 225N; and Lane 10 is monomer polypeptide 201 as control.
Figure 7:
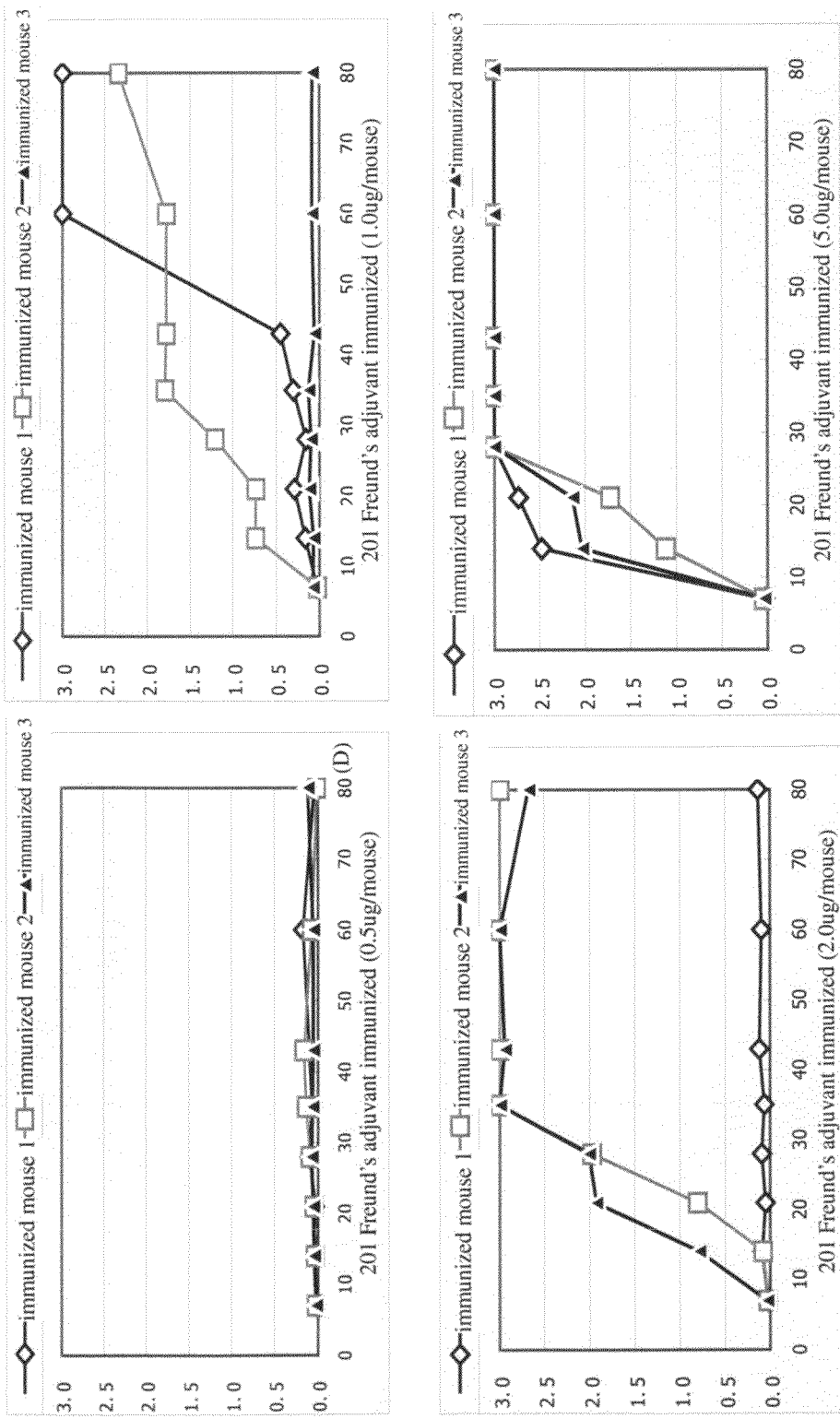
FIG. 7 illustrates the profile of HEV antibodies raised in sera from mice following immunization with vaccine of polypeptide 201 (containing Feund's adjuvant) in various dosages. The horizontal coordinate is defined as the days after the first immunization. The vertical coordinate is defined as the $OD_{450\ nm/620\ nm}$ measured by ELISA.

The Western Blotting of the Polypeptides of the Present Invention with Murine Derived Monoclonal Antibodies The Western blotting of the polypeptides 208N, 209N and 225N of the present invention produced as mentioned in examples 1-5 with murine derived monoclonal antibodies 1F6, 2C9, 3F5 produced in example 8 was carried out. The said polypeptides were separated by SDS-PAGE, then transferred to nitrocellulose membrane according to the conventional methods and 5% skim milk was added for blocking 1.5 hours; various murine derived monoclonal antibodies (the cell supernatant secreted by monoclonal B lymphocytes at 1:100 dilution with 5% skim milk) were added, reacting at room temperature for 1 hour; after washing 3 times at 5 mins interval, anti-mouse IgG labeled with HRP (at 1:1000 dilution with 5% skim milk) was added, room temperature for 1 hour; after washing 3 times with TNT at 5 mins interval, NBT/BCIP were added to developed color. The results of Western blotting are shown in FIG. 6. The results show that the polymer bands, in particular in lane 8, which cannot be observed by the staining of Coomassie Brilliant Blue R250, can be observed due to the enzyme-linked amplifying effect of Western blotting assay. It is further confirmed that the recombinant polypeptide 208N of the present invention does not form into polymer during 12% SDS-PAGE, and that the monoclonal antibody 1F6 has stronger activity to 209N and 225N compared with the monoclonal antibodies 2C9 and 3F5.

Example 12

Preparation of the Vaccine Containing Polypeptide 201 and the Assay of the Immunizing Mouse with it Preparation of the Vaccine Containing Polypeptide 201 with Freund's Adjuvant The polypeptide 201 of the present invention produced as above-mentioned and purified by HPLC (purity >95% and the concentration of the protein 1.02 mg/ml) was diluted with PBS, and the equivalent volume of complete Freund's adjuvant (containing BCG) was added to reach a desired final concentration of the polypeptide 201 (for example, if each mouse was desired to be immunized 100 μl, 5 μg, the concentration of the polypeptide 201 would be prepared into 0.05 mg/ml). The solution was mixed and emulsified for 30 mins until no separating liquid phase appeared after keeping still for 30 mins.

Using Freund's adjuvant as vaccine adjuvant, four groups mice (each group of 3 Kunming White mice), each was injected intramuscularly with 0.5, 1, 2, 5 μg in 100 μl/mouse according to the immunizing schedule of 0, 7, 28 days. The results were shown in F1G. 7. The results indicated that ORF2-201 vaccine prepared with Freund's adjuvant with does above 2 μg had very strong immunogenicity, and the antibody was started to produce at the second week after immunization and to reach the highest titre at the forth week. It is thought that the antibody with higher titre can be produced only in the mice immunized with protein antigen at the does of 30-70 μm/mouse according to the common books and literatures on immunology. Therefore, the results show that the vaccine, the polypeptide 201 of the present invention combined with Freund's adjuvant, has remarkably high immunogenic effect compared with the available vaccine.

Preparation of the Vaccine Containing the Polypeptide 201 with Aluminum Adjuvant A desired amount of the original aluminum adjuvant (A13+ 13.68%, Na+3.36%, pH5.55), which was from the Lanzhou Biological Product Institute of China, was adjusted with 1 N NaOH till to produce precipitate. After mixing completely, 1×PBS was added to reach the double volume. Then centrifuge was performed at 10,000 for 1 min, and the supernatant was discarded. The precipitate was resuspended with 1×PBS to the double volume again, and centrifuged at 10,000 for 1 min and the supernatant was discarded. Such process was repeated several times until the pH reached 7-7.4. Finally, the precipitate was resuspended with equal volume of 1×PBS, and the solution was sterilized and stored at 4° C., and used as 9× store solution.

Similarly, the polypeptide 201 produced as above-mentioned and purified by HPLC (purity >95% and the concentration of the protein 1.02 mg/ml) was diluted with PBS, and the ⅑ volume of aluminum adjuvant was added to reach a desired final concentration of the polypeptide 201, and mixed overnight at 4° C. The immunized does is 100 μl/mouse. Using aluminum adjuvant as vaccine adjuvant, each group of 3 Bal b/c mice, each was injected intramuscularly with 2, 5, 10 μg/mouse according to the immunizing schedule of 0, 7, 28 days. The results were shown in FIG. 9. The results indicated that the does of 5, 10 μg/mouse has better immunogenic effect, which is comparable to that of the available HBV surface antigen vaccine currently, which is a particulate antigen and is thought to have better immunogenicity compared with the monomer antigen. Therefore, the results show that the polymer of the present invention is useful for the vaccine.

The Immunity Assay of the Polypeptide 201 without Adjuvant

Figure 8:
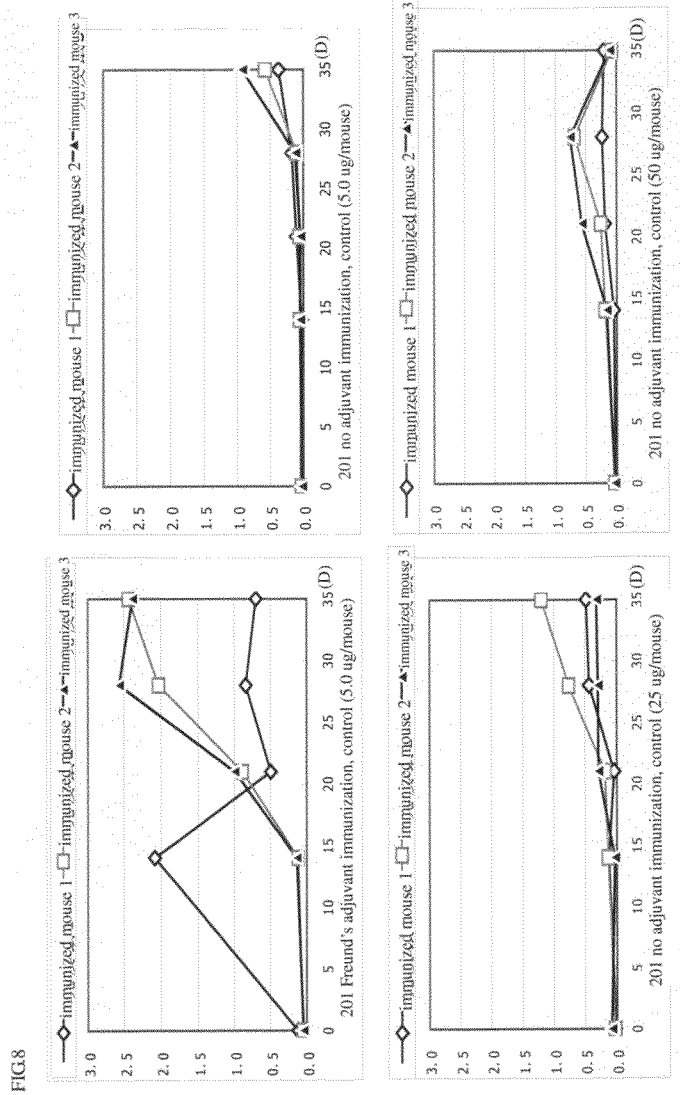
FIG. 8 illustrates the profile of HEV antibodies raised in sera from mice following immunization with vaccine of polypeptide 201 (containing no adjuvant) in various dosages. The horizontal coordinate is defined as the days after the first immunization. The vertical coordinate is defined as the $OD_{450\ nm/620\ nm}$ of ELISA.
Figure 10A:
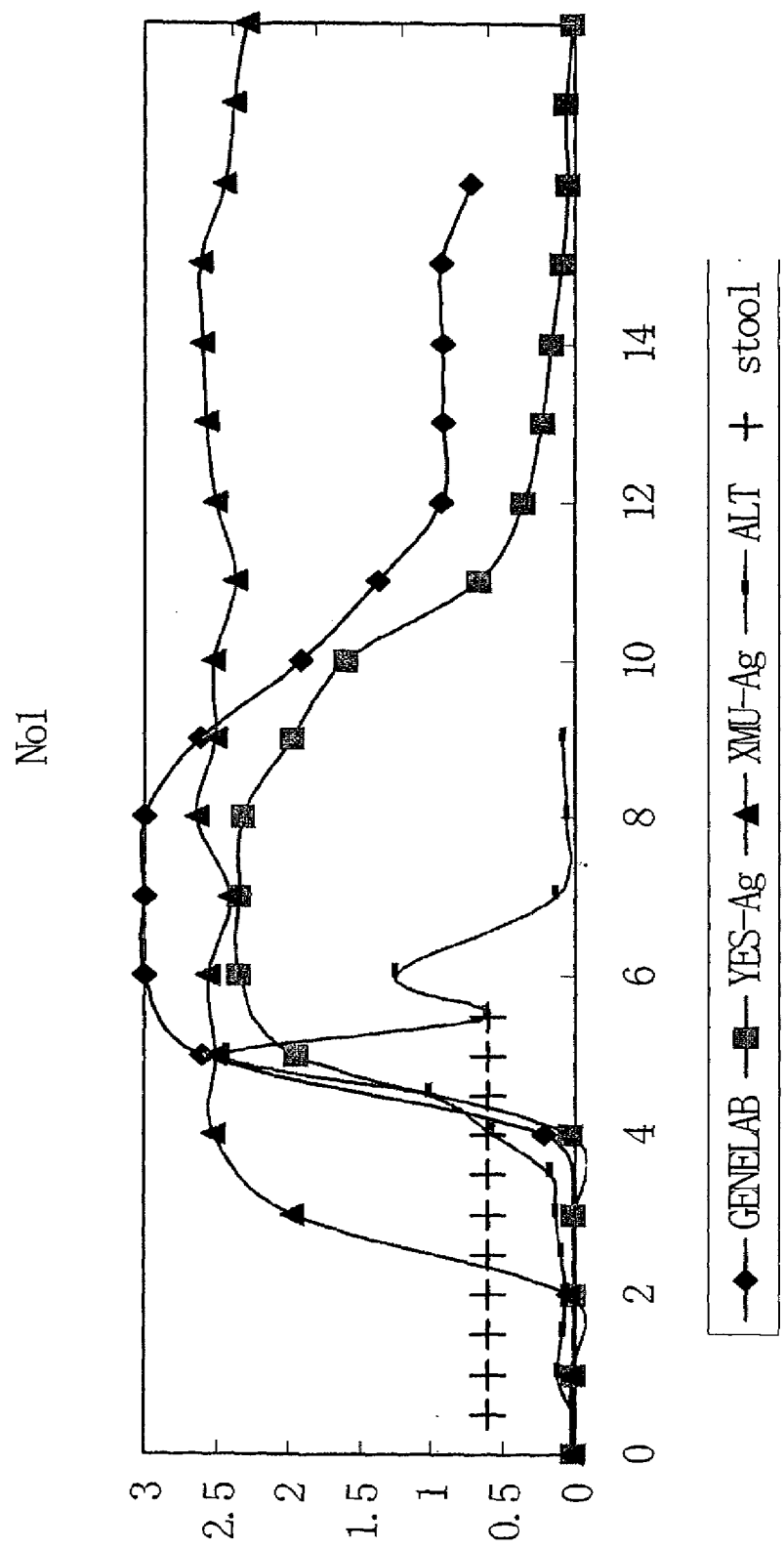
FIGS. 10 A, 10B, 10C and 10D show the profile of HEV antibodies raised in sera from rhesus monkeys grouped No. 1, No. 2, No. 3 and No. 13, respectively. All these subjected animals are challenged with HEV by intravenous injection. The horizontal coordinate is defined as the days after the first immunization. The vertical coordinate is defined as the $OD_{450\ nm/620\ nm}$ of ELISA. The results illustrate the anti-NE2I-IgG is present 5-10 days earlier than GENELABS-IgG, and WANTAI anti-HEV-IgG in sera of monkeys in group No. 1, No. 2, and No. 3; the anti-NE2I-IgG is detectable in sera of No. 13 monkeys, and no Genelabs anti-HEV-IgG and WANTAI anti-HEV-IgG can be detected in sera of N0.13 monkeys.
Figure 10B:
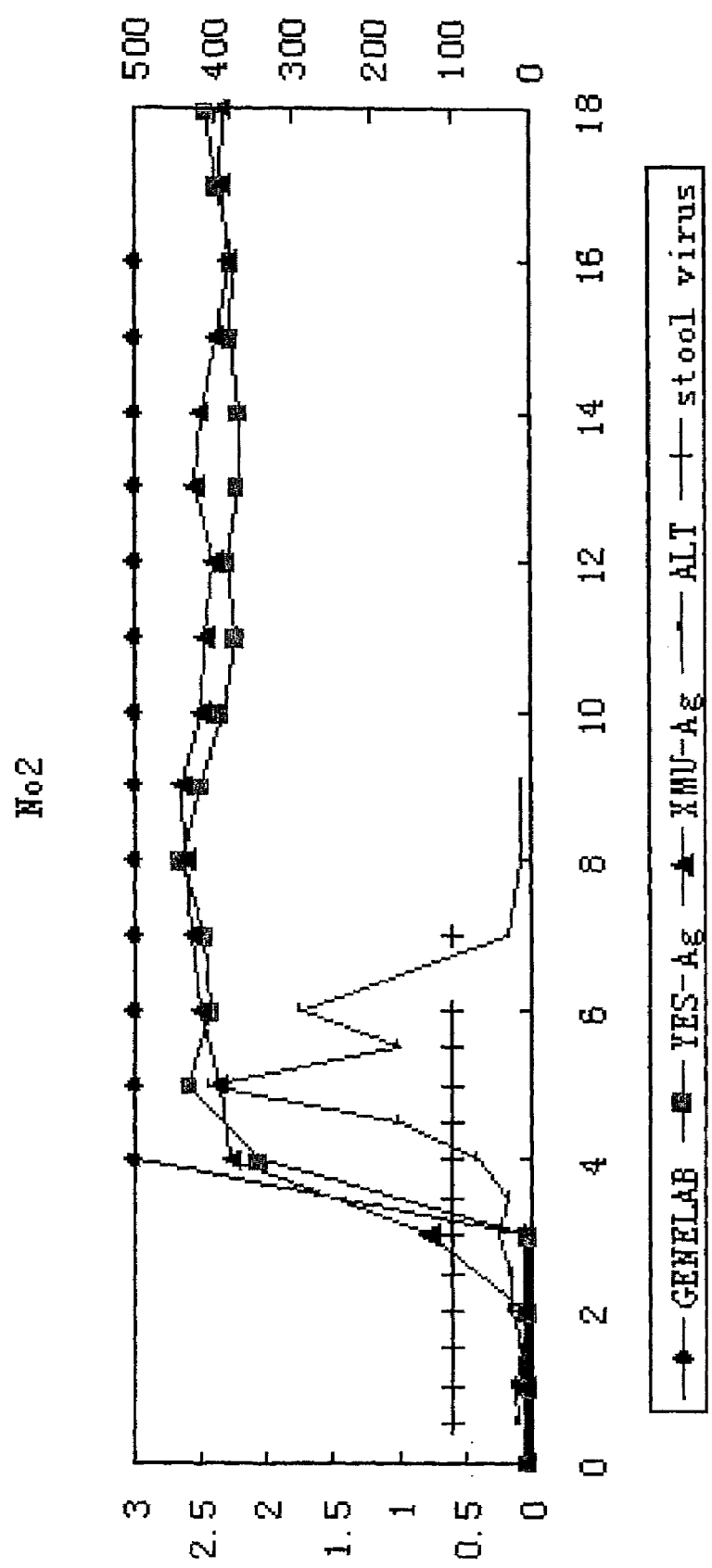
Figure 10C:
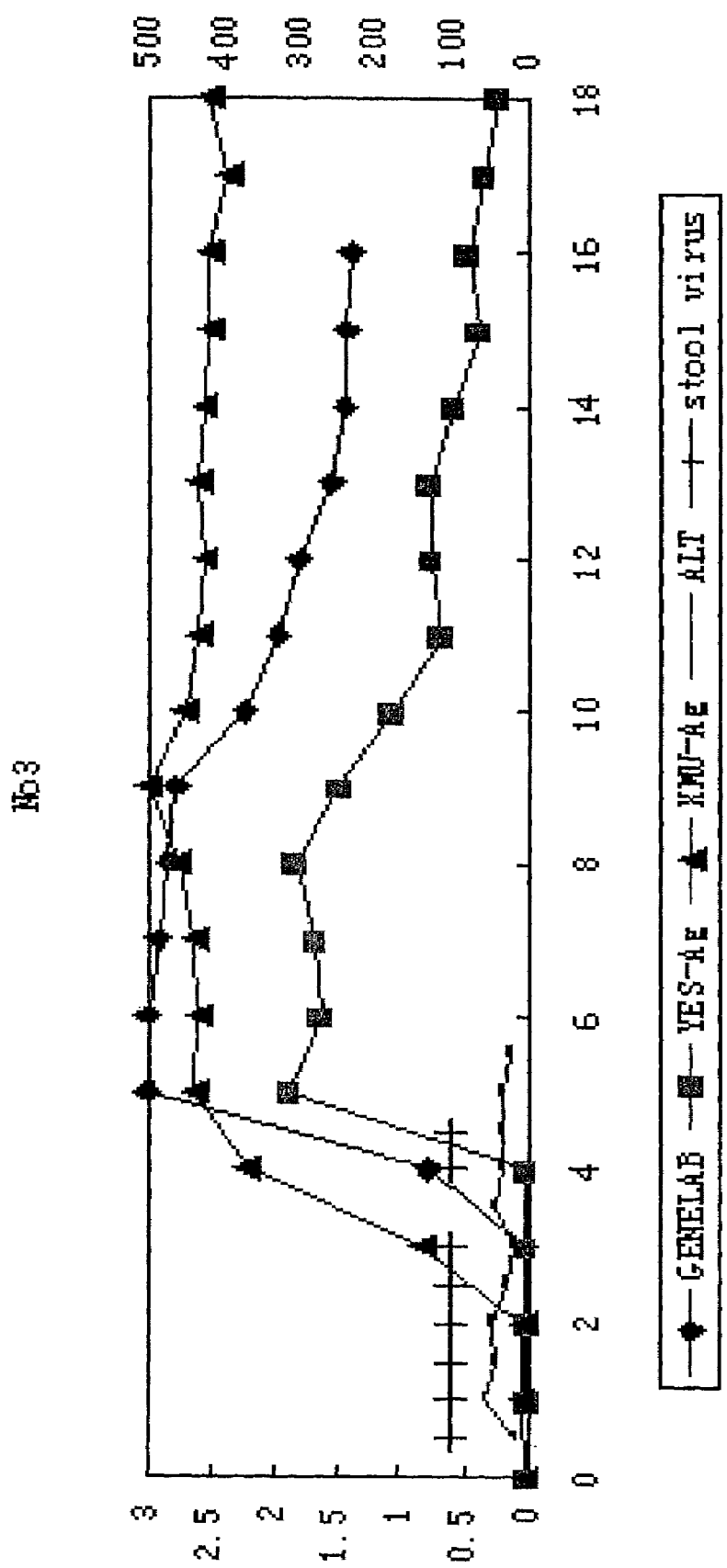
Figure 10D:
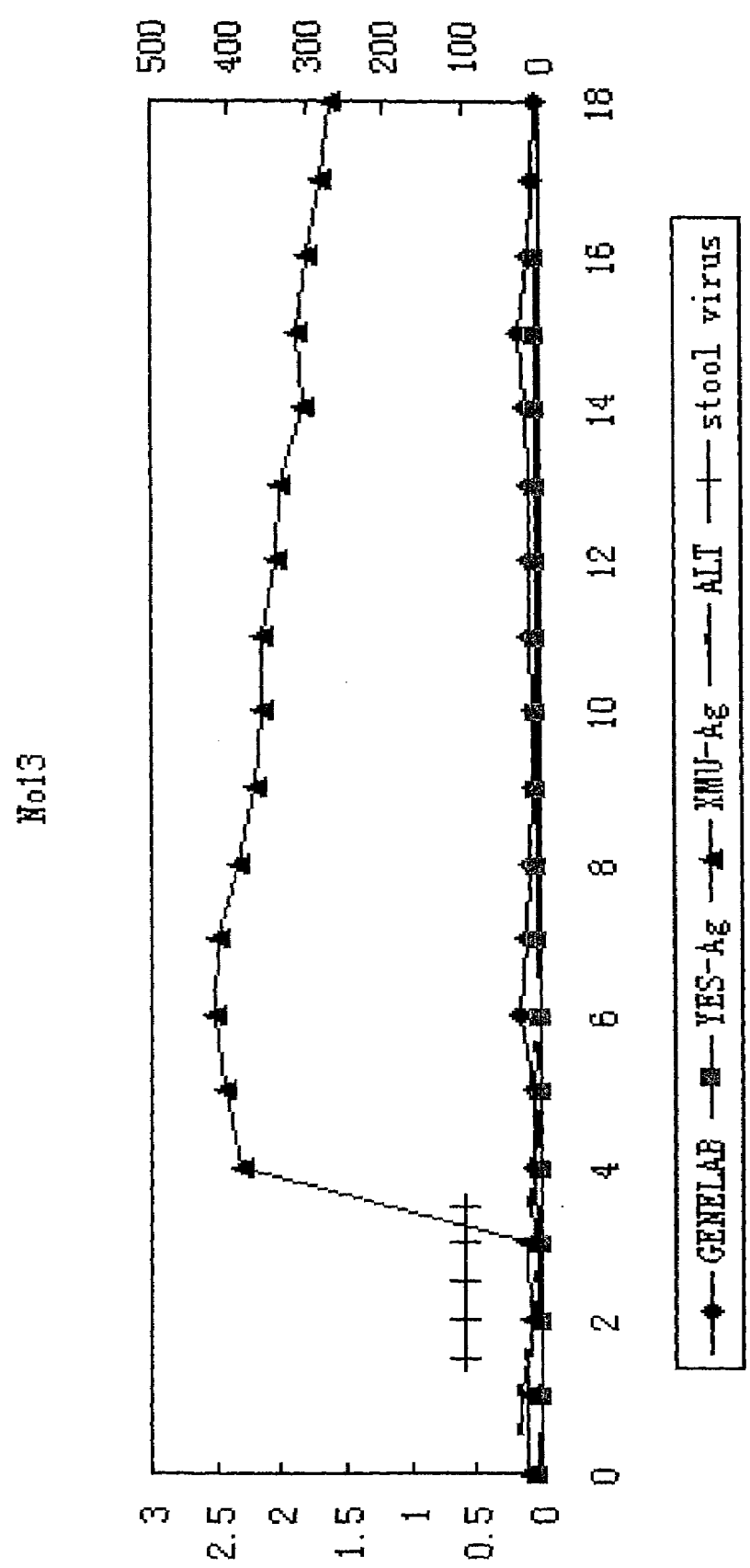

The polypeptide 201 obtained as above-mentioned was solved in 4 M urea, and the supernatant was dialyzed with PBS (pH7.45) to renature, with the purity of about 95%. Using Freund's adjuvant as vaccine adjuvant, each group of 3 Kunming White mice, each was injected intramuscularly with 5, 25, 50 μg/mouse (the control group with 5 μg /mouse) according to the immunizing schedule of 0, 7, 28 days. The results were shown in FIG. 8. The results indicated that the remarkable antibodies were produced in the mice immunized with non-adjuvant ORF2-201 vaccine, and the used dosage thereof was comparable to that conventional antigen with Freund's adjuvant. It further shows that the polymer polypeptide of the present invention has higher immunogenicity compared with the conventional antigen.

It may be concluded from the above results that the Balb/c mice can be elicited to produce specific antibody when immunized with both the recombinant polypeptide 201 and NE2 (5 μg/mouse), regardless of the formulation of Freund's adjuvant or aluminum adjuvant. And other renaturable polypeptides formulated with Freund's adjuvant can also elicit the mice to produce specific antibodies. Therefore, the polypeptides of the present invention have the good properties to use as vaccine.

Example 13

Immunization of Rhesus Monkeys with the Vaccine Comprising a Recombinant Polypeptide of the Present Invention Six rhesus monkeys with normal ALT and negative HEV were selected and divided into two groups, one group designated HF1, HF2 and HF3 and the other group designated HF4, HF5 and HF6. The two groups of the subject rhesus monkeys were vaccinated by intradeltoidal injection with the aluminum adjuvant containing polypeptide NE2I vaccine and polypeptide 201 vaccine prepared as described in the examples 1-5 and 12 at the dosages of 20 μg, respectively. Such vaccinations were carried out on days 0, 10, and 30 respectively. Three weeks after the last vaccination, the titers of the anti-NE2I IgG antibody from the animals were tested by indirect ELISA with the results as follows: HF1(1:16000), HF2(1:4000), HF3(1:8000), HF4(1:2000), HF5(1:3000) and HF6(1:5000).

The above results illustrated by polypeptides NE2I and 201 indicated that the recombinant polypeptides of the invention have better immunogenicity compared with HEV ORF2 polypeptide trpE-C2 (amino acids 225-660 of SEQ ID NO: 1) used as immunogen in U.S. Pat. No. 5,885,768. In U.S. Pat. No. 5,885,768, Reyes, et al. vaccinated 4 cynomolgus monkeys by intravenous injection with 50 ug of HEV ORF2 polypeptide trpE-C2 expressed from *E. coli* in combination with an improved aluminum adjuvant on days 0 and 30 respectively. Two cynomolgus monkeys injected with adjuvant alone were used as control. No antibody to HEV was detected in the group of the vaccinated monkeys 4 weeks after the second vaccination. Two of these vaccinated monkeys were selected to receive a third vaccination with 80 ug of insoluble trpE-C2 polypeptide without adjuvant on day 58, and the anti-HEV antibody was detected only 4 weeks later.

Example 14

Challenging with HEV of the Rhesus Monkeys Immunized with Vaccine Comprising the Recombinant Polypeptide of the Present Invention Preparation and Quantification of Hepatitis E Virus (HEV)

A fecal from a HEV patient from Xinjiang, China, was formulated to 10% suspension in sterile physiological saline solution. The suspension was centrifuged at 12000 g for 20 minutes at 4° C., and the supernatant was filter-sterilized with 0.2 μm sterile filter (NALGENE® Cat. No. 190-2520). HEV in a PCR-detectable amount was used as an infection dosage.

Extraction, reverse transcription and PCR of RNA of HEV from fecal: HEY RNAs were extracted from the 10% fecal suspension using Trizol reagent (GIBCOL) according to its manipulation instructions, and were subjected to reverse transcription in a 20 μl reaction volume at 42° C. for 40 minutes with the specific primer A3 (4566-4586, 5'-ggctcaccggagt-gtttcttc-3') (SEQ ID NO:80)as RT primer using AMV reverse transcriptase. Then, the first round of RT-PCR was carried out in a final volume of 20 ul using 2 ul RT product as template and using A3 primer and AS primer (4341-4362, 5'-ctttgat-gacaccgtcttctcg-3') (SEQ ID NO:81) under the following reaction conditions: pre-denaturing at 94° C. for 5 min; 35 cycles of denaturing at 94° C. for 40s and extending at 68° C. for 40s; extending at 75° C. for 5 min. The second round of PCR was carried out in a final volume of 20 ul using 2 ul of the first round reaction product as template and using primers B5 (4372-7392, 5'-gccgcagcaaaggcatccatg-3') (SEQ ID NO:82) and B3 (4554-4575, 5'-gtgtacttccaaaaccacgc-3') (SEQ ID NO:83)under the following reaction conditions: pre-denaturing at 94° C. for 5 min; 35 cycles of denaturing at 94° C. for 40s, annealing at 56° C. for 40s and extending at 72° C. for 1 min 20 sec; extending at 75° C. for 5 min.

Grouping of rhesus monkeys used in this experiment: immunized group 1 including rhesus monkeys V10, V11 and V12 corresponding to animals HF1, HF2 and HF3 in Example 2, respectively; immunized group 2 including rhesus monkeys V13, V14 and V15 corresponding to animals HF4, HF5 and HF6 in Example 2, respectively; a control group including three non-immunized rhesus monkeys designated V16, V17 and V18.

Challenging with HEV

HEV in a PCR-detectable amount was used as one infection dosage. Three weeks after the last vaccination of the rhesus monkey HF1-6 with vaccine comprising the recombinant polypeptides of the present invention as described in Example 13, the above monkeys were challenged with 1,000 infection dosages of HEV. After challenge ALT of every monkey did not increase. Anti-NE2I-IgG in animals V16 and V17 was detected at week 4, and Anti-NE2-IgG was detected in animal V18 at week 5. From days 1 to 37, no HEV excretion was detected in animals V10-15; HEV excretion in animal V16 started on day 5 and ended on day 30; and HEV excretion in animals V17 and V18 began on day 5 too, but didn't stop on day 37. These results indicated that the polypeptide of the present invention as vaccine possessed better immunogenicity and produced better protection compared with the polypeptide trpE-C2 of HEV ORF2 in U.S. Pat. No. 5,885,768.

From these results, it could be seen that when low dosage of vaccine of this invention was used to vaccinate monkeys, the vaccinated monkeys could produce excellent antibody response to HEV and abnormal ALT and virus excretion in fecal were not observed after challenge with HEY. Thus better immunoprotection was produced compared with the reported vaccination results of the vaccines prepared using polypeptide trpE-C2 from HEV ORF2 (U.S. Pat. No. 5,885,768) and of the vaccines comprising the polypeptides prepared by Tsarev et al. In addition, the baculovirus expression system applied by Tsarev and Genelabs co. has potential harm to human body, so there was no report hitherto that any recombinant protein expressed by this system was approved as a commercialized drug or a commercialized vaccine used in human. On the contrary, several of the recombination proteins expressed by *E. coli* expression system according to the present invention were approved as commercialized in vivo drugs used in human, and have more reliable safety.

Example 15

Preparation of a Chimeric Polypeptide Comprising Polypeptide 247 of the Invention Linked with the Epitope in HEV ORF3

PCR reaction was performed with the full length genome of hepatitis E virus (HEV) isolated from a HEV patient of XinJiang, China. (Aye, T. T., Uchida et al. Nucleic Acids Research, 20(13), 3512 (1992); GenBank accession number: G1221701) as template using the forward primer, 372FP (5'-ggateccatatgaataacatgtatttgct-3') (SEQ ID NO:84), introducing restricted endonuclease sites BamHI and NdeI at its 5'-terminal, and the reverse primer, 372BRP (5'-ggatcctcggcgcggcc-3') (SEQ ID NO:85), introducing a restricted endonuclease site BamHI in its 5'-terminal, under the following reaction condition: 94° C. 5 min, 30 cycles of 94° C. 50 sec, 56° C. 50 sec and 72° C. 30 sec, and 70° C. 10 min. A specific DNA fragment with the size of about 370 bp encoding the epitope in HEV ORF3 was obtained. The PCR product obtained above was ligated into commercial pMD 18-T plasmid (TAKARA co.). A positive sub-clone in which the epitope gene in HEV ORF3 was inserted was identified by digestion with BamHI. DNA sequencing indicated no mutation in the clone, and thereby the amino acid sequence of the epitope gene in HEV ORF3 was obtained, as set forth in SEQ ID NO: 11.

The HEV-ORF3 gene fragment was obtained by digestion with BamHI, and ligated into pTO-T7-ORF2-247 expression plasmid vector (prepared according to the method described in Example 1) which had been digested with BamHI. A positive expression clone, pTO-T7-ORF3-247, in which the HEV ORF3 gene fragment was inserted, was identified by digestion with BamHI. The clone was transformed into *E. coli* ERR2566 strain, which was used to express the ORF3-247 chimeric polypeptide.

Example 16

Preparation of a Chimeric Polypeptide of NE2D Linked with Hemagglutin Antigen from Influenza Virus The nucleotide sequence of the chimeric peptide was obtained by PCR amplification with a HEV-ORF2 mutant sequence (SEQ ID NO:6) prepared in example 1 as template by using primer pairs HAFP/E2RD. The PCR reaction is carried out as follows: pre-heating at 94° C. for 5 minutes; 30 cycles of denaturation at 94° C. for 50 seconds, annealing at 56° C. for 50 seconds, extension at 72° C. for 70 seconds; and extension at 72° C. for 10 minutes at last. The resulted PCR product is an about 800 by DNA fragment, encoding chimeric polypeptide comprising HA from influenza virus and polypeptide NE2D of present invention. The forward primer HAFP contains BamHI and NdeI restriction sites. The reverse primer E2RD contained EcoRI restriction site and a stop translation codon TAA. The sequence for NdeI site is CAT ATG, wherein ATG is an initial translation codon. Moreover, in order to maintain the exact conformations of the two peptides HA and NE2D, respectively, a flexible linker Gly-Gly-Ser (SEQ ID NO:86) coded by CAG CTG TTC (SEQ ID NO:87) was introduced between HA and NE2D peptides. Therefore, the chimeric polypeptide HA-NE2D could be suitably employed in HEV vaccine. The sequences of primer pairs are as follows:

```
HAFP: 5'- AGA TCT CAT ATG TCT AAA GCT TTC TCT AAC TGC TAC CCT
          BglII NdeI  91 Ser Lys Ala Phe Ser Asn Cys Tyr Pro

TAC GAC GTT CCG GAC TAC GCT TCT TTA     GGT GGA TCC
Tyr Asp Val Pro Asp Tyr Ala Ser Leu108  Gly Gly Ser         (SEQ ID NO: 88)

CAG CTG TTC TAC TCT CGT CC-3'                               (SEQ ID NO: 89)

E2RD: 5'-gaattcttaggggggctaaaacagc-3'                       (SEQ ID NO: 90)
```

Preparation of Expression Vector Comprising a Nucleic Acid Construction Encoding Resulted Chimeric Polypeptide The aforementioned PCR product was cloned into commercial available plasmid pMD 18-T (TAKARA corn. Ltd.). The interest sequence then was acquired by BamHI/EcoRI digestion from pMD 18-T-HA-ORF2-NE2D plasmid, and integrated into expression vector with BamHI/EcoRI digestion and ligation. An HA-ORF2-NE2D chimeric peptide was isolated from *E. coli* ERR2566 host cells transformed with the pTO-T7-HA-ORF2-NE2D expression plasmid. The amino acid sequence was designated as SEQ ID NO: 12.

Example 17

Detecting IgG for HEV in Biological Samples with the Indirect Elisa Kit Based on Polypeptide NE2I of this Invention The kit detecting IgG for HEV with polypeptide NE2I of this invention comprises: microtiter plate coated with recombination polypeptide NE2I and blocked with blocking solution (20 mM pH7.2 PB, 0.5% Casein, 2% Gelatin); sample diluent (20 mM pH7.2 PB, 1% Casein); working conjugate (goat anti-human IgG (DAKO) labeled with HRP diluted with enzyme diluent (20 mM pH7.2 PB, 0.5% Casein, 10% NBS)); nonbioactivity material such as 20×PBST, chromatogen A, chromatogen B and stop solution (Beijing wantai).

Series of monkeys' sera were detected with anti-HEV IgG kit based on NE2I compared with two commercial anti-HEV IgG kits from Beijing wantai and Singapore Genelabs. The monkeys' sera were the sera of monkeys No 1, No 2, No 3 and No 13 mocking natural infected monkey by HEV from 0 to 18 weeks after intravenous challenge.

The manipulating procedure is as follows: add 100 ul of sample soluent to each microtiter; add 10 ul of specimen to the microtiter; mix thoroughly by tapping gently on all sides of microplate; Incubate for 30 minutes at 37° C.; wash the microplate with 1.times. PBST five times; blot dry by inverting the microplate and tapping firmly onto absorbent paper; add 100ul of working conjugate to all wells and incubating the microplate for 30 minutes at 37° C.; wash the microplate five times again and blotting dry; add 50ul of chromatogen A and 50ul of chromatogen B and mixing thoroughly by tapping gently; incubate the microplate for 10 minutes at 37° C. in dark; add 50ul of stop solution to each well and mixing gently-by tapping the plate; determine the absorbance for each well at 450 nm/620 nm. The two commercial anti-HEV IgG kits was assayed accurately according to each assay procedure.

The result is as follows: the kit based on NE2I detected seroconversion earlier than the two commercial kits from Beijing wantai and Singapore Genelabs by 7-14 days; the duration of anti-NE2I-IgG was longer than Genelabs anti-HEV-IgG and Wantai anti-HEV-IgG; the detectable rate of anti-NE2I-IgG was higher than the two commercial anti-HEV-IgG kits (see FIG. 10, raw data shown in table 5). When 34 random sera of normal people were detected, the positive rates of anti-NE2I-IgG and of Genelabs anti-HEV-IgG were 35% and 11% respectively, and the later was absolutely included in the former. When 263 clinical sera of hepatitis patients, the positive rates of anti-NE2I-IgG and of Wantai anti-HEV-IgG were 27.2% and 10.6% respectively. When 91 sera of non-A, non-B, non-C hepatitis patients, the positive rates of anti-NE2I-IgG and of Genelabs anti-HEV-IgG were 69.2% and 24.2% respectively. In a word, the anti-HEV-IgG based on NE2I of this invention is better sensitive than the commercial anti-HEV-IgG kits.

TABLE 5

Comparison of sensitivity for detection HEV infected monkey serum by anti-HEV IgG antibody detection kit of present invention (NE2I-IgG) and by two commercial available detection kit (Genelabs; WANTAI)

| | 0w | 1w | 2w | 3w | 4w | 5w | 6w | 7w | 8w | 9w | 10w |
|---|---|---|---|---|---|---|---|---|---|---|---|
| Serum No. 1 | | | | | | | | | | | |
| Genelabs Anti-HEV-IgG | 0.01 | 0.01 | 0.01 | 0.01 | 0.21 | 2.61 | 3 | 3 | 3 | 2.61 | 1.78 |
| WANTAI Anti-HEV-IgG | 0.01 | 0.02 | 0.01 | 0.02 | 0.01 | 1.82 | 2.45 | 2.48 | 2.42 | 1.7 | 1.37 |
| inventive NE2I-IgG | 0.01 | 0.02 | 0.01 | 1.87 | 2.56 | 2.5 | 2.52 | 2.49 | 2.72 | 2.52 | 2.52 |
| Serum No. 2 | | | | | | | | | | | |
| Genelabs Anti-HEV-IgG | 0.05 | 0.07 | 0.05 | 0.04 | 3 | 3 | 3 | 3 | 3 | 3 | 3 |
| WANTAI Anti-HEV-IgG | 0.02 | 0.02 | 0.02 | 0.02 | 2.05 | 2.58 | 2.42 | 2.46 | 2.65 | 2.5 | 2.33 |
| inventive NE2I-IgG | 0.06 | 0.06 | 0.06 | 0.77 | 2.26 | 2.36 | 2.5 | 2.56 | 2.62 | 2.65 | 2.49 |
| Serum No. 3 | | | | | | | | | | | |
| Genelabs Anti-HEV-IgG | 0.05 | 0.02 | 0.02 | 0.02 | 0.78 | 3 | 3 | 2.91 | 2.83 | 2.77 | 2.22 |
| WANTAI Anti-HEV-IgG | 0 | 0 | 0 | 0.02 | 0.02 | 1.87 | 1.62 | 1.67 | 1.82 | 1.48 | 1.05 |
| inventive NE2I-IgG | 0.01 | 0.05 | 0.04 | 0.83 | 2.2 | 2.63 | 2.59 | 2.62 | 2.75 | 3 | 2.7 |
| Serum No. 13 | | | | | | | | | | | |
| Genelabs Anti-HEV-IgG | 0.04 | 0.03 | 0.03 | 0.03 | 0.04 | 0.05 | 0.15 | 0.1 | 0.08 | 0.06 | 0.06 |
| WANTAI Anti-HEV-IgG | 0.02 | 0 | 0.01 | 0.01 | 0.01 | 0 | 0.01 | 0.02 | 0.04 | 0.03 | 0.03 |
| inventive NE2I-IgG | 0.1 | 0.11 | 0.09 | 0.09 | 2.3 | 2.45 | 2.51 | 2.5 | 2.34 | 2.21 | 2.13 |

| | 11w | 12w | 13w | 14w | 15w | 16w | 17w | 18w |
|---|---|---|---|---|---|---|---|---|
| Serum No. 1 | | | | | | | | |
| Genelabs Anti-HEV-IgG | 1.36 | 0.92 | 0.92 | 0.92 | 0.96 | 0.72 | | |
| WANTAI Anti-HEV-IgG | 0.54 | 0.36 | 0.25 | 0.18 | 0.1 | 0.05 | 0.05 | 0.03 |
| inventive NE2I-IgG | 2.47 | 2.53 | 2.58 | 2.64 | 2.65 | 2.40 | 2.36 | 2.35 |

TABLE 5-continued

Comparison of sensitivity for detection HEV infected monkey serum by
anti-HEV IgG antibody detection kit of present invention (NE2I-IgG)
and by two commercial available detection kit (Genelabs; WANTAI)

| Serum No. 2 | | | | | | | | |
|---|---|---|---|---|---|---|---|---|
| Genelabs Anti-HEV-IgG | 3 | 3 | 3 | 3 | 3 | 3 | | |
| WANTAI Anti-HEV-IgG | 2.23 | 2.3 | 2.21 | 2.2 | 2.26 | 2.26 | 2.38 | 2.46 |
| inventive NE2I-IgG | 2.47 | 2.4 | 2.54 | 2.51 | 2.38 | 2.29 | 2.34 | 2.33 |
| Serum No. 3 | | | | | | | | |
| Genelabs Anti-HEV-IgG | 1.95 | 1.79 | 1.54 | 1.42 | 1.42 | 1.38 | | |
| WANTAI Anti-HEV-IgG | 0.67 | 0.75 | 0.76 | 0.58 | 0.38 | 0.46 | 0.34 | 0.23 |
| inventive NE2I-IgG | 2.6 | 2.55 | 2.6 | 2.54 | 2.51 | 2.51 | 2.36 | 2.51 |
| Serum No. 13 | | | | | | | | |
| Genelabs Anti-HEV-IgG | 0.07 | 0.08 | 0.07 | 0.1 | 0.15 | 0.07 | 0.04 | 0.02 |
| WANTAI Anti-HEV-IgG | 0.03 | 0.02 | 0.02 | 0.02 | 0.02 | 0.02 | | |
| inventive NE2I-IgG | 2.14 | 2.05 | 2.01 | 1.82 | 1.87 | 1.79 | 1.7 | 1.6 |

Example 18

Method for Labeling the Recombinant Proteins of Present Invention with HRP

Dissolving 1 mg of HRP (Biozyme R/Z>3) and NaIO4, respectively, in ultra-pure water (UPW); adding drop-wisely NaIO4 solution with agitation; the mixture solution is stand for 30 minutes in dark at room temperature; stepwise add 100 ul of 1% ethylene glycol solution, mixing; allow it to stand for 30 minutes in dark at 4° C. Dialyze recombination protein against carbonate buffer (10 mM pH9.6) 3 hours; add appropriate dialyzed recombination protein to the oxygenized HRP, dialyze for 6 hours at room temperature (or 4° C.) in carbonate buffer (10 mM pH9.5) with gently stirring; add 20ul of freshly prepared 0.1 M NaBH4 solution to the above-mentioned blending; allow it to stand for 2 hours at 4° C. in darkness, gently vortex once each 30 minutes; dialyze it in PBS (10 mM pH7.2) overnight at 4° C.

Example 19

Diagnostic Kit for Detecting Antibody IgM Against HEV in Biological Samples and Capture Assay for Detecting Antibody IgM against HEV in Biological Samples Polypeptide 225N was labeled with HRP according to the method described in example 18.

The diagnostic kit for detecting antibody IgM against HEV containing HRP-labeled polypeptide NE2I of present invention comprises: microtiter strip that is pre-coated with mouse anti-human IgM u chain polyclonal antibody (Dako company, Denmark) and blocked with blocking solution; sample diluent (20 mM pH7.2 PB, 1% Casein); working conjugate (HRP-labeled polypeptide 225N that is suitably diluted with enzyme diluent (20 mM 017.2 PB, 0.5% Casein, 10% NBS)); non-bioactivity material, such as 20×PBST, chromatogen agent A, chromatogen agent B and Stop solution (WANTAI company, Beijing).

The capture assay using present diagnostic kit is carried out as follows: adding 100 ul of diluent buffer to each well which is pre-coated with mouse anti-human IgM p. chain polyclonal antibody; adding 1 ul of sample to be detected into the diluent buffer; mixing thoroughly by tapping gently; incubating for 30 minutes at 37° C.; washing with PBST for five times; blot dry by inverting the microplate up-side-down and tapping firmly onto tissue; adding 100 ul of working conjugate (HRP-labeled polypeptide 225N that is suitably diluted) to each well and incubating the microplate for 30 minutes at 37° C.; washing five times again and blotting dry; then adding 50 ul of chromatogen A and 50 ul of chromatogen B and mixing thoroughly by tapping gently; incubating for 10 minutes at 37° C. in dark; add 50 ul of stop solution to each well and mixing gently by tapping the plate; determine the absorbance for each well at $OD_{450nm/620nm}$.

Using the diagnostic anti-HEV-IgM kit as prepared in accordance with present invention, 263 clinical sera of hepatitis patients were detected by aforementioned capture assay with the positive rate of 11%; and 91 sera of non-A, non-B, non-C hepatitis patients were also detected by said capture assay with the positive rate of 48.4%. Meanwhile, the positive rate for these 91 sera sample detected by diagnostic kit of anti-HEV-IgG from Genelabs was merely 24.2%. As indicated by the above results, the positive sample detected by diagnostic anti-HEV-IgM kit of present invention using capture assay is in good accordance with the clinical diagnosis. Moreover, most of positive samples detected by Genelabs anti-HEV-IgG kit are also positive in the present capture assay. That is to say, the anti-HEV-IgM kit of present invention as well as said capture assay possess higher sensitivity and specificity in clinical HEV diagnosis than that of existing commercial available kits.

Example 20

Diagnostic Kit for Detecting Total Antibodies against HEV in Biological Samples and the Method for Detecting Total Antibodies against HEV in Biological Samples Polypeptide 225N was labeled with horseradish peroxidase (HRP) according to the method described in example 18.

The kit detecting total antibodies for HEV containing polypeptides NE2I and 225N of present invention comprises: microtiter strip pre-coated with recombination polypeptide NE2I and blocked with blocking solution (20 mM pH7.2 PB, 0.5% Casein, 2% Gelatin); working conjugate (polypeptide 225N labeled with HRP diluted with enzyme diluent (20 mM pH7.2 PB, 0.5% Casein, 10% NBS)); non-bioactivity material, such as 20×PBST, chromatogen agent A, chromatogen agent B and stop solution (WANTAI company, Beijing).

The detecting protocol of present kit is as follows: adding 50 ul of serum and 50 ul of suitable diluted recombinant polypeptide 225N that is HRP labeled into the microtiter on said strip which is in advance coated with polypeptide NE2I; mixing by tapping gently on all sides of micro-plate; incubating for 60 minutes at 37° C.; washing the micro-plate with PBST for five times; blot dry by inverting the micro-plate; adding 50 ul of chromatogen A and 50 ul of chromatogen B; and then incubating the microplate for 15 minutes at 37° C.; finally, adding 50 ul of stop solution to each well and mixing gently by tapping the plate; determine the absorbance for each well at $OD_{450nm/620nm}$.

The detection results is provided as follows: detected with the sandwich total anti-HEV antibodies kit based on polypeptides NE2I and 225N of present invention, 263 clinical sera from hepatitis patients were detected with the positive rate of 52%, while only 10.6% is determined by detecting with WANTAI anti-HEV-IgG kit. And further 91 sera of non-A, non-B, non-C hepatitis patients were detected using the same sandwich kit, with the positive rate of 54.9%. However, in these 91 sera, the positive rate detected by Genelabs anti-HEV-IgG was merely 24.2%. As indicated by the above data, detection with the present diagnostic kit is superior to that of existing commercial available kits in clinical diagnosis.

We claim:

1. A multimer of purified monomeric polypeptides, wherein said multimer is formed by 2-180 purified monomeric polypeptides via self-aggregation, and each said purified monomeric polypeptide is selected from the group consisting of
   (a) a fragment of SEQ ID No. 1 of hepatitis E virus ORF 2 wherein the amino terminus starts from between amino acid residues 370 and 469, and the carboxyl terminus ends from between amino add residues 601 and 628, wherein the fragment of SEQ ID No. 1 is selected from the group consisting of
   - a polypeptide having the amino acid sequence of amino acid residues 394 to 628 from SEQ ID No. 1,
   - a polypeptide having the amino acid sequence of amino acid residues 394 to 618 from SEQ ID No. 1,
   - a polypeptide having the amino acid sequence of amino acid residues 394 to 602 from SEQ ID No. 1,
   - a polypeptide having the amino acid sequence of amino acid residues 394 to 601 from SEQ ID No. 1,
   - a polypeptide having the amino acid sequence of amino acid residues 394 to 606 from SEQ ID No. 1,
   - a polypeptide having the amino acid sequence of amino acid residues 390 to 603 from SEQ ID No. 1,
   - a polypeptide having the amino acid sequence of amino acid residues 374 to 618 from SEQ ID No. 1,
   - a polypeptide having the amino acid sequence of amino acid residues 414 to 602 from SEQ ID No. 1,
   - a polypeptide having the amino acid sequence of amino acid residues 414 to 601 from SEQ ID No. 1, and
   - a polypeptide having the amino acid sequence of amino acid residues 459 to 628 from SEQ ID No. 1, and (b) a polypeptide having the amino acid sequence of amino acid residues X to 603 from SEQ ID No. 1 with Met added at the N-terminus and a modified C-terminus, wherein the modified C-terminus is an addition, in the 5' to 3' direction, of amino acid sequence -Pro-Pro-Arg at amino acid residue 603, Pro, on its 3' end and wherein
   - when X is amino acid residue 394, the polypeptide is as set forth in SEQ ID No. 2;
   - when X is amino acid residue 414, the polypeptide is as set forth in SEQ ID No. 3;
   - when X is amino acid residue 429, the polypeptide is as set forth in SEQ ID No. 4;
   - when X is amino acid residue 439, the polypeptide is as set forth in SEQ ID No. 7;
   - when X is amino acid residue 449, the polypeptide is as set forth in SEQ ID No. 8;
   - when X is amino acid residue 459, the polypeptide is as set forth in SEQ ID No. 9; or
   - when X is amino acid residue 469, the polypeptide is as set forth in SEQ ID No. 10.

2. A vaccine composition for prophylaxis of hepatitis E virus infection in mammals, which comprises a multimer according to claim 1, and optionally, pharmaceutically acceptable vehicles and/or an adjuvant.

3. A chimeric protein comprising a polypeptide selected from the group consisting of
   - a polypeptide having the amino acid sequence of amino acid residues 394 to 628 from SEQ ID No. 1,
   - a polypeptide having the amino acid sequence of amino acid residues 394 to 618 from SEQ ID No. 1,
   - a polypeptide having the amino acid sequence of amino acid residues 394 to 602 from SEQ ID No. 1,
   - a polypeptide having the amino acid sequence of amino acid residues 394 to 601 from SEQ ID No. 1,
   - a polypeptide having the amino acid sequence of amino acid residues 394 to 606 from SEQ ID No. 1,
   - a polypeptide having the amino acid sequence of amino acid residues 390 to 603 from SEQ ID No. 1,
   - a polypeptide having the amino acid sequence of amino acid residues 374 to 618 from SEQ ID No. 1,
   - a polypeptide having the amino acid sequence of amino acid residues 414 to 602 from SEQ ID No. 1,
   - a polypeptide having the amino acid sequence of amino acid residues 414 to 601 from SEQ ID No. 1,
   - a polypeptide having the amino acid sequence of amino acid residues 459 to 628 from SEQ ID No.1, and
   - a polypeptide having the amino acid sequence of amino acid residues X to 603 from SEQ ID No. 1 with Met added at the N-terminus and a modified C-terminus, wherein the modified C-terminus is an addition, in the 5' to 3' direction, of amino acid sequence -Pro-Pro-Arg at amino acid residue 603, Pro, on its 3' end and wherein
     - when X is amino acid residue 394, the polypeptide is as set forth in SEQ ID No. 2;
     - when X is amino acid residue 414, the polypeptide is as set forth in SEQ ID No. 3;
     - when X is amino acid residue 429, the polypeptide is as set forth in SEQ ID No. 4;
     - when X is amino acid residue 439, the polypeptide is as set forth in SEQ ID No. 7;
     - when X is amino acid residue 449, the polypeptide is as set forth in SEQ ID No. 8;
     - when X is amino acid residue 459, the polypeptide is as set forth in SEQ ID No. 9; or
     - when X is amino acid residue 469, the polypeptide is as set forth in SEQ ID No. 10;

and a conserved fragment of hemagglutinin antigen from influenza virus.

4. A multimer of purified monomeric polypeptides, wherein said multimer is formed by 2-180 purified monomeric polypeptides via self aggregation, and each said purified monomeric polypeptide is the chimeric protein of claim 3.

5. A vaccine composition for prophylaxis of hepatitis E virus infection in mammals, which comprises chimeric protein according to claim 4 or a multimer according to claim 4, and optionally, a pharmaceutically acceptable vehicle and/or an adjuvant.

6. A chimeric protein comprising a polypeptide selected from the group consisting of a polypeptide having the amino acid sequence of amino acid residues 394 to 628 from SEQ ID No. 1,
a polypeptide having the amino acid sequence of amino acid residues 394 to 618 from SEQ ID No. 1,
a polypeptide having the amino acid sequence of amino acid residues 394 to 602 from SEQ ID No. 1,
a polypeptide having the amino acid sequence of amino acid residues 394 to 601 from SEQ ID No. 1,
a polypeptide having the amino acid sequence of amino acid residues 394 to 606 from SEQ ID No. 1,
a polypeptide having the amino acid sequence of amino acid residues 390 to 603 from SEQ ID No. 1,
a polypeptide having the amino acid sequence of amino acid residues 374 to 618 from SEQ ID No. 1,
a polypeptide haying the amino acid sequence of amino acid residues 414 to 602 from SEQ ID No. 1,
a polypeptide having the amino acid sequence of amino acid residues 414 to 601 from SEQ ID No. 1,
a polypeptide having the amino acid sequence of amino acid residues 459 to 628 from SEQ ID No. 1, and
a polypeptide having the amino acid sequence of amino acid residues X to 603 from SEQ ID No. 1 with Met added at the N-terminus and a modified C-terminus, wherein the modified C-terminus is an addition, in the 5' to 3' direction, of amino acid sequence -Pro-Pro-Arg at amino acid residue 603, Pro, on its 3' end and wherein
when X is amino acid residue 394, the polypeptide is as set forth in SEQ ID No. 2;
when X is amino acid residue 414, the polypeptide is as set forth in SEQ ID No. 3;
when X is amino acid residue 429, the polypeptide is as set forth in SEQ ID No. 4;
when X is amino acid residue 439, the polypeptide is as set forth in SEQ ID No. 7;
when X is amino acid residue 449, the polypeptide is as set forth in SEQ ID No. 8;
when X is amino acid residue 459, the polypeptide is as set forth in SEQ ID No. 9; or when X is amino acid residue 469, the polypeptide is as set forth in SEQ ID No. 10;
and an immunogenic epitope from hepatitis E virus ORF3 or an immunogenic fragment thereof.

7. A multimer of purified monomeric polypeptides, wherein said multimer is formed by 2-180 purified monomeric polypeptides via self-aggregation, and each said purified monomeric polypeptide is a chimeric protein of claim 6.

8. A vaccine composition for prophylaxis of hepatitis E virus infection in mammals, which comprises a chimeric protein according to claim 6 or a multimer according to claim 8, and optionally, a pharmaceutically acceptable vehicle and/or an adjuvant.

9. A recombinant expression vector comprising the nucleotide sequence encoding a polypeptide selected from the group consisting of
a polypeptide having the amino acid sequence of amino acid residues 394 to 628 from SEQ ID No. 1,
a polypeptide having the amino acid sequence of amino acid residues 394 to 618 from SEQ ID No. 1,
a polypeptide having the amino acid sequence of amino acid residues 394 to 602 from SEQ ID No. 1,
a polypeptide having the amino acid sequence of amino acid residues 394 to 601 from SEQ ID No. 1,
a polypeptide having the amino acid sequence of amino acid residues 394 to 606 from SEQ ID No. 1,
a polypeptide having the amino acid sequence of amino acid residues 390 to 603 from SEQ ID No. 1,
a polypeptide having the amino acid sequence of amino acid residues 374 to 618 from SEQ ID No. 1,
a polypeptide having the amino acid sequence of amino acid residues 414 to 602 from SEQ ID No. 1,
a polypeptide having the amino acid sequence of amino acid residues 414 to 601 from SEQ ID No. 1,
a polypeptide having the amino acid sequence of amino acid residues 459 to 628 from SEQ ID No.1, and
a polypeptide having the amino acid sequence of amino acid residues X to 603 from SEQ ID No. 1 with Met added at the N-terminus and a modified C-terminus, wherein the modified C-terminus is an addition, in the 5' to 3' direction, of amino acid sequence -Pro-Pro-Arg at amino acid residue 603, Pro, on its 3' end and wherein
when X is amino acid residue 394, the polypeptide is as set forth in SEQ ID No. 2;
when X is amino acid residue 414, the polypeptide is as set forth in SEQ ID No. 3;
when X is amino acid residue 429, the polypeptide is as set forth in SEQ ID No. 4;
when X is amino acid residue 439, the polypeptide is as set forth in SEQ ID No. 7;
when X is amino acid residue 449, the polypeptide is as set forth in SEQ ID No. 8;
when X is amino acid residue 459, the polypeptide is as set forth in SEQ ID No. 9; or
when X is amino acid residue 469, the polypeptide is as set forth in SEQ ID No. 10.

10. A host cell transformed with the recombinant expression vector according to claim 9.

11. A diagnostic kit for the diagnosis of hepatitis E virus infection in biological sample, which comprises a diagnosis effective amount of a multimer according to claim 1.

12. The diagnostic kit according to claim 11, which further comprises the polypeptide containing immunogenic epitope from hepatitis E virus ORF3 or an immunogenic fragment thereof, wherein said polypeptide containing immunogenic epitope from hepatitis E virus ORF3 or an immunogenic fragment thereof is optionally, covalently bound to the monomeric polypeptide.

13. The diagnostic kit according to claim 11 or 12 for determination of antibody IgG against hepatitis E virus in the biological sample, wherein if desired, said polypeptide is pre-coated on the surface of a suitable support; and the kit further comprises detectable labeled antibody anti-IgG that is directed against IgG from biological sample to be detected, and detection agent corresponding to said detectable label, and if desired, further comprises a suitable buffer system.

14. The diagnostic kit according to claim 11 or 12 for determination of antibody IgM against hepatitis E virus in the biological sample, which comprise detectable labeled antibody anti-IgM as capture antibody that is directed against IgM from biological sample to be detected, if desired, said capture antibody is pre-coated on the surface of a suitable support; and further comprises at least one of the monomeric polypeptides or the multimers which are detectable labeled , and a detection agent corresponding to said detectable label; if desired, further comprises a suitable buffer system.

15. The diagnostic kit according to claim 11 or 12 for determination of total antibodies against hepatitis E virus in the biological sample, wherein, if desired, said polypeptide is pre-coated on the surface of a suitable support; and further comprises at least one of the monomeric polypeptides or the multimers which are detectable labeled, and detection agent corresponding to said detectable label; wherein said polypeptide or multimer for pre-coating the surface of a support and the detectable labeled polypeptide or multimer could be the same, or different one.

16. A method for detecting total antibodies against hepatitis E virus in biological samples, comprising the step of: immobilizing a multimer according to claim 1 on the surface of a support; contacting it with sample to be detected under the conditions suitable for the interaction of antigen and antibody; washing with a suitable buffer; and detecting antigen/antibody complex on the surface of a support by using antigen of hepatitis E virus with a detectable label and corresponding detect agent.

17. A method for detecting antibody IgG against hepatitis E virus in biological samples, comprising the step of: immobilizing a multimer according to claim 1 on the surface of a support; contacting it with sample to be detected under the conditions suitable for the interaction of antigen and antibody; washing with a suitable buffer; and detecting the antigen/antibody complex on the surface of a support by using detectable labeled antibody anti-IgG against hepatitis E virus and corresponding detect agent.

18. A method for detecting antibody IgM against hepatitis E virus in biological samples, comprising the step of immobilizing antibody anti-IgM on the surface of a support; contacting it with sample to be detected under the conditions suitable for the interaction of antigen and antibody; washing with a suitable buffer; and detecting the anti-IgM/IgM complex on the surface of a support by using detectable labeled at least one of the polypeptides recited in claim 1 or the multimers according to claim 1 and corresponding detect agent.

19. A method for detecting antibody IgM against hepatitis E virus in biological samples, comprising the step of: immobilizing antibody anti-IgM on the surface of a support; contacting it with sample to be detected under conditions suitable for the interaction of antigen and antibody; washing with a suitable buffer; and then contacting with a multimer according to claim 1 under conditions suitable for the interaction of antigen and antibody; washing with a suitable buffer; and then detecting antigen/antibody complex on the surface of a support by using detectable labeled anti-HEV polyclonal or monoclonal antibody and corresponding detect agent.

20. A diagnostic kit for the diagnosis of hepatitis E virus infection in a biological sample or for the determination of antibody IgG, antibody IgM, or total antibodies against hepatitis E virus in the biological sample, comprising chimeric protein according to claim 3 or multimer according to claim 4.

21. A diagnostic kit for the diagnosis of hepatitis E virus infection in a biological sample or for the determination of antibody IgG, antibody IgM, or total antibodies against hepatitis E virus in the biological sample, comprising a chimeric protein according to claim 6 or a multimer according to claim 7.

22. A vaccine composition for prophylaxis of hepatitis E virus infection in mammals, which comprises a polypeptide selected from the group consisting of
  a polypeptide having the amino acid sequence of amino acid residues 394 to 628 from SEQ ID No. 1,
  a polypeptide having the amino acid sequence of amino acid residues 394 to 618 from SEQ ID No. 1,
  a polypeptide having the amino acid sequence of amino acid residues 394 to 602 from SEQ ID No. 1,
  a polypeptide having the amino acid sequence of amino acid residues 394 to 601 from SEQ ID No. 1,
  a polypeptide having the amino acid sequence of amino acid residues 394 to 606 from SEQ ID No. 1,
  a polypeptide having the amino acid sequence of amino acid residues 390 to 603 from SEQ ID No. 1,
  a polypeptide having the amino acid sequence of amino acid residues 374 to 618 from SEQ ID No. 1,
  a polypeptide having the amino acid sequence of amino acid residues 414 to 602 from SEQ ID No. 1,
  a polypeptide having the amino acid sequence of amino acid residues 414 to 601 from SEQ ID No. 1,
  a polypeptide having the amino acid sequence of amino acid residues 459 to 628 from SEQ ID No. 1, and
  a polypeptide having the amino acid sequence of amino acid residues X to 603 from SEQ ID No. 1 with Met added at the N-terminus and a modified C-terminus, wherein the modified C-terminus is an addition, in the 5' to 3' direction, of amino acid sequence -Pro-Pro-Arg at amino acid residue 603, Pro, on its 3' end and wherein
    when X is amino acid residue 394, the polypeptide is as set forth in SEQ ID No. 2;
    when X is amino acid residue 414, the polypeptide is as set forth in SEQ ID No. 3;
    when X is amino acid residue 429, the polypeptide is as set forth in SEQ ID No. 4;
    when X is amino acid residue 439, the polypeptide is as set forth in SEQ ID No. 7;
    when X is amino acid residue 449, the polypeptide is as set forth in SEQ ID No. 8;
    when X is amino acid residue 459, the polypeptide is as set forth in SEQ ID No. 9; or
    when X is amino acid residue 469, the polypeptide is as set forth in SEQ ID No. 10; and
optionally, pharmaceutically acceptable vehicles and/or an adjuvant.

23. A recombinant expression vector comprising the nucleotide sequence encoding chimeric protein according to claim 3.

24. A recombinant expression vector comprising the nucleotide sequence encoding a chimeric protein according to claim 6.

25. A diagnostic kit for the diagnosis of hepatitis E virus infection in biological sample, which comprises a diagnosis effective amount of a polypeptide selected from the group consisting of
  a polypeptide having the amino acid sequence of amino acid residues 394 to 628 from SEQ ID No. 1,
  a polypeptide having the amino acid sequence of amino acid residues 394to 618 from SEQ ID No. 1,
  a polypeptide having the amino acid sequence of amino acid residues 394 to 602 from SEQ ID No. 1,
  a polypeptide having the amino acid sequence of amino acid residues 394 to 601 from SEQ ID No. 1,
  a polypeptide having the amino acid sequence of amino acid residues 394 to 606 from SEQ ID No. 1,
  a polypeptide having the amino acid sequence of amino acid residues 390 to 603 from SEQ ID No. 1,
  a polypeptide having the amino acid sequence of amino acid residues 374 to 618 from SEQ ID No. 1,
  a polypeptide having the amino acid sequence of amino acid residues 414 to 602 from SEQ ID No. 1,
  a polypeptide having the amino acid sequence of amino acid residues 414 to 601 from SEQ ID No. 1,
  a polypeptide having the amino acid sequence of amino acid residues 459 to 628 from SEQ ID No.1, and
  a polypeptide having the amino acid sequence of amino acid residues X to 603 from SEQ ID No. 1 with Met added at the N-terminus and a modified C-terminus, wherein the modified C-terminus is an addition, in the 5' to 3' direction, of amino acid sequence -Pro-Pro-Arg at amino acid residue 603, Pro, on its 3' end and wherein when X is amino acid residue 394, the polypeptide is as set forth in SEQ ID No. 2;
when X is amino acid residue 414, the polypeptide is as set forth in SEQ ID No. 3;
when X is amino acid residue 429, the polypeptide is as set forth in SEQ ID No. 4;
when X is amino acid residue 439, the polypeptide is as set forth in SEQ ID No. 7;
when X is amino acid residue 449, the polypeptide is as set forth in SEQ ID No. 8;
when X is amino acid residue 459, the polypeptide is as set forth in SEQ ID No. 9; or
when X is amino acid residue 469, the polypeptide is as set forth in SEQ ID No. 10.

26. The diagnostic kit according to claim 25, which further comprises the polypeptide containing immunogenic epitope from hepatitis E virus ORF3 or an immunogenic fragment thereof, wherein said polypeptide containing immunogenic epitope from hepatitis E virus ORF3 or an immunogenic fragment thereof is optionally, covalently bound to the monomeric polypeptide.

* * * * *